(12) United States Patent
Ushikura et al.

(10) Patent No.: US 11,262,461 B2
(45) Date of Patent: Mar. 1, 2022

(54) RADIATION DETECTOR AND RADIOGRAPHIC IMAGING DEVICE

(71) Applicant: FUJIFILM Corporation, Tokyo (JP)

(72) Inventors: Shinichi Ushikura, Kanagawa (JP); Haruyasu Nakatsugawa, Kanagawa (JP); Keiichi Akamatsu, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 17/017,437

(22) Filed: Sep. 10, 2020

(65) Prior Publication Data

US 2020/0408930 A1 Dec. 31, 2020

Related U.S. Application Data

(63) Continuation of application No. PCT/JP2019/009953, filed on Mar. 12, 2019.

(30) Foreign Application Priority Data

Mar. 19, 2018 (JP) .............................. JP2018-051689
Nov. 22, 2018 (JP) .............................. JP2018-219695
Feb. 8, 2019 (JP) .............................. JP2019-022125

(51) Int. Cl.
  *G01T 1/17* (2006.01)
  *G01T 1/202* (2006.01)
  *G01T 1/208* (2006.01)

(52) U.S. Cl.
  CPC .............. *G01T 1/17* (2013.01); *G01T 1/2023* (2013.01); *G01T 1/208* (2013.01)

(58) Field of Classification Search
  CPC .......... G01T 1/17; G01T 1/2023; G01T 1/208
  See application file for complete search history.

(56) References Cited

U.S. PATENT DOCUMENTS

| 6,414,315 B1 | 7/2002 | Wei et al. |
| 2004/0094719 A1* | 5/2004 | Ogawa .................. G01T 1/2002 250/370.11 |

(Continued)

FOREIGN PATENT DOCUMENTS

| JP | H01145530 A | 6/1989 |
| JP | 2000-259804 A | 9/2000 |

(Continued)

OTHER PUBLICATIONS

"A New Dimensionally Stable Polyimide Film XENOMAX"; https://www.nagase.co.jp/display/english/pdf/fpd2014/toyobo.pdf.

(Continued)

*Primary Examiner* — Blake C Riddick
(74) *Attorney, Agent, or Firm* — Studebaker & Brackett PC

(57) ABSTRACT

A radiation detector includes a sensor substrate, a conversion layer, and a neutral stress plane adjustment member. The sensor substrate includes a flexible base member, and a layer provided on a first surface of the base member and formed with plural pixels configured to accumulate electrical charge generated in response to light converted from radiation. The conversion layer is provided on the opposite side of the layer formed with the plural pixels to the side where the base member is provided and is configured to convert radiation into the light. The neutral stress plane adjustment member is provided on a second surface side of the base member on the opposite side of the base member to the first surface and is configured to adjust a position of a neutral stress plane to within a predetermined range in a stacking direction.

20 Claims, 33 Drawing Sheets

(56) References Cited

U.S. PATENT DOCUMENTS

| | | | |
|---|---|---|---|
| 2011/0006213 A1 | 1/2011 | Sato et al. | |
| 2012/0068078 A1* | 3/2012 | Zhang | H01L 27/14609 |
| | | | 250/370.08 |
| 2012/0219114 A1 | 8/2012 | Iwakiri et al. | |
| 2012/0228509 A1* | 9/2012 | Kusayama | G01T 1/2002 |
| | | | 250/361 R |
| 2013/0154039 A1 | 6/2013 | Furui et al. | |
| 2013/0264461 A1 | 10/2013 | Okada et al. | |
| 2014/0103216 A1 | 4/2014 | Sasaki et al. | |
| 2014/0171796 A1 | 6/2014 | Kimoto et al. | |
| 2014/0353509 A1 | 12/2014 | Nakatsugawa | |
| 2015/0091117 A1 | 4/2015 | Heo et al. | |
| 2017/0160405 A1 | 6/2017 | Kim et al. | |
| 2018/0019269 A1* | 1/2018 | Klipstein | H01L 31/022408 |
| 2019/0387619 A1* | 12/2019 | Vasquez Quintero | |
| | | | B29D 11/00038 |

FOREIGN PATENT DOCUMENTS

| | | |
|---|---|---|
| JP | 2001-188086 A | 7/2001 |
| JP | 2011017683 A | 1/2011 |
| JP | 2012132768 A | 7/2012 |
| JP | 2012-173275 A | 9/2012 |
| JP | 2013217769 A | 10/2013 |
| JP | 2014077735 A | 5/2014 |
| JP | 2014081368 A | 5/2014 |
| JP | 2014-145783 A | 8/2014 |
| JP | 5627049 B2 | 11/2014 |
| JP | 5785201 B2 | 9/2015 |
| JP | 2017-015428 A | 1/2017 |
| WO | 2014/050862 A1 | 4/2014 |

OTHER PUBLICATIONS

Kazumasa Inoue et al.; "A study of materials Reducing Backscattered Radiations in X-ray for Diagnosis"; The Journal of Japan Academy of Health Sciences; 2004; pp. 218-224; vol. 7; No. 3.

International Search Report issued in PCT/JP2019/009953; dated Apr. 16, 2019.

International Preliminary Report on Patentability and Written Opinion issued in PCT/JP2019/009953; dated Sep. 22, 2020.

The extended European search report issued by the European Patent Office dated Mar. 29, 2021, which corresponds to European Patent Application No. 19772507.0-1001 and is related to U.S. Appl. No. 17/017,437.

An Office Action mailed by the Japanese Patent Office dated May 25, 2021, which corresponds to Japanese Patent Application No. 2020-508240 and is related to U.S. Appl. No. 17/017,437; with English language translation.

* cited by examiner

RADIATION DETECTOR AND RADIOGRAPHIC IMAGING DEVICE

CROSS-REFERENCE TO RELATED APPLICATIONS

This application is a continuation application of International Application No. PCT/JP2019/009953 filed Mar. 12, 2019, the disclosure of which is incorporated herein by reference in its entirety. Further, this application claims priorities from Japanese Patent Application No. 2018-051689, filed Mar. 19, 2018, Japanese Patent Application No. 2018-219695, filed Nov. 22, 2018, and Japanese Patent Application No. 2019-022125, filed Feb. 8, 2019, the disclosures of which are incorporated herein by reference in their entirety.

BACKGROUND

Technical Field

The present disclosure relates to a radiation detector and a radiographic imaging device.

Related Art

Radiographic imaging devices that perform radiographic imaging for medical diagnostic purposes are known. In such radiographic imaging devices, a radiation detector is employed to generate radiographic images by detecting radiation that has passed through an imaging subject.

Radiation detectors may include a conversion layer such as a scintillator to convert radiation into light, and a sensor substrate provided with plural pixels that accumulate electrical charges generated in response to the converted light from the conversion layer. Some such known radiation detectors employ a flexible base member for the sensor substrate (see for example Japanese Patent Application Laid-Open (JP-A) No. 2013-217769 (Patent Document 1)). Employing a flexible base member may for example enable a reduction in weight of the radiographic imaging device (radiation detector) or facilitate imaging of the imaging subject.

Since a flexible base member is employed in the technology of Patent Document 1, a bending adjustment member is provided to adjust bending characteristics (rigidity distribution). In the technology of Patent Document 1, the bending adjustment member causes bending of the overall device, integrally configured with the radiation detector and electric circuitry such as a controller to read the electrical charges from the radiation detector, thereby suppressing stress from concentrating at locations with low rigidity and a reduction in anti-shock performance.

However, the radiation detector may be handled on its own during processes to manufacture the radiographic imaging device and the like.

In radiographic imaging devices in which a radiation detector and electric circuitry are arranged in a direction intersecting a stacking direction in which the conversion layer and the sensor substrate are stacked, and the bending adjustment member is provided spanning over the entirety of the radiation detector and the electric circuitry, consideration is not given to the radiation detector being handled on its own. In radiographic imaging devices configured as described above, there is therefore a concern that the sensor substrate may detach from the conversion layer when the radiation detector is handled on its own.

SUMMARY

An object of the present disclosure is to provide a radiation detector and a radiographic imaging device that are better capable of suppressing detachment of a sensor substrate and a conversion layer of the radiation detector from one another than in a radiographic imaging device in which a radiation detector and electric circuitry are arranged in a direction intersecting a stacking direction in which a conversion layer and a sensor substrate are stacked and a bending adjustment member is provided spanning over the entirety of the radiation detector and the electric circuitry.

In order to realize the above object, a radiation detector of a first aspect of the present disclosure includes a sensor substrate, a conversion layer, and a neutral stress plane adjustment member. The sensor substrate includes a flexible base member, and a layer provided on a first surface of the base member and formed with plural pixels configured to accumulate electrical charge generated in response to light converted from radiation. The conversion layer is provided on the opposite side of the layer formed with the plural pixels to the side where the base member is provided and is configured to convert radiation into the light. The neutral stress plane adjustment member is provided on a second surface side of the base member on the opposite side of the base member to the first surface and is configured to adjust a position of a neutral stress plane to within a predetermined range in a stacking direction in which the sensor substrate and the conversion layer are stacked from an interface at a face of the conversion layer opposing the sensor substrate.

DETAILED DESCRIPTION

Detailed explanation follows regarding exemplary embodiments of the present disclosure, with reference to the drawings. Note that the present disclosure is not limited by these exemplary embodiments.

First Exemplary Embodiment

A radiographic imaging device of the present exemplary embodiment has a function of capturing radiographic images of an imaging target by detecting radiation that has passed through an imaging subject configuring the imaging target, and outputting image information expressing a radiographic image of the imaging subject.

Figure 1:
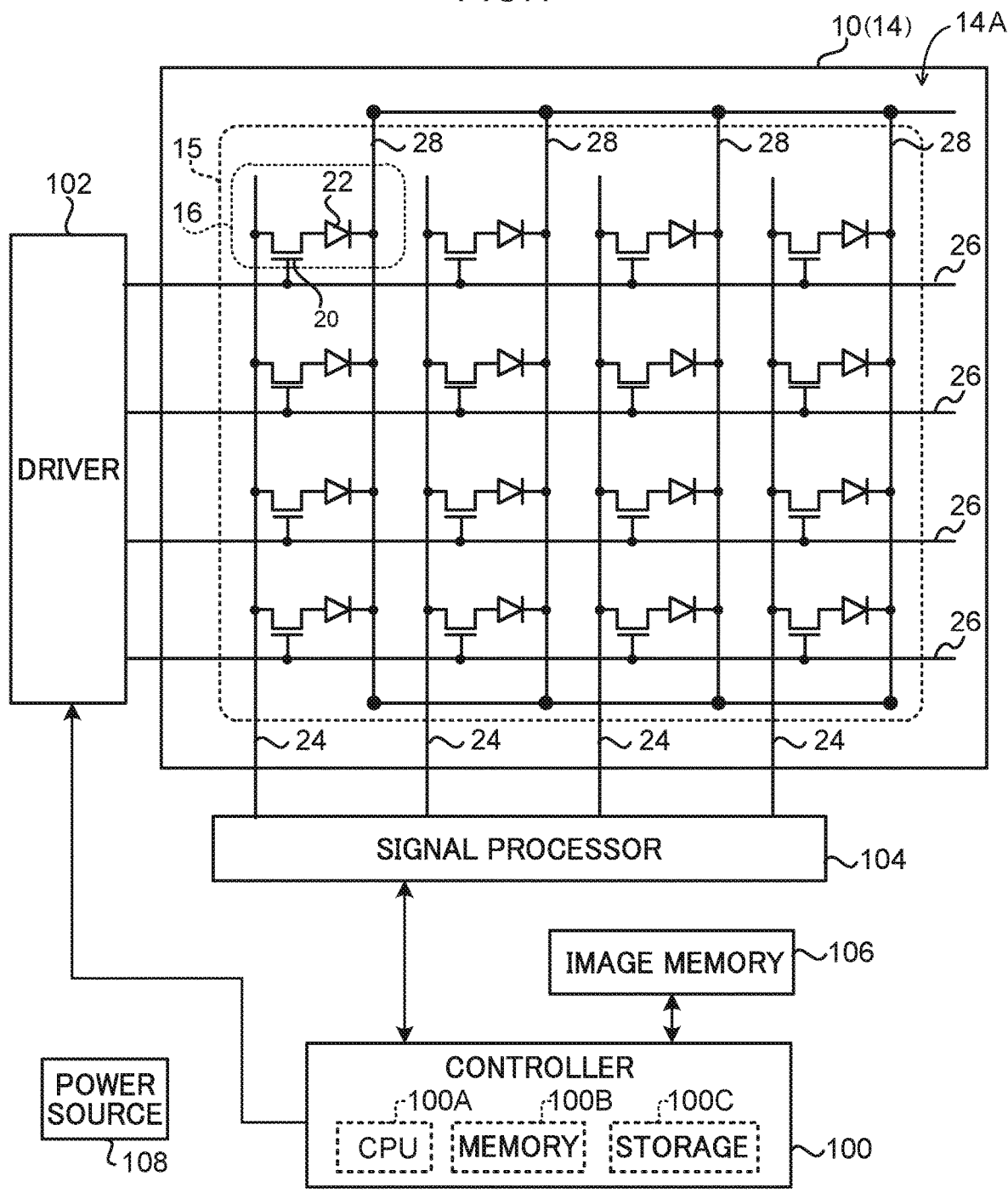
FIG. 1 is a block diagram illustrating an example of relevant configuration of an electrical system of a radiographic imaging device of a first exemplary embodiment.

First, basic explanation follows regarding an example of configuration of an electrical system of the radiographic imaging device of the present exemplary embodiment, with reference to FIG. 1. FIG. 1 is a block diagram illustrating an example of relevant configuration of the electrical system of the radiographic imaging device of the present exemplary embodiment.

As illustrated in FIG. 1, a radiographic imaging device 1 of the present exemplary embodiment includes a radiation detector 10, a controller 100, a driver 102, a signal processor 104, an image memory 106, and a power source 108.

The radiation detector 10 includes a sensor substrate 12 (see FIG. 3) and a conversion layer 30 (see FIG. 3) to convert radiation into light. The sensor substrate 12 includes a flexible base member 14 and plural pixels 16 provided on a first surface 14A of the base member 14. In the following explanation, the plural pixels 16 are also referred to simply as the "pixels 16".

As illustrated in FIG. 1, each of the pixels 16 of the present exemplary embodiment includes a sensor section 22 that accumulates an electrical charge generated in response to light converted by the conversion layer, and a switching element 20 that reads the accumulated electrical charge from the sensor section 22. As an example, in the present exemplary embodiment, a thin film transistor (TFT) is employed as the switching element 20. The switching element 20 is thus referred to as the TFT 20 hereafter. In the present exemplary embodiment, a layer in which the pixels 16 are formed is provided on the first surface 14A of the base member 14 as a flattened layer formed with the sensor sections 22 and the TFTs 20. Hereafter, the layer in which the pixels 16 are formed is sometimes referred to as the pixels 16 in the interests of simplicity.

The pixels 16 are arranged along one direction (a scan line direction corresponding to the lateral direction in FIG. 1, hereafter also referred to as the "row direction") and along a direction intersecting the row direction (a signal line direction corresponding to the longitudinal direction in FIG. 1, hereafter also referred to as the "column direction") to form a two-dimensional pattern in a pixel region 15 of the sensor substrate 12. Although the array of the pixels 16 is simplified in the illustration of FIG. 1, for example 1024× 1024 of the pixels 16 are arranged along the row direction and the column direction.

The radiation detector 10 is further provided with plural scan lines 26 corresponding to each row of the pixels 16 to control switching states (ON and OFF states) of the TFTs 20, and plural signal lines 24 that intersect the plural scan lines 26 and correspond to each column of the pixels 16 to read the accumulated electrical charges from the sensor sections 22. Each of the plural scan lines 26 is connected to the driver 102 through a pad (not illustrated in the drawings). The controller 100, described later, is connected to the driver 102 that outputs drive signals in response to control signals output from the controller 100. In the plural scan lines 26, drive signals output from the driver 102 to drive the TFTs 20 so as to control the switching states thereof flow through each of the plural scan lines. Each of the plural signal lines 24 is connected to the signal processor 104 through a pad (not illustrated in the drawings) so as to output electrical charges read from the respective pixels 16 to the signal processor 104 as electrical signals. The signal processor 104 generates and outputs image data in response to the input electrical signals.

The controller 100, described later, is connected to the signal processor 104, and the image data output from the signal processor 104 is sequentially output to the controller 100. The image memory 106 is connected to the controller 100, and the image data sequentially output from the signal processor 104 is sequentially stored in the image memory 106 under the control of the controller 100. The image memory 106 has a storage capacity capable of storing image data for a predetermined number of images, and each time radiographic imaging is performed, the image data obtained by this imaging is sequentially stored in the image memory 106.

The controller 100 includes a central processing unit (CPU) 100A, memory 100B including read only memory (ROM) and random access memory (RAM), and a non-volatile storage 100C configured by flash memory or the like. For example, a microcomputer may be applied as the controller 100. The controller 100 controls overall operation of the radiographic imaging device 1.

Common lines 28 are provided along the wiring direction of the signal lines 24 to the sensor sections 22 of the corresponding pixels 16 in order to apply a bias voltage to the corresponding pixels 16. Each of the common lines 28 is connected to a bias power source (not illustrated in the drawings) external to the sensor substrate 12 through a pad (not illustrated in the drawings), such that the bias voltage from the bias power source is applied to the corresponding pixels 16.

The power source 108 supplies electric power to the respective elements and respective circuitry of the controller 100, the driver 102, the signal processor 104, the image memory 106, and so on. Note that in FIG. 1, lines connecting the power source 108 to the respective elements and respective circuitry are omitted from illustration in the interests of avoiding complexity.

Figure 2A:
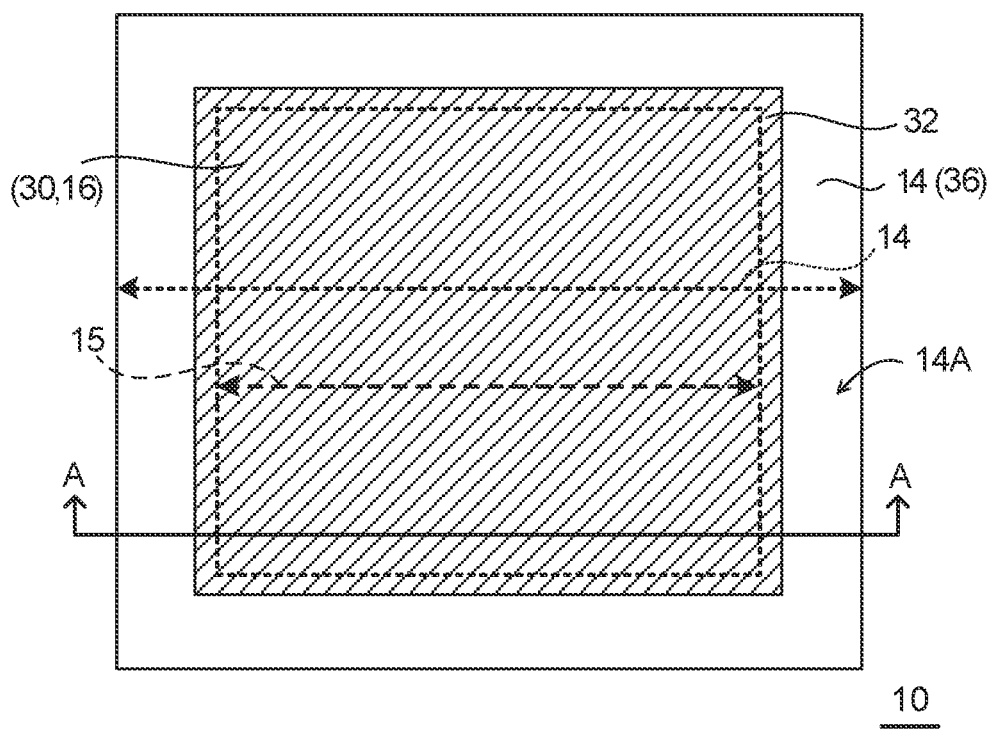
FIG. 2A is a plan view illustrating an example of a radiation detector of the first exemplary embodiment as viewed from a first surface side.
Figure 3:
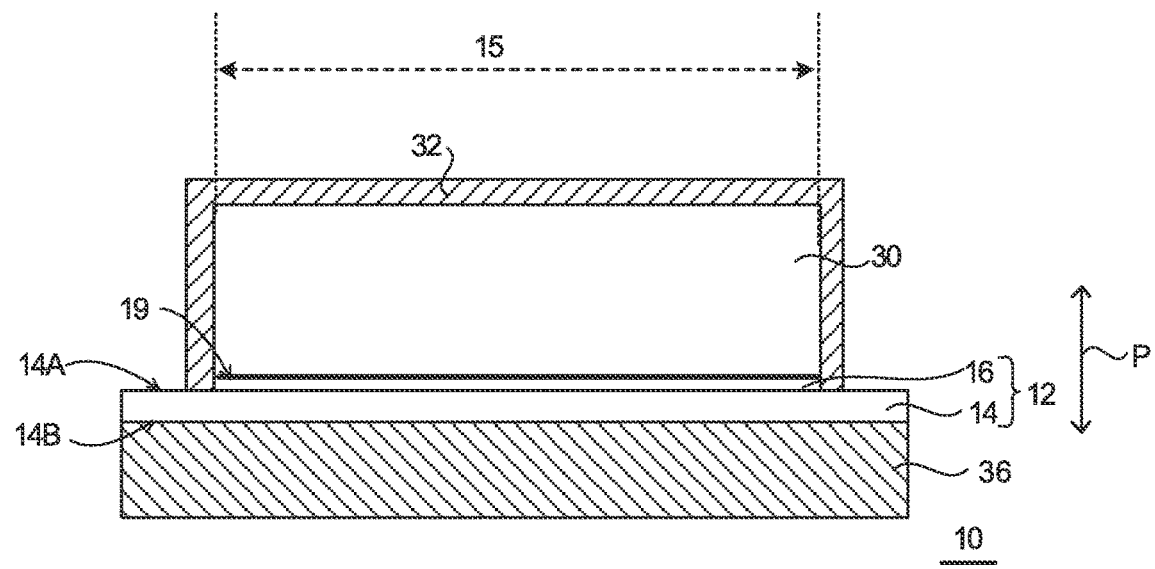
FIG. 3 is a cross-section of the radiation detector illustrated in FIG. 2A as sectioned along line A-A.

Detailed explanation follows regarding the radiation detector 10 of the present exemplary embodiment. FIG. 2A is a plan view illustrating the radiation detector 10 of the present exemplary embodiment from the first surface 14A side. FIG. 3 is a cross-section illustrating the radiation detector 10 as sectioned along line A-A in FIG. 2A.

As illustrated in FIG. 2A and FIG. 3, the radiation detector 10 of the present exemplary embodiment includes the sensor substrate 12 incorporating the base member 14 and the pixels 16, the conversion layer 30, and a protective film 32. The base member 14, the pixels 16, and the conversion layer 30 are provided in this sequence. Note that in the following explanation, the direction in which the base member 14, the pixels 16, and the conversion layer 30 are arranged (the up-down direction in FIG. 3) is referred to as the stacking direction (the stacking direction is labeled P; see FIG. 3). For ease of explanation, the side corresponding to the conversion layer 30 in the stacking direction P of the radiation detector 10 is also referred to as the upper side, and the side corresponding to the sensor substrate 12 is also referred to as the lower side.

The base member 14 is flexible, and is for example configured by a resin sheet containing plastic such as polyimide (PI). The thickness of the base member 14 may be any thickness that enables the desired flexibility to be obtained, set according to the hardness of the material and the size of the sensor substrate 12 (the area of the first surface 14A or a second surface 14B). For example, in a state in which the rectangular base member 14 is taken on its own and one edge of the base member 14 is fixed, having flexibility means that the base member 14 will droop (drop to a lower height than the fixed edge) due to gravity by at least 2 mm under the weight of the base member 14 itself at a position 10 cm from the fixed edge. As a specific example, a resin sheet configuring the base member 14 preferably has a thickness of from 5 µm to 125 µm, and more preferably has a thickness of from 20 µm to 50 µm.

Note that the base member 14 has characteristics capable of withstanding manufacture of the pixels 16, as will be described in detail later, and in the present exemplary embodiment, has characteristics capable of withstanding the manufacture of amorphous silicon TFTs (a-Si TFTs). Preferable characteristics of the base member 14 are a coefficient of thermal expansion (CTE) in a range of from 300° C. to 400° C. that is similar to that of an amorphous silicon (Si) wafer (for example ±5 ppm/K), and more specifically preferably no greater than 20 ppm/K. The heat shrinkage ratio of the base member 14 in a machine direction at 400° C. and at a thickness of 25 µm is preferably a heat shrinkage ratio of not greater than 0.5%. Moreover, the modulus of elasticity of the base member 14 preferably does not have a transition point in a temperature region of from 300° C. to 400° C., as is typical of an ordinary polyimide, and preferably has a modulus of elasticity at 500° C. of not less than 1 GPa.

Figure 2B:
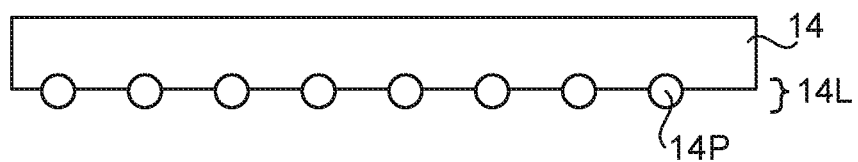
FIG. 2B is a cross-section to explain an example of a base member.
Figure 2C:
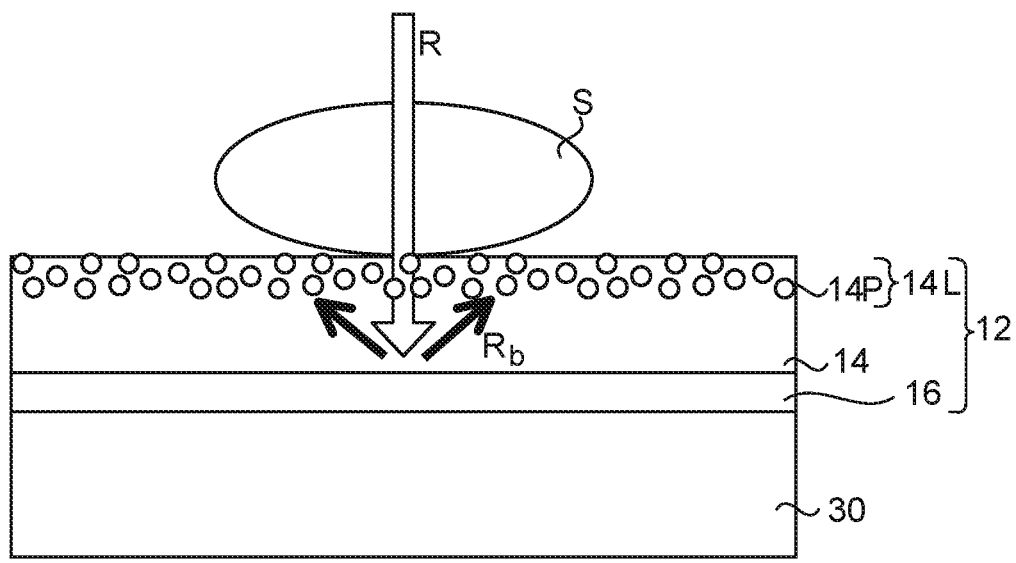
FIG. 2C is an explanatory diagram to explain backscattered radiation generated within a base member including a fine particle layer by radiation that has passed through an imaging subject.

Moreover, as illustrated in FIG. 2B and FIG. 2C, the base member 14 of the present exemplary embodiment preferably includes a fine particle layer 14L containing inorganic fine particles 14P having a mean particle size of from 0.05 µm to 2.5 µm. Note that FIG. 2C illustrates an example of a case in which the radiation detector 10 of the present exemplary embodiment is applied as a radiation detector employing an irradiation side sampling (ISS) approach in which radiation R is irradiated from the sensor substrate 12 side.

Figure 2D:
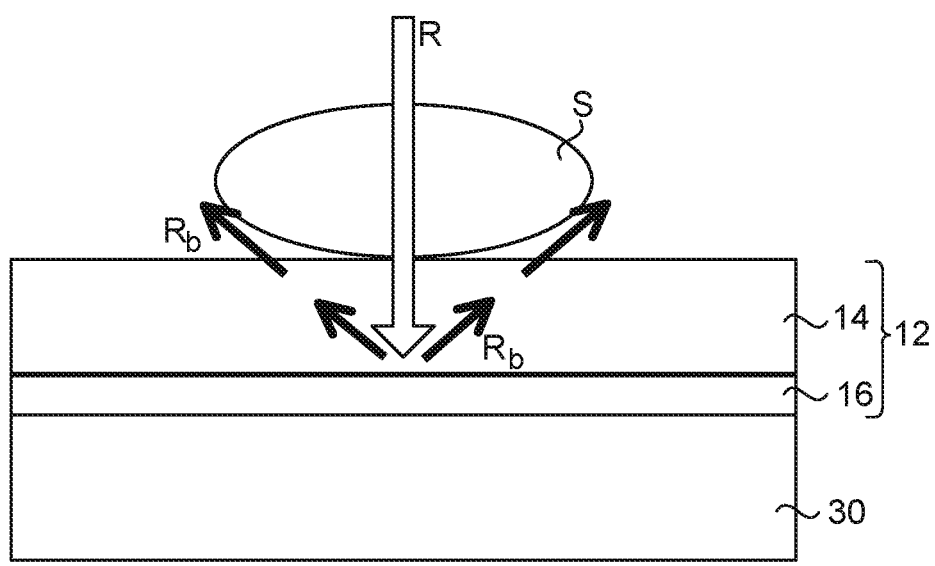
FIG. 2D is an explanatory diagram to explain backscattered radiation generated within a base member not including a fine particle layer by radiation that has passed through an imaging subject.

As illustrated in FIG. 2C and FIG. 2D, the radiation R that has passed through an imaging subject S causes back-scattered radiation Rb in the base member 14. In cases in which the base member 14 is configured from a resin such as a PI, this being an organic material, the back-scattered radiation Rb of atoms of C, H, O, N and the like configuring the organic material and that have comparatively small atomic numbers increases due to the Compton effect.

As illustrated in FIG. 2C, in cases in which the base member 14 includes the fine particle layer 14L containing the fine particles 14P to absorb the back-scattered radiation Rb arising in the base member 14, then as illustrated in FIG. 2D, the back-scattered radiation Rb that has passed through the base member 14 and been scattered at the back of the base member 14 is suppressed in comparison to cases in which the base member 14 does not include the fine particle layer 14L. Including the fine particle layer 14L is thus preferable.

The fine particles 14P are preferably configured by an inorganic material containing atoms that cause little back-scattered radiation Rb in their own right, that absorb the back-scattered radiation Rb, and that absorb little of the radiation R that has passed through the imaging subject S. Note that there is a trade-off relationship between suppressing back-scattered radiation Rb and allowing the radiation R to pass through. From the perspective of suppressing the back-scattered radiation Rb, the fine particles 14P preferably include elements having atomic numbers greater than those of the C, H, O, N, and the like configuring the resin of the base member 14. Although the ability to absorb the back-scattered radiation Rb increases the greater the atomic number, if the atomic number exceeds 30, the amount of radiation R absorbed increases, and there is a marked decrease in the amount of radiation R that reaches the conversion layer 30, and so this is not preferable. Accordingly, in cases in which the base member 14 is made of resin, an inorganic material that has an atomic number greater than the atoms configuring the organic material that is the base member 14, but does not exceed 30, is preferably employed as the fine particles 14P. Specific examples of such fine particles 14P include $SiO_2$ that is an oxide of silicon having the atomic number 14, MgO that is an oxide of Mg having the atomic number 12, $Al_2O_3$ that is an oxide of Al having the atomic number 13, and $TiO_2$ that is an oxide of Ti having the atomic number 22.

XENOMAX (registered trademark) is a specific example of a resin sheet having the characteristics listed above.

Note that in the present exemplary embodiment, the thickness is measured using a micrometer. The coefficient of thermal expansion is measured according to JIS K7197:1991. In this measurement, test pieces are cut from a main face of the base member 14 while changing the angle thereof by 15 degrees each time, the coefficient of thermal expansion is measured for each of the cut test pieces, and the highest value obtained is taken to be the coefficient of thermal expansion of the base member 14. The measurements of the coefficient of thermal expansion in the machine direction (MD) and a transverse direction (TD) are performed at 10° C. intervals over a range of from −50° C. to 450° C. with ppm/° C. converted into ppm/K. A TMA4000S instrument made by MAC Science Co., Ltd. is employed to measure the coefficient of thermal expansion using a sample length of 10 mm, a sample width of 2 mm, an initial load of 34.5 g/mm$^2$, a rate of temperature increase of 5° C./min, and an argon atmosphere. The modulus of elasticity is measured according to JIS K7171:2016. Note that in this measurement, test pieces are cut from a main face of the base member 14 while changing the angle thereof by 15 degrees each time, a stretch test is performed on each of the cut test pieces, and the highest value obtained is taken to be the modulus of elasticity of the base member 14.

Note that unevenness may arise on the front surface of the base member 14 due to the fine particles 14P contained in the fine particle layer 14L. Formation of the pixels 16 sometimes becomes difficult in a state in which such unevenness has arisen on the front surface of the base member 14. Accordingly, as illustrated in FIG. 2C, the fine particle layer 14L is preferably included on the second surface 14B on the opposite side of the base member 14 to the first surface on which the pixels 16 are formed, namely on the second surface 14B on the opposite side to the first surface where the conversion layer 30 is provided.

In order to sufficiently absorb the back-scattered radiation Rb arising in the base member 14, the fine particle layer 14L is preferably included on the side of the surface of the base member 14 that is closer to the imaging subject S. As illustrated in FIG. 2C, in the ISS-approach radiation detector 10, the fine particle layer 14L is preferably included on the second surface 14B.

Thus, in the ISS-approach radiation detector 10, the base member 14 includes the fine particle layer 14L on the second surface 14B, enabling the pixels 16 to be formed with good precision, and enabling back-scattered radiation Rb to be effectively suppressed.

Note that there is no limitation to manufacturing the base member 14 from a resin object such as a resin sheet in order to achieve the desired flexibility. For example, the base member 14 may be a glass substrate with a comparatively thin thickness. As a specific example of a case in which the base member 14 is a glass substrate, for a size having an edge length in the region of 43 cm, a glass substrate will generally be flexible at a thickness of no greater than 0.3 mm. Accordingly, a glass substrate may be employed as desired as long as the thickness is no greater than 0.3 mm.

As illustrated in FIG. 2A and FIG. 3, the plural pixels 16 are provided in a region corresponding to a portion at an inner side of the first surface 14A of the base member 14. In other words, in the sensor substrate 12 of the present exemplary embodiment, the pixels 16 are not provided at an outer peripheral portion of the first surface 14A of the base member 14. In the present exemplary embodiment, the region of the first surface 14A of the base member 14 provided with the pixels 16 is referred to as the pixel region 15.

As illustrated in FIG. 3, the conversion layer 30 of the present exemplary embodiment covers the pixel region 15. In the present exemplary embodiment, a scintillator containing cesium iodide (CsI) is employed as an example of the conversion layer 30. For example, the scintillator preferably contains thallium-doped cesium iodide (CsI:Tl) or sodium-doped cesium iodide (CsI:Na) that has light emission spectra of from 400 nm to 700 nm when irradiated with X-rays. Note that the peak light emission wavelength of CsI:Tl in the visible light region is 565 nm.

As illustrated in FIG. 2A and FIG. 3, in the radiation detector 10 of the present exemplary embodiment, the protective film 32 is provided on the first surface 14A side of the base member 14 so as to cover the entirety of a stacked body configured by stacking the pixels 16 and the conversion layer 30. Specifically, the protective film 32 covers the entire surface of the stacked body configured by stacking the pixels 16 and the conversion layer 30 except for a face contacting the first surface 14A of the base member 14.

The protective film 32 may be configured by a moisture-proof film such as an insulating sheet such as Parylene (registered trademark) or polyethylene terephthalate, or an ALPET (registered trademark) sheet in which an aluminum layer such as an aluminum foil is bonded to an insulating sheet (film).

As illustrated in FIG. 2A and FIG. 3, the radiation detector 10 of the present exemplary embodiment is provided with a neutral stress plane adjustment member 36 on the second surface 14B of the base member 14. The neutral stress plane adjustment member 36 adjusts the position of a neutral stress plane (described in detail later) of the radiation detector 10 with respect to the stacking direction P during bending of the radiation detector 10. As an example, polyethylene terephthalate (PET) is employed as the neutral stress plane adjustment member 36 in the present exemplary embodiment, but white PET or foamed white PET may also be employed. White PET is PET to which a white pigment, such as $TiO_2$, barium sulfate, or the like, has been added. Foamed white PET is white PET having a porous surface. Other examples of the neutral stress plane adjustment member 36 include organic films of polycarbonate (PC), low density polyethylene (LDPE), polyphenylene sulfide (PPS), oriented polypropylene (OPP), polyethylene naphthalate (PEN), and PI.

The neutral stress plane adjustment member 36 of the present exemplary embodiment preferably employs a material having a bending elastic modulus of from 150 MPa to 2500 MPa. The bending elastic modulus is for example measured according to JIS K7171:2016. The neutral stress plane adjustment member 36 preferably has higher bending rigidity than the base member 14 from the perspective of suppressing bending of the base member 14. Note that the bending rigidity becomes lower the lower the bending elastic modulus, and the thickness of the neutral stress plane adjustment member 36 has to be increased in order to obtain the desired bending rigidity, thus increasing the overall thickness of the radiation detector 10. Considering the above-mentioned materials that may be employed for the neutral stress plane adjustment member 36, the thickness of the neutral stress plane adjustment member 36 tends to become comparatively thick if attempting to obtain bending rigidity in excess of 140,000 $Pacm^4$. Accordingly, in consideration of obtaining the appropriate rigidity and also of the thickness of the overall radiation detector 10, the material employed for the neutral stress plane adjustment member 36 preferably has a bending elastic modulus of from 150 MPa to 2500 MPa. The bending rigidity of the neutral stress plane adjustment member 36 is preferably from 540 $Pacm^4$ to 140,000 $Pacm^4$.

The coefficient of thermal expansion of the neutral stress plane adjustment member 36 of the present exemplary embodiment is preferably close to the coefficient of thermal expansion of the material of the conversion layer 30, and more preferably the ratio of the coefficient of thermal expansion of the neutral stress plane adjustment member 36 with respect to the coefficient of thermal expansion of the conversion layer 30 (the coefficient of thermal expansion of the neutral stress plane adjustment member 36 divided by the coefficient of thermal expansion of the conversion layer 30) is from 0.5 to 4. The coefficient of thermal expansion of the neutral stress plane adjustment member 36 is preferably from 30 ppm/K to 200 ppm/K. For example, in cases in which CsI:Tl is employed as the material of the conversion layer 30, the coefficient of thermal expansion thereof is 50 ppm/K. In such cases, examples of materials that may be employed for the neutral stress plane adjustment member 36 include LDPE with a coefficient of thermal expansion of from 100 ppm/K to 200 ppm/K, polyvinyl chloride (PVC) with a coefficient of thermal expansion of from 60 ppm/K to 80 ppm/K, acrylic with a coefficient of thermal expansion of from 70 ppm/K to 80 ppm/K, PET with a coefficient of thermal expansion of from 65 ppm/K to 70 ppm/K, PC with a coefficient of thermal expansion of 65 ppm/K, and TEFLON (registered trademark) with a coefficient of thermal expansion of from 45 ppm/K to 70 ppm/K.

In consideration of the bending elastic modulus mentioned above, the material of the neutral stress plane adjustment member 36 preferably contains at least out of PET, PC, and LDPE.

Note that the neutral stress plane adjustment member 36 has a function of adjusting the position of the neutral stress plane, and also preferably includes other functions such as an anti-static function and a moisture-proofing function.

Figure 4:
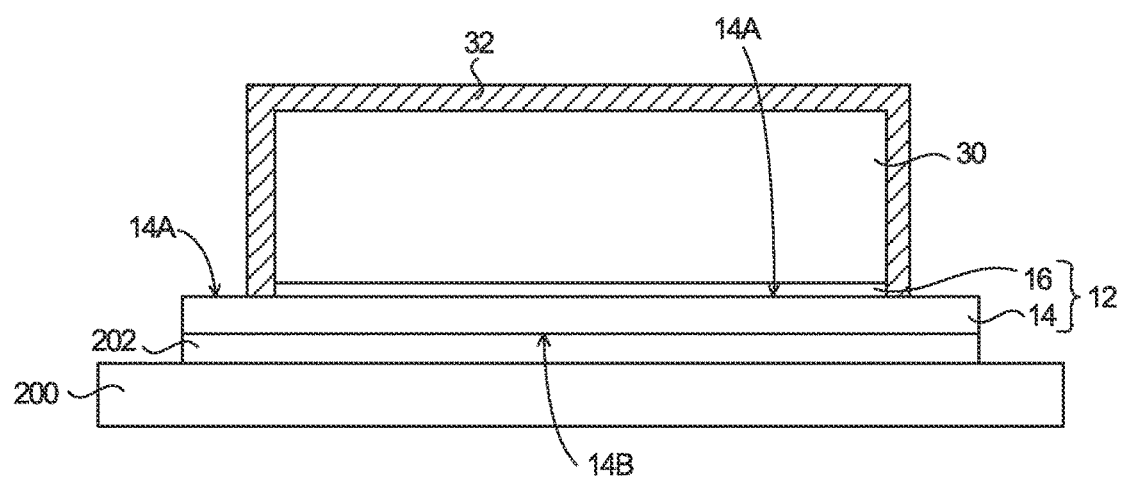
FIG. 4 is an explanatory diagram to explain a manufacturing method of the radiation detector illustrated in FIG. 2A and FIG. 3.

Explanation follows regarding a manufacturing method of the radiation detector 10 provided with the sensor substrate 12 employing the flexible base member 14, as in the radiation detector 10 illustrated in FIG. 2A and FIG. 3, with reference to FIG. 4.

As illustrated in FIG. 4, the base member 14 is formed on a support body 200 such as a glass substrate with a greater thickness than the base member 14 with a detachment layer 202 interposed therebetween. In cases in which the base member 14 is formed by a lamination method, a sheet configuring the base member 14 is stuck onto the support body 200. The second surface 14B of the base member 14 contacts the detachment layer 202.

The pixels 16 are then formed on the first surface 14A of the base member 14. Note that as an example, in the present exemplary embodiment, the pixels 16 are formed on the first surface 14A of the base member 14 with an undercoat layer (not illustrated in the drawings) employing SiN or the like interposed therebetween.

The conversion layer 30 is formed over the layer formed with the pixels 16 (hereafter simply referred to as the pixels 16). In the present exemplary embodiment, the conversion layer 30 is configured by columnar crystals of CsI formed directly to the sensor substrate 12 using a vapor phase deposition method such as a vacuum deposition method, a sputtering method, or a chemical vapor deposition (CVD) method. When this is performed, the side of the conversion layer 30 contacting the pixels 16 corresponds to the start side in the growth direction of the columnar crystals.

Note that in cases in which the CsI conversion layer 30 is directly provided on the sensor substrate 12 using a vapor phase deposition method in this manner, the face of the conversion layer 30 on the opposite side to the side contacting the sensor substrate 12 may, for example, be provided with a reflective layer (not illustrated in the drawings) having a function of reflecting light converted by the conversion layer 30. Such a reflective layer may be directly provided to the conversion layer 30, or may be provided with a cohesion layer or the like interposed therebetween. An organic material is preferably employed as the material of the reflective layer, and for example a material employing at least one material out of white PET, TiO$_2$, Al$_2$O$_3$, foamed white PET, a highly reflective polyester sheet, or a specular reflective aluminum is preferably employed. In particular, from the perspective of reflectivity, a white PET material is preferably employed. Note that a highly reflective polyester sheet is a sheet (film) having a multi-layered structure of plural overlapping thin polyester sheets.

In cases in which a CsI scintillator is employed as the conversion layer 30, the conversion layer 30 may be formed on the sensor substrate 12 using a different method to that of the present exemplary embodiment. For example, vapor deposition of CsI on an aluminum sheet or the like may be performed using a vapor phase deposition method, and the conversion layer 30 may be formed on the sensor substrate 12 by sticking the side of the CsI that does not contact the aluminum sheet and the pixels 16 of the sensor substrate 12 together using an adhesive sheet or the like. In such cases, a product of covering the overall conversion layer 30 including the aluminum sheet with the protective film 32 is preferably stuck to the pixels 16 of the sensor substrate 12. Note that in such cases, the side of the conversion layer 30 contacting the pixels 16 configures a growth direction tip end side of the columnar crystals.

Unlike the radiation detector 10 of the present exemplary embodiment, GOS (Gd$_2$O$_2$S:Tb) or the like may be employed in place of CsI as the conversion layer 30. In such cases, a sheet on which GOS has been distributed using a resin binder or the like may be stuck to a support body formed from white PET or the like using an adhesion layer or the like, and the side of the GOS that is not stuck to the support body may be stuck to the pixels 16 of the sensor substrate 12 using an adhesive sheet or the like to form the conversion layer 30 on the sensor substrate 12. Note that the efficiency of radiation to visible light conversion is greater when CsI is employed than when GOS is employed for the conversion layer 30.

In the radiation detector 10 of the present exemplary embodiment, the protective film 32 is formed on the sensor substrate 12 provided with the conversion layer 30 so as to cover the entire region of the stacked body configured by stacking the pixels 16 and the conversion layer 30, to give the state illustrated in FIG. 4.

The sensor substrate 12 provided with the conversion layer 30 and the protective film 32 is then detached from the support body 200. For example, in the lamination method, detachment is performed mechanically by starting detachment at any of the four edges of the sensor substrate 12 (base member 14) and gradually peeling the sensor substrate 12 away from the support body 200 toward the edge opposing the start edge.

In the present exemplary embodiment, after the sensor substrate 12 has been detached from the support body 200, the neutral stress plane adjustment member 36 is formed on, the second surface 14B of the base member 14, for example by being stuck thereto.

Figure 5:
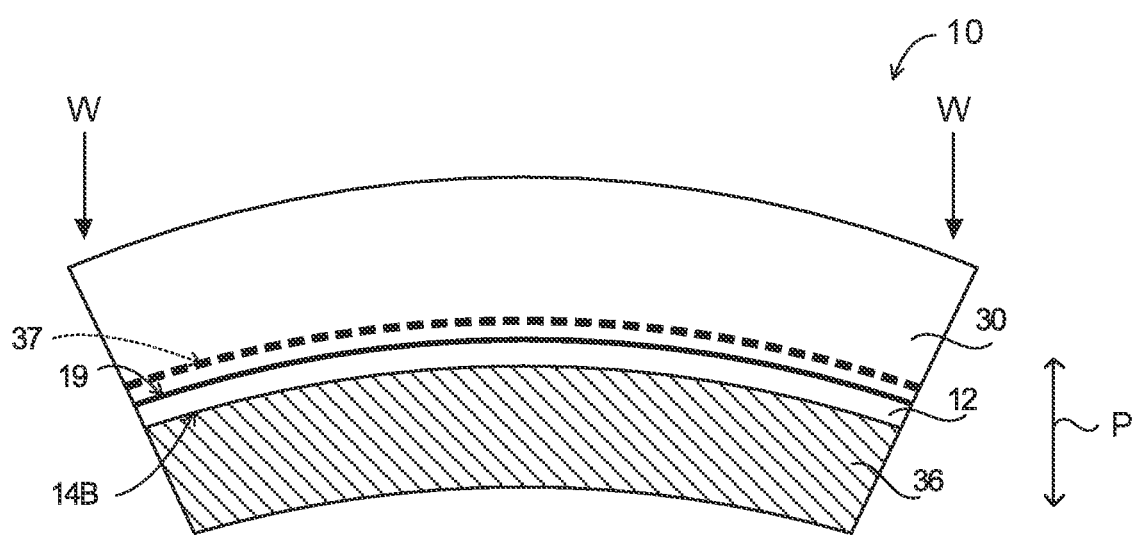
FIG. 5 is a schematic diagram illustrating an example of a state in which a radiation detector has bent under load applied in a layer stacking direction.

Explanation follows regarding operation of the neutral stress plane adjustment member 36 of the radiation detector 10 of the present exemplary embodiment, with reference to FIG. 5 and FIG. 6A to FIG. 6C. The neutral stress plane adjustment member 36 adjusts the position with respect to the stacking direction P of a neutral stress plane 37 that manifests when the radiation detector 10 is bent due to application of a load W in the stacking direction P. FIG. 5 schematically illustrates an example of a state in which the radiation detector 10 has been bent by application of the load W in the stacking direction P. Note that in the interests of simplicity, only the sensor substrate 12, the conversion layer 30, and the neutral stress plane adjustment member 36 of the radiation detector 10 are schematically illustrated in FIG. 5.

FIG. 5 illustrates a state in which the conversion layer 30 side has stretched and the sensor substrate 12 (neutral stress plane adjustment member 36) side has been compressed as an example of a bent state of the radiation detector 10. In this case, the neutral stress plane 37 configuring a plane (a plane in a direction intersecting the stacking direction P) where the radiation detector 10 is neither stretched nor compressed despite being bent manifests within the radiation detector 10. Stress is zero within the neutral stress plane 37.

When the radiation detector 10 bends, stress acts on an interface 19 between the sensor substrate 12 and the conversion layer 30, such that the conversion layer 30 is more likely to detach from the sensor substrate 12. Note that in the present exemplary embodiment, the "interface" refers to a face of the conversion layer 30 that opposes the sensor substrate 12.

Figure 6A:
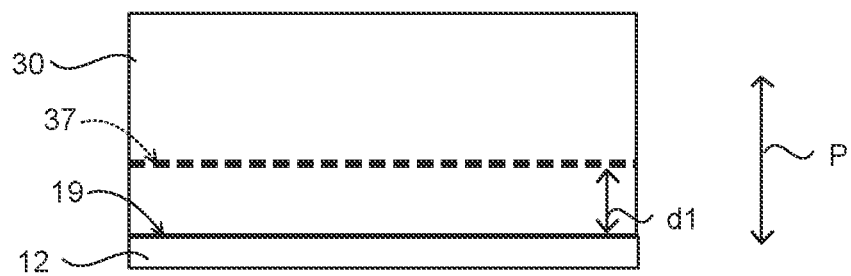
FIG. 6A is a schematic diagram to explain operation of a neutral stress plane adjustment member.

If the neutral stress plane adjustment member 36 were not provided, since the conversion layer 30 is thicker than the sensor substrate 12, the position of the neutral stress plane 37 would generally be positioned on the conversion layer 30 side (the stacking direction P upper side) of the interface 19 as illustrated in FIG. 6A. In the case illustrated in FIG. 6A, the stress acting on the interface 19 makes the conversion layer 30 more likely to detach from the sensor substrate 12.

Figure 6B:
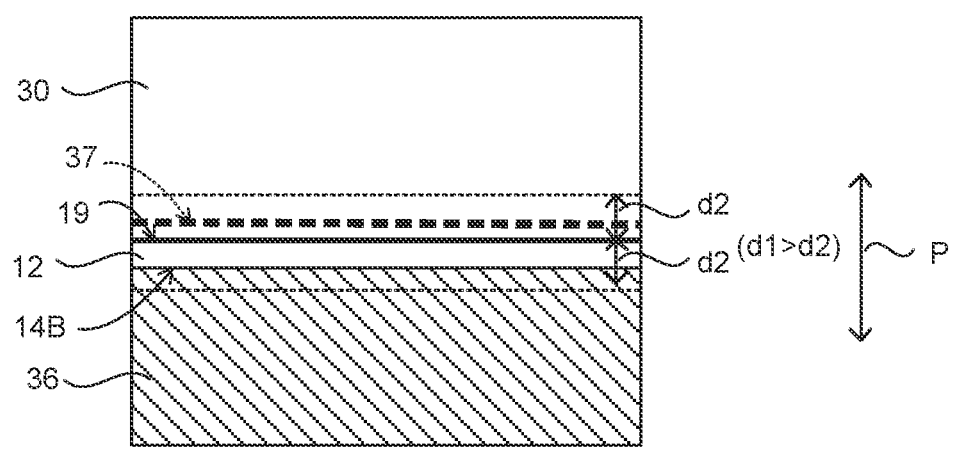
FIG. 6B is a schematic diagram to explain operation of a neutral stress plane adjustment member.

In cases in which the neutral stress plane adjustment member 36 is provided on the sensor substrate 12 side as in the radiation detector 10 of the present exemplary embodiment, the position of the neutral stress plane 37 moves further toward the sensor substrate 12 side than in cases in which the neutral stress plane adjustment member 36 is not provided. Accordingly, as illustrated in FIG. 6B, the position of the neutral stress plane 37 can be set in the vicinity of the interface 19. Specifically, if a distance between the interface 19 and the neutral stress plane 37 in a case in which the neutral stress plane adjustment member 36 is not provided as illustrated in FIG. 6A is denoted d1, and a distance between the interface 19 and the neutral stress plane 37 in a case in which the neutral stress plane adjustment member 36 is provided as illustrated in FIG. 6B is denoted d2, then the distance d2 can be made smaller than the distance d1 (d1>d2).

Figure 6C:
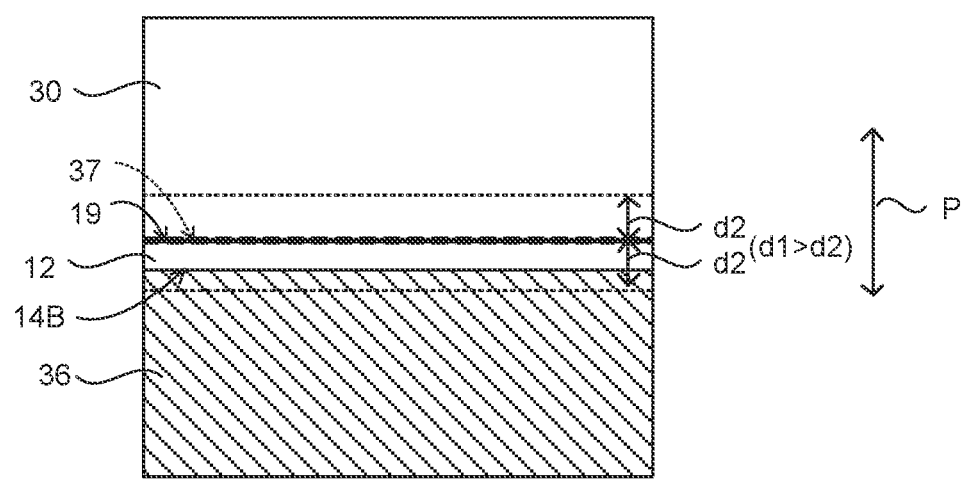
FIG. 6C is a schematic diagram to explain operation of a neutral stress plane adjustment member.

Regarding the position of the neutral stress plane 37, the position of the neutral stress plane 37 is preferably aligned with the position of the interface 19 as illustrated in FIG. 6C. In such cases, stress at the interface 19 can be set to zero, making the conversion layer 30 less likely to detach from the sensor substrate 12.

In the radiation detector 10 of the present exemplary embodiment, providing the neutral stress plane adjustment member 36 to the second surface 14B of the base member 14 of the sensor substrate 12 enables the position of the neutral stress plane 37 that manifests in the radiation detector 10 to be adjusted to within a range of less than the distance d1 from the interface 19. Regarding the position of the neutral stress plane 37, in the present exemplary embodiment, the range that is less than the distance d1 from the interface 19 configures a permissible range of the position of the neutral stress plane 37. The radiation detector 10 of the present exemplary embodiment thereby enables stress arising at the interface 19 to be brought close to zero during bending of the radiation detector 10, thus making the conversion layer 30 less likely to detach from the sensor substrate 12. Note that in the present exemplary embodiment, the range that is less than the distance d1 from the interface 19 is an example of a predetermined range of the present disclosure.

Note that the thickness of the neutral stress plane 37 is prescribed according to the permissible range of the position of the neutral stress plane 37 from the interface 19 (permissible range, permissible range <2d1). The specific thickness of the neutral stress plane 37 is prescribed according to the degree of cohesion (ease of detachment) between the sensor substrate 12 and the conversion layer 30, the anticipated degree of bending, and the like. For example, in cases in which the conversion layer 30 is directly formed on the sensor substrate 12 by vapor deposition, the conversion layer 30 is more likely to detach than in cases in which a separately formed conversion layer 30 is stuck on, and so the thickness of the neutral stress plane adjustment member 36 is preferably greater in cases in which the conversion layer 30 is formed directly to the sensor substrate 12 by vapor deposition than in cases in which the conversion layer 30 is stuck to the sensor substrate 12.

Next, explanation follows regarding the radiographic imaging device 1 applied with the radiation detector 10 of the present exemplary embodiment. In the radiographic imaging device 1, the radiation detector 10 is provided inside a case that allows radiation to pass through, that is waterproof, antibacterial, and tightly sealed.

Figure 7:
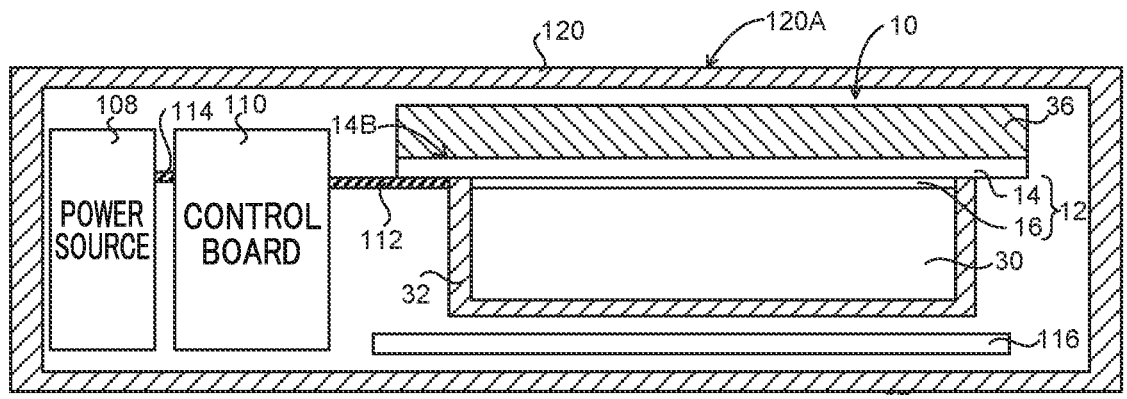
FIG. 7 is a cross-section illustrating an example of a state in which a radiation detector is provided inside a case in a case in which an irradiation side sampling (ISS) approach is adopted for a radiographic imaging device of an exemplary embodiment.

FIG. 7 illustrates an example of a state in which the radiation detector 10 is provided inside a case 120 in a case in which an ISS approach is applied in the radiographic imaging device 1 of the present exemplary embodiment.

As illustrated in FIG. 7, the radiation detector 10, the power source 108, and a control board 110 are provided arranged inside the case 120 in a direction intersecting the stacking direction P. In the radiation detector 10, the second surface 14B of the base member 14 is provided so as to oppose an imaging face 120A, configuring an irradiated face that is irradiated with radiation, of the case 120 that is irradiated with radiation that has passed through the imaging subject.

The control board 110 is a substrate on which the image memory 106, the controller 100, and so on are formed, and is electrically connected to the pixels 16 of the sensor substrate 12 by a flexible cable 112 including plural signal lines. Note that in the present exemplary embodiment, the driver 102 and the signal processor 104 are provided on the flexible cable 112 as what is known as a chip-on-film (COF). However, at least one out of the driver 102 or the signal processor 104 may be formed on the control board 110.

The control board 110 and the power source 108 are connected together by a power source line 114.

The case 120 is preferably lightweight, has a low absorption ratio of the radiation R, in particular X-rays, and high rigidity, and is preferably configured from a material that has a sufficiently high elastic modulus. A material having a bending elastic modulus of at least 10,000 MPa is preferably employed as the material of the case 120. Examples of materials suitably employed as the material of the case 120 include carbon or carbon fiber reinforced plastic (CFRP) having a bending elastic modulus of around 20,000 MPa to 60,000 MPa.

During capture of radiographic images by the radiographic imaging device 1, a load is applied to the imaging face 120A of the case 120 from the imaging subject. If the rigidity of the case 120 were insufficient, the load from the imaging subject would cause the sensor substrate 12 to bend, and there would be a concern of faults occurring such as damage to the pixels 16. Housing the radiation detector 10 is housed inside the case 120 configured from a material having a bending elastic modulus of at least 10,000 MPa enables bending of the sensor substrate 12 due to the load from the imaging subject to be suppressed.

A sheet 116 is provided inside the case 120 of the radiographic imaging device 1 of the present exemplary embodiment on the side where radiation that has passed through the radiation detector 10 is emitted. The sheet 116 may, for example, be a copper sheet. A copper sheet does not readily generate secondary radiation from incident radiation, and thus has a function of preventing scattering toward the rear, namely toward the conversion layer 30 side. Note that the sheet 116 at least covers the entire face on the radiation emission side of the conversion layer 30 and preferably covers the entire conversion layer 30, and more preferably covers the entire protective film 32. Note that the thickness of the sheet 116 may be selected according to the flexibility, weight, and the like of the entire radiographic imaging device 1. For example, in cases in which the sheet 116 is a copper sheet, the sheet 116 is flexible at a thickness of around 0.1 mm or greater, and also has a function of blocking secondary radiation that has penetrated inside the radiographic imaging device 1 from the exterior. As another example, in cases in which the sheet 116 is a copper sheet, 0.3 mm or lower is preferable from the perspective of flexibility and weight.

The radiographic imaging device 1 illustrated in FIG. 7 is capable of capturing radiographic images in a state in which the radiation detector 10 has been bent in a direction out of the plane of the second surface 14B of the base member 14. For example, radiographic images can be captured while a bent state of the radiation detector 10 persists as a result of an imaging site of the imaging subject.

In the radiographic imaging device 1 illustrated in FIG. 7, the power source 108 and the control board 110 are provided in a peripheral portion of the case 120 that has relatively high rigidity. This enables the application of external force to be suppressed from affecting the power source 108 and the control board 110.

Note that FIG. 7 illustrates an embodiment in which both the power source 108 and the control board 110 are provided on one side of the radiation detector 10, specifically, on the side of one edge of the rectangular radiation detector 10. However, there is no limitation to embodiments in which the power source 108 and the control board 110 are provided at the positions illustrated in FIG. 7. For example, the power source 108 and the control board 110 may be provided distributed between two opposing edges of the radiation detector 10, or may be provided distributed between two adjacent edges of the radiation detector 10. Moreover, FIG. 7 illustrates an embodiment in which the power source 108 and the control board 110 of the present exemplary embodiment are both singular configuration sections (substrates). However, there is no limitation to the embodiment illustrated in FIG. 7, and at least one out of the power source 108 or the control board 110 may be configured by plural configuration sections (substrates). For example, the power source 108 may include a first power source and a second power source (neither of which are illustrated), and the first power source and the second power source may be provided distributed between two opposing edges of the radiation detector 10.

Note that in cases in which a radiographic image is captured while the overall radiographic imaging device 1 (radiation detector 10) is bent, the effects of this bending on the image can be suppressed by performing image correction.

Figure 8:
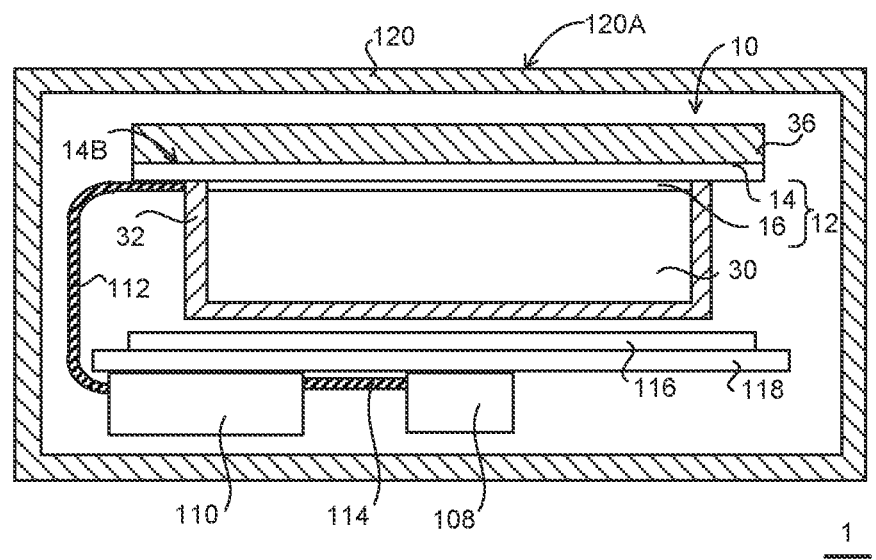
FIG. 8 is a cross-section illustrating another example of a state in which a radiation detector is provided inside a case in a case in which an ISS approach is applied for a radiographic imaging device of an exemplary embodiment.

FIG. 8 illustrates another example of a state in which the radiation detector 10 is provided inside the case 120, in a case in which an ISS approach is applied in the radiographic imaging device 1 of the present exemplary embodiment.

As illustrated in FIG. 8, the power source 108 and the control board 110 are provided arranged inside the case 120 in a direction intersecting the stacking direction P, and the radiation detector 10 and the power source 108 and control board 110 are provided arranged inside the case 120 along the stacking direction P.

In the radiographic imaging device 1 illustrated in FIG. 8, a base 118 is provided between the control board 110 and the power source 108 and sheet 116 to support the radiation detector 10 and the control board 110. For example, carbon or the like is employed for the base 118.

The radiographic imaging device 1 illustrated in FIG. 8 is capable of capturing radiographic images in a state in which the radiation detector 10 has been bent slightly in a direction out of the plane of the second surface 14B of the base member 14, for example in a state in which a central portion of the radiation detector 10 has been bent by around 1 mm to 5 mm. The control board 110 and power source 108 and the radiation detector 10 are provided along the stacking direction P, and bending is less pronounced than in the radiographic imaging device 1 illustrated in FIG. 7 due to providing the base 118. Stress arising due to bending is thus lower than in the radiographic imaging device 1 illustrated in FIG. 7, and the conversion layer 30 is less likely to detach from the sensor substrate 12. The thickness of the neutral stress plane adjustment member 36 can accordingly be reduced.

Second Exemplary Embodiment

In a radiation detector 10 of the present exemplary embodiment, the configuration of the neutral stress plane adjustment member 36 differs from that of the radiation detector 10 of the first exemplary embodiment. The first exemplary embodiment describes an embodiment in which the neutral stress plane adjustment member 36 is configured by a single film (layer). By contrast, in the present exemplary embodiment, an embodiment is described in which a neutral stress plane adjustment member 36 has a stacked configuration in which plural films are stacked.

Figure 9:
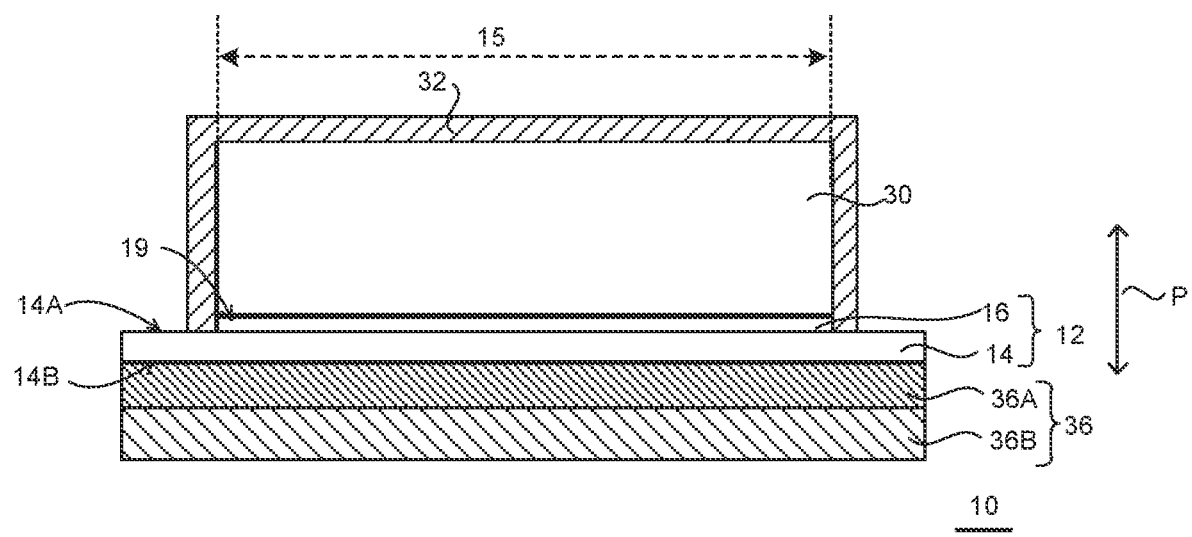
FIG. 9 is a cross-section illustrating an example of a radiation detector of a second exemplary embodiment.

FIG. 9 is a cross-section illustrating an example of the radiation detector 10 of the present exemplary embodiment. As illustrated in FIG. 9, the neutral stress plane adjustment member 36 of the radiation detector 10 of the present exemplary embodiment is a stacked film configured by stacking an anti-static film 36A and a neutral stress plane adjustment film 36B in the stacking direction P.

As illustrated in FIG. 9, the anti-static film 36A is provided closer to the base member 14 side than the neutral stress plane adjustment film 36B, in other words on the side corresponding to the second surface 14B of the base member 14. The anti-static film 36A has a function of preventing static buildup in the sensor substrate 12. Accordingly, as described above, the anti-static film 36A is preferably provided closer to the sensor substrate 12 side than the neutral stress plane adjustment film 36B, and is more preferably in direct contact with the sensor substrate 12. Examples of the anti-static film 36A include anti-static films such as films employing an ALPET sheet or the anti-static coating COL-COAT (trade name, manufactured by COLCOAT Co., Ltd.). In such cases, the anti-static film 36A may be formed by sticking such an anti-static film to the second surface 14B of the base member 14.

The neutral stress plane adjustment film 36B principally has a function of adjusting the position of the neutral stress plane 37 to within the permissible range. In general, the thickness of the anti-static film 36A is thin and the anti-static film 36A alone would be insufficient to adjust the position of the neutral stress plane 37. Accordingly, in the present exemplary embodiment, the neutral stress plane adjustment film 36B is provided such that the overall neutral stress plane adjustment member 36 adjusts the position of the neutral stress plane 37 to within the permissible range. The neutral stress plane adjustment film 36B may be configured from the same materials as the neutral stress plane adjustment member 36 described in the first exemplary embodiment, and may be formed by a similar manufacturing method.

The base member 14 of the present exemplary embodiment is flexible, and since the thickness of the base member 14 is thinner than that of a general non-flexible radiation detector, static is liable to build up in the base member 14 due to friction and the like. In cases in which static builds up in the sensor substrate 12, the sensor substrate 12 may deteriorate for example due to electrostatic damage to the TFTs 20, and there is therefore a concern of a decline in the image quality of radiographic images obtained using the radiation detector 10.

As a response to such situations, in the radiation detector 10 of the present exemplary embodiment the neutral stress plane adjustment member 36 is a stacked film including the stacked anti-static film 36A and neutral stress plane adjustment film 36B. This enables static buildup in the sensor substrate 12 to be suppressed.

Third Exemplary Embodiment

A radiation detector 10 of the present exemplary embodiment differs from the radiation detector 10 of the second exemplary embodiment in the configuration of the neutral stress plane adjustment member 36.

Figure 10:
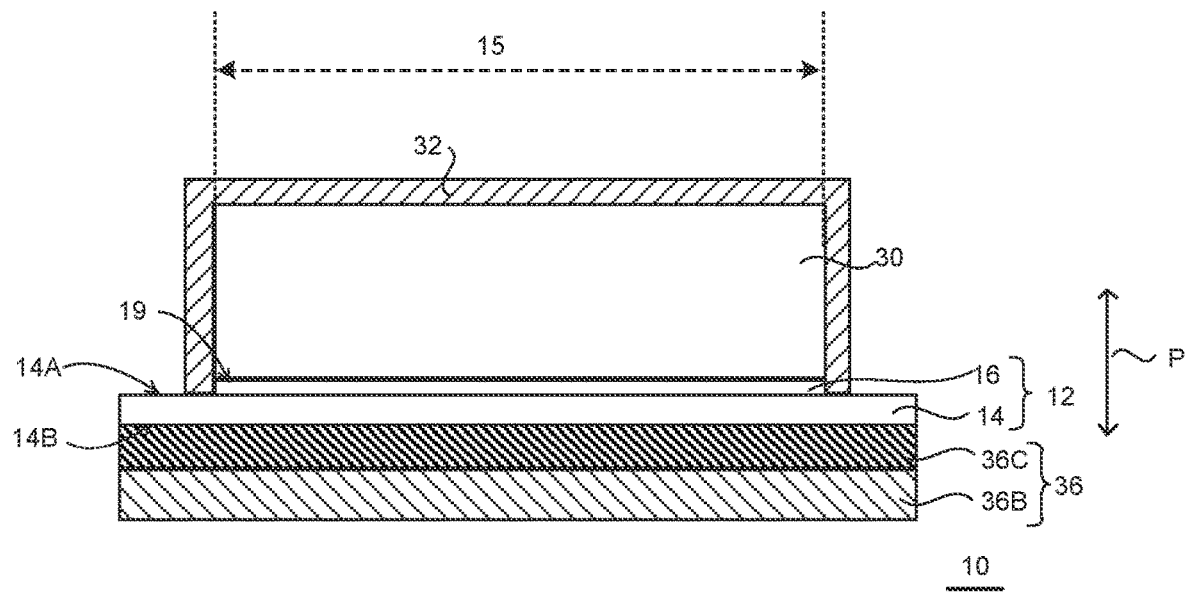
FIG. 10 is a cross-section illustrating another radiation detector of a third exemplary embodiment.

FIG. 10 is a cross-section illustrating an example of the radiation detector 10 of the present exemplary embodiment. As illustrated in FIG. 10, the neutral stress plane adjustment member 36 of the radiation detector 10 of the present exemplary embodiment is a stacked film configured by stacking a moisture-proof film 36C and a neutral stress plane adjustment film 36B in the stacking direction P.

Namely, as illustrated in FIG. 10, the neutral stress plane adjustment member 36 of the present exemplary embodiment differs from the neutral stress plane adjustment member 36 of the second exemplary embodiment in the point that the moisture-proof film 36C is included instead of the anti-static film 36A of the neutral stress plane adjustment member 36 of the second exemplary embodiment.

As illustrated in FIG. 10, the moisture-proof film 36C is provided closer to the side of the base member 14 than the neutral stress plane adjustment film 36B, in other words on the side corresponding to the second surface 14B of the base member 14. The moisture-proof film 36C is capable of improving moisture proofing performance with respect to the base member 14 and the conversion layer 30. In particular, in cases in which the conversion layer 30 is CsI, CsI is vulnerable to moisture, and so there would be a concern of a drop in the image quality of the radiographic images were moisture ingress to occur inside the radiation detector 10. Accordingly, in cases in which CsI is employed in the conversion layer 30, the moisture proofing performance of the conversion layer 30 is preferably enhanced as in the radiation detector 10 of the present exemplary embodiment.

Accordingly, the moisture-proof film 36C is preferably provided closer to the sensor substrate 12 side than the neutral stress plane adjustment film 36B as described above, and more preferably directly contacts the sensor substrate 12. Similarly to the protective film 32, examples of the moisture-proof film 36C include a Parylene film, an insulating sheet such as polyethylene terephthalate, and a moisture-proof film such as an ALPET sheet. In such cases, the moisture-proof film 36C may be formed by sticking the moisture-proof film to the second surface 14B of the base member 14.

In the radiation detector 10 of the present exemplary embodiment, by thus configuring the neutral stress plane adjustment member 36 as a stacked film in which the moisture-proof film 36C and the neutral stress plane adjustment film 36B are stacked, moisture ingress from the side of the second surface 14B of the base member 14 can be suppressed, enabling moisture proofing to be enhanced.

Note that embodiments in which the neutral stress plane adjustment member 36 has a stacked configuration of plural stacked films are not limited to the configurations of the neutral stress plane adjusting members 36 described in the present exemplary embodiment or the second exemplary embodiment. For example, the neutral stress plane adjustment member 36 may be configured including both the anti-static film 36A and the moisture-proof film 36C, or may be configured including a thermal insulation film, a vibration damping film, or the like instead of, or in addition to, the anti-static film 36A and the moisture-proof film 36C.

As described above, the radiation detectors 10 of the respective exemplary embodiments described above each include the sensor substrate 12 including the flexible base member 14 and the layer provided on the first surface 14A of the base member 14 and formed with plural of the pixels 16 configured to accumulate electrical charge generated in response to light converted from radiation, the conversion layer 30 provided on the opposite side of the layer formed with the pixels 16 to the side where the base member 14 is provided and configured to convert radiation into light, and the neutral stress plane adjustment member 36 provided on the side of the base member 14 corresponding to the second surface 14B that is on the opposite side to the first surface 14A, and configured to adjust the position of the neutral stress plane 37 to within a predetermined permissible range in the stacking direction P in which the sensor substrate 12 and the conversion layer 30 are stacked from the interface 19 at the face of the conversion layer 30 opposing the sensor substrate 12.

In the radiation detector 10 in which the flexible base member 14 is employed as the sensor substrate 12, the conversion layer 30 is likely to detach from the sensor substrate 12 due to bending of the sensor substrate 12. In particular, the sensor substrate 12 is more likely to bend in cases in which the radiation detector 10 is manipulated on its own, for example when being handled before being provided inside the case 120 during manufacturing processes of the radiographic imaging device 1, than in a state assembled to the radiographic imaging device 1. Accordingly, since the sensor substrate 12 is likely to bend when the radiation detector 10 is manipulated on its own, the conversion layer 30 is likely to detach from the sensor substrate 12.

The radiation detectors 10 of the exemplary embodiments described above therefore adjust the position of the neutral stress plane 37 to a position within the permissible range from the interface 19 using the neutral stress plane adjustment member 36. This enables the conversion layer 30 to be suppressed from detaching from the sensor substrate 12 during bending of the radiation detector 10, even when the radiation detector 10 is on its own.

Accordingly, the radiation detectors 10 of the exemplary embodiments described above are capable of suppressing the sensor substrate and the conversion layer from detaching from one another even when the radiation detector 10 is on its own, in comparison to a radiographic imaging device in which the radiation detector 10 and electric circuitry is arranged in a direction intersecting a stacking direction in which the conversion layer 30 and the sensor substrate 12 are stacked and a bending adjustment member is provided across the entirety of the radiation detector 10 and the electric circuitry.

Note that although the region in which the neutral stress plane adjustment member 36 is provided is not particularly limited, the neutral stress plane adjustment member 36 should be provided in a region on the second surface 14B side of the base member 14 so as to cover at least a region in which the sensor substrate 12 and the conversion layer 30 oppose each other.

Figure 11:
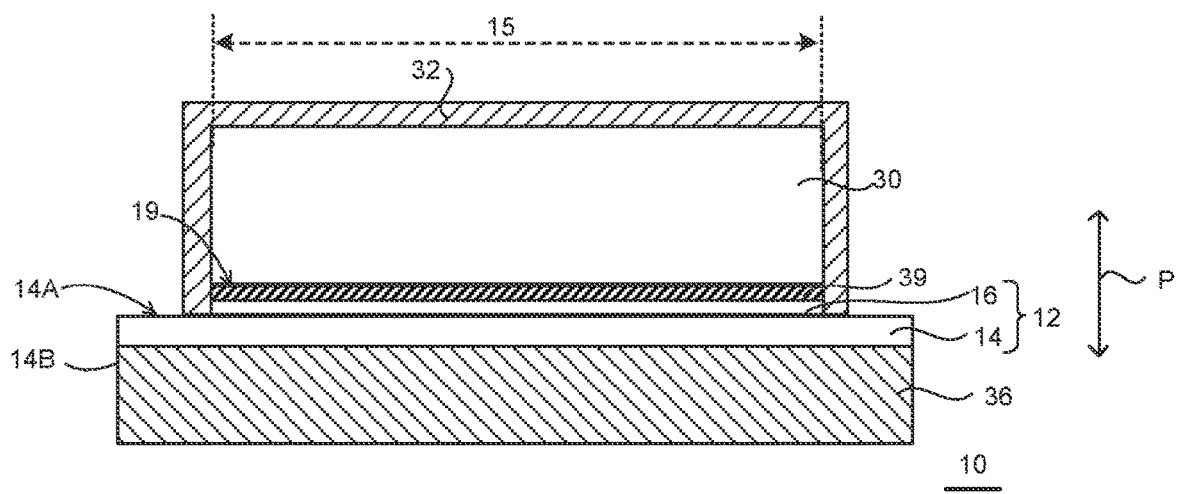
FIG. 11 is a cross-section illustrating another example of a radiation detector of the first exemplary embodiment.

Note that in the exemplary embodiments described above, explanation has been given regarding embodiments in which the conversion layer 30 is provided directly to the sensor substrate 12. However, there is no limitation to such embodiments, and another layer (film) may be provided between the sensor substrate 12 and the conversion layer 30. For example, the radiation detector 10 may include a cohesion layer 39 between the sensor substrate 12 and the conversion layer 30 as in the example illustrated in FIG. 11. In other words, the sensor substrate 12 may contact the conversion layer 30 through the cohesion layer 39. The cohesion layer 39 is provided to enhance the level of cohesion between the sensor substrate 12 and the conversion layer 30 in comparison to cases in which the cohesion layer 39 is not provided. Since including the cohesion layer 39 enhances the level of cohesion between the sensor substrate 12 and the conversion layer 30, the conversion layer 30 detaches from the sensor substrate 12 less readily than in cases in which the cohesion layer 39 is not provided. Accordingly, in cases in which the cohesion layer 39 is provided the thickness of the neutral stress plane adjustment member 36 may be reduced in comparison to cases in which the cohesion layer 39 is not provided. A Parylene film or the like may be employed as the cohesion layer 39.

Figure 12:
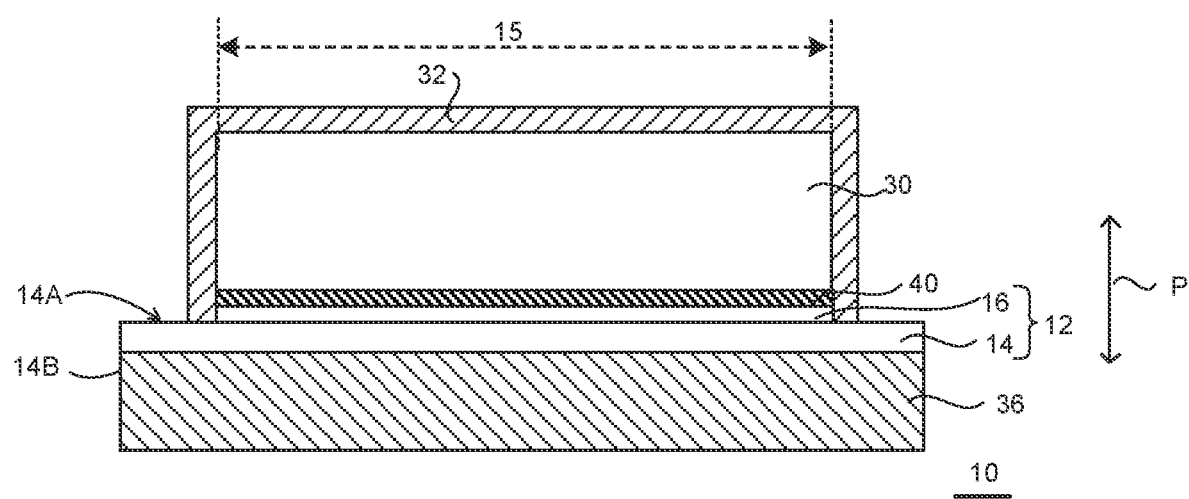
FIG. 12 is a cross-section illustrating another example of a radiation detector of the first exemplary embodiment.

As another example, the radiation detector 10 may include a buffer layer 40 between the sensor substrate 12 and the conversion layer 30 as in the example illustrated in FIG. 12. The buffer layer 40 has a function of buffering the difference between the coefficient of thermal expansion of the conversion layer 30 and the coefficient of thermal expansion of the base member 14. The coefficient of thermal expansion of the buffer layer 40 is a coefficient of thermal expansion lying between the coefficient of thermal expansion of the sensor substrate 12 and the coefficient of thermal expansion of the conversion layer 30. The greater the difference between the coefficient of thermal expansion of the conversion layer 30 and the coefficient of thermal expansion of the base member 14, the more preferable it is that the radiation detector 10 includes the buffer layer 40. For example, in cases in which XENOMAX (registered trademark) is employed for the base member 14, the difference to the coefficient of thermal expansion of the conversion layer 30 is greater than it would be with other materials, and so the buffer layer 40 is preferably provided as in the radiation detector 10 illustrated in FIG. 12. A PI film or a Parylene film may be employed as the buffer layer 40.

In the exemplary embodiments described above, explanation has been given regarding embodiments in which the radiation detector 10 is manufactured using a lamination method. However, there is no limitation to such embodiments, and the radiation detector 10 may be manufactured using a coating method.

In the exemplary embodiments described above, explanation has been given regarding embodiments in which an ISS approach is adopted for the radiation detector 10 (radiographic imaging device 1). However, a penetration side sampling (PSS) approach may be adopted for the radiation detector 10 (radiographic imaging device 1), such that the sensor substrate 12 is disposed on the opposite side to the radiation-incident side of the conversion layer 30.

In the exemplary embodiments described above, explanation has been given regarding embodiments in which the pixels 16 are arrayed in a two-dimensional matrix pattern as illustrated in FIG. 1. However, there is no limitation thereto, and the pixels 16 may be arrayed in one dimension, or may be arrayed in a honeycomb formation. The shape of the pixels is not limited, and the pixels may be rectangular or polygonal, such as hexagonal, in shape. Obviously the shape of the pixel region 15 is likewise not limited.

The configurations and manufacturing methods of the radiographic imaging device 1, the radiation detector 10, and so on of the exemplary embodiments described above are merely examples thereof, and obviously modifications are possible according to circumstances within a range not departing from the spirit of the present disclosure.

Other Exemplary Embodiments

In the radiation detectors 10 of the exemplary embodiments described above, explanation has been given regarding embodiments in which the neutral stress plane adjustment member 36 is provided on the sensor substrate 12 side of the stacked body configured by stacking the sensor substrate 12 and the conversion layer 30 on one another. As illustrated in FIG. 13 to FIG. 34, in the radiation detectors 10 of the exemplary embodiments described above, a reinforcement member 50 may further be provided on the conversion layer 30 side of a stacked body 21 configured by stacking the sensor substrate 12 and the conversion layer 30 on one another.

Note that the position of the neutral stress plane 37 in the stacked body 21 configured by stacking the conversion layer 30 on the sensor substrate 12 differs from the position of the neutral stress plane 37 in the overall stacked body in a state in which the reinforcement member 50 is provided on the stacked body 21. Accordingly, in cases in which the reinforcement member 50 is provided, the neutral stress plane adjustment member 36 brings the neutral stress plane 37 and the interface 19 closer together when the state in which the reinforcement member 50 is provided to the stacked body 21 is considered as a single stacked body.

The reinforcement member 50 has higher bending rigidity than the base member 14, such that dimensional change (deformation) with respect to force applied in a direction perpendicular to a face opposing the conversion layer 30 is smaller than the dimensional change with respect to force applied in a direction perpendicular to the first surface 14A of the base member 14. The thickness of the reinforcement member 50 of the present exemplary embodiment is also greater than the thickness of the base member 14. Note that the bending rigidity referred to here refers to bending difficulty with bending becoming more difficult the greater the bending rigidity.

More specifically, the reinforcement member 50 of the present exemplary embodiment preferably employs a material having a bending elastic modulus of from 150 MPa to 2500 MPa. The bending elastic modulus is, for example, measured according to JIS K7171:2016. The reinforcement member 50 preferably has higher bending rigidity than the base member 14 from the perspective of suppressing bending of the base member 14. Note that since the bending rigidity decreases as the bending elastic modulus decreases, the thickness of the reinforcement member 50 has to be increased in order to obtain the desired bending rigidity, causing an increase in the overall thickness of the radiation detector 10. Considering the materials of the reinforcement member 50 described above, the thickness of the reinforcement member 50 tends to become comparatively large when attempting to obtain a bending rigidity in excess of 140,000

Pacm⁴. Accordingly, in consideration of both obtaining an appropriate rigidity and the overall thickness of the radiation detector 10, the material employed for the reinforcement member 50 preferably has a bending elastic modulus of from 150 MPa to 2500 MPa. The bending rigidity of the reinforcement member 50 is preferably from 540 Pacm⁴ to 140,000 Pacm⁴.

The coefficient of thermal expansion of the reinforcement member 50 is preferably close to the coefficient of thermal expansion of the material of the conversion layer 30, and more preferably, the ratio of the coefficient of thermal expansion of the reinforcement member 50 with respect to the coefficient of thermal expansion of the conversion layer 30 (the coefficient of thermal expansion of the reinforcement member 50 divided by the coefficient of thermal expansion of the conversion layer 30) is preferably from 0.5 to 2. The coefficient of thermal expansion of the reinforcement member 50 is preferably from 30 ppm/K to 80 ppm/K. For example, in cases in which the material of the conversion layer 30 is CsI:Tl, the coefficient of thermal expansion thereof is 50 ppm/K. In such cases, examples of materials comparatively close to that of the conversion layer 30 include polyvinyl chloride (PVC) with a coefficient of thermal expansion of from 60 ppm/K to 80 ppm/K, acrylic with a coefficient of thermal expansion of from 70 ppm/K to 80 ppm/K, PET with a coefficient of thermal expansion of from 65 ppm/K to 70 ppm/K, polycarbonate (PC) with a coefficient of thermal expansion of 65 ppm/K, TEFLON (registered trademark) with a coefficient of thermal expansion of from 45 ppm/K to 70 ppm/K, and the like.

Moreover, in consideration of the bending elastic modulus as described above, the material of the reinforcement member 50 is preferably a material containing at least one out of PET or PC.

From the perspective of elasticity, the reinforcement member 50 preferably contains a material having a yield point. In the present exemplary embodiment, the "yield point" refers to the point at which stress does not increase but strain does increase on a curve expressing the relationship between stress and strain in the phenomenon in which stress suddenly decreases when the material is applied with tension, and is the apex of the stress-strain curve when the material is tested for tensile strength. Examples of resins having a yield point are generally hard resins with high toughness, and soft resins with high toughness and moderate strength. PC is an example of a hard resin with high toughness. Polypropylene is an example of a soft resin with high toughness and moderate strength.

The reinforcement member 50 of the present exemplary embodiment is a substrate made of a plastic material. The plastic employed as the material of the reinforcement member 50 is preferably a thermoplastic resin for the reasons given above, and examples thereof include at least one out of PC, PET, styrene, acrylic, polyacetase, Nylon, polypropylene, acrylonitrile butadiene styrene (ABS), an engineering plastic, or polyphenylene ether. Note that of these, at least one out of polypropylene, ABS, an engineering plastic, PET, or polyphenylene ether is preferable, at least one out of styrene, acrylic, polyacetase, or Nylon is more preferable, and at least one out of PC or PET is even more preferably employed for the reinforcement member 50.

In cases in which the conversion layer 30 is formed using a vapor phase deposition method, as illustrated in FIG. 13 to FIG. 34, the conversion layer 30 is formed with a slope with a gradually decreasing thickness on progression toward an outer edge thereof. In the following explanation, a central region of the conversion layer 30 where the thickness may be regarded as substantially constant if manufacturing error and measurement error are ignored is referred to as a central portion 30A. An outer peripheral region of the conversion layer 30 where the thickness is, for example, not more than 90% of the average thickness of the central portion 30A of the conversion layer 30 is referred to as a peripheral edge portion 30B. Namely, the conversion layer 30 includes a sloping face that slopes with respect to the sensor substrate 12 at the peripheral edge portion 30B.

As illustrated in FIG. 13 to FIG. 33, an adhesion layer 60, a reflective layer 62, a bonding layer 64, a protective layer 65, and a bonding layer 48 may be provided between the conversion layer 30 and the reinforcement member 50.

The adhesion layer 60 covers the entire front surface of the conversion layer 30, including the central portion 30A and the peripheral edge portion 30B of the conversion layer 30. The adhesion layer 60 includes a function to fix the reflective layer 62 to the conversion layer 30. The adhesion layer 60 preferably has light-transmitting properties. Examples of materials that may be employed for the adhesion layer 60 include acrylic-based adhesives, hot-melt-based adhesives, silicone-based bonding agents, and the like. Examples of acrylic-based adhesives include, for example, urethane acrylates, acrylic resin acrylates, epoxy acrylates, and the like. Examples of hot-melt-based adhesives include thermoplastic plastics such as copolymer resins of ethylene vinyl acetate (EVA), copolymer resins of ethylene and acrylic acid (EAA), copolymer resins of ethylene and ethyl acrylate (EEA), copolymers of ethylene/methyl methacrylate (EMMA), and the like. The thickness of the adhesion layer 60 is preferably from 2 μm to 7 μm. Making the thickness of the adhesion layer 60 not less than 2 μm enables the effect of fixing the reflective layer 62 to the conversion layer 30 to be sufficiently exhibited. Furthermore, this also enables the risk of an air layer being formed between the conversion layer 30 and the reflective layer 62 to be suppressed. Were an air layer to be formed between the conversion layer 30 and the reflective layer 62, then there would be concern that multiple reflection of the light emitted from the conversion layer 30 might occur, with the light being repeatedly reflected between the air layer and the conversion layer 30, and between the air layer and the reflective layer 62. Moreover, making the thickness of the adhesion layer 60 not greater than 7 μm enables a reduction in modulation transfer function (MTF) and detective quantum efficiency (DQE) to be suppressed.

The reflective layer 62 covers the entire front surface of the adhesion layer 60. The reflective layer 62 has a function of reflecting light converted by the conversion layer 30. The reflective layer 62 is preferably configured from an organic material. Examples of materials that may be employed for the reflective layer 62 include white PET, $TiO_2$, $Al_2O_3$, foamed white PET, polyester-based high reflectivity sheets, specular reflective aluminum, and the like. The thickness of the reflective layer 62 is preferably from 10 μm to 40 μm.

The bonding layer 64 covers the entire front surface of the reflective layer 62. An end portion of the bonding layer 64 extends as far as the front surface of the sensor substrate 12. Namely, the bonding layer 64 is bonded to the sensor substrate 12 at this end portion. The bonding layer 64 has a function to fix the reflective layer 62 and the protective layer 65 to the conversion layer 30. The same materials as may be employed for the adhesion layer 60 may be employed as the material of the bonding layer 64. However, the bonding strength of the bonding layer 64 is preferably greater than the bonding strength of the adhesion layer 60.

The protective layer 65 has a function corresponding to that of the protective film 32 of the radiation detectors 10 of the exemplary embodiments described above, and covers the entire front surface of the bonding layer 64. Namely, the protective layer 65 is provided so as to cover the entirety of the conversion layer 30, and an end portion of the protective layer 65 also covers a portion of the sensor substrate 12. The protective layer 65 functions as a moisture-proof film to prevent the ingress of moisture into the conversion layer 30. Examples of materials that may be employed as the material of the protective layer 65 include organic films containing an organic material such as PET, PPS, OPP, PEN, PI, and the like. Moreover, an ALPET (registered trademark) sheet may be employed as the protective layer 65.

The reinforcement member 50 is provided on the front surface of the protective layer 65, with the bonding layer 48 interposed therebetween. The same materials as may be employed for the adhesion layer 60 and the bonding layer 48 may, for example, be employed as the material of the bonding layer 48.

Figure 13:
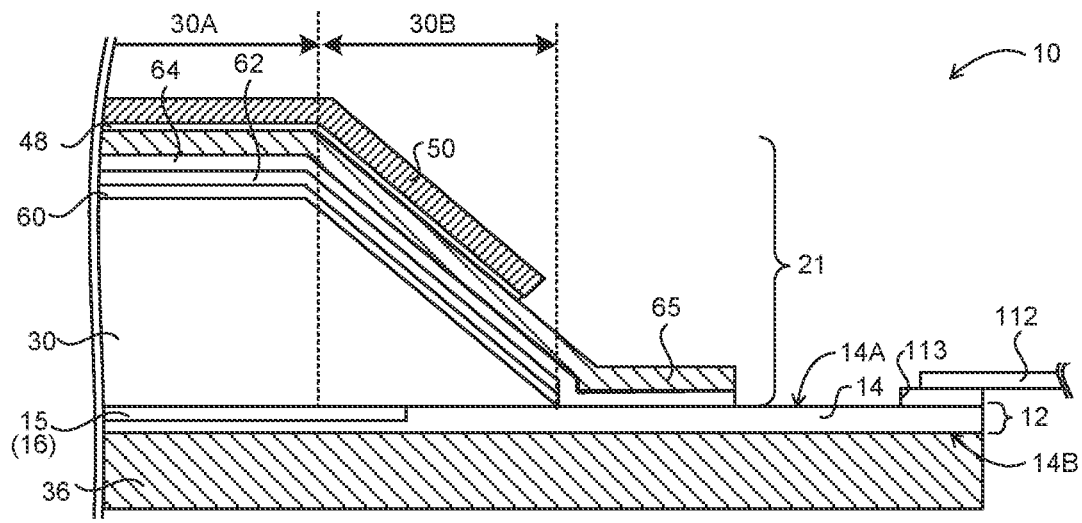
FIG. 13 is a cross-section illustrating an example of configuration of a radiation detector of an exemplary embodiment of technology disclosed herein.

In the example illustrated in FIG. 13, the reinforcement member 50 extends over regions corresponding to the central portion 30A and the peripheral edge portion 30B of the conversion layer 30, with an outer peripheral portion of the reinforcement member 50 angled so as to follow the slope of the peripheral edge portion 30B of the conversion layer 30. The reinforcement member 50 is bonded to the protective layer 65 through the bonding layer 48 at both the region corresponding to the central portion 30A and the region corresponding to the peripheral edge portion 30B of the conversion layer 30. In the example illustrated in FIG. 13, an end portion of the reinforcement member 50 is disposed at the region corresponding to the peripheral edge portion 30B of the conversion layer 30.

Figure 14:
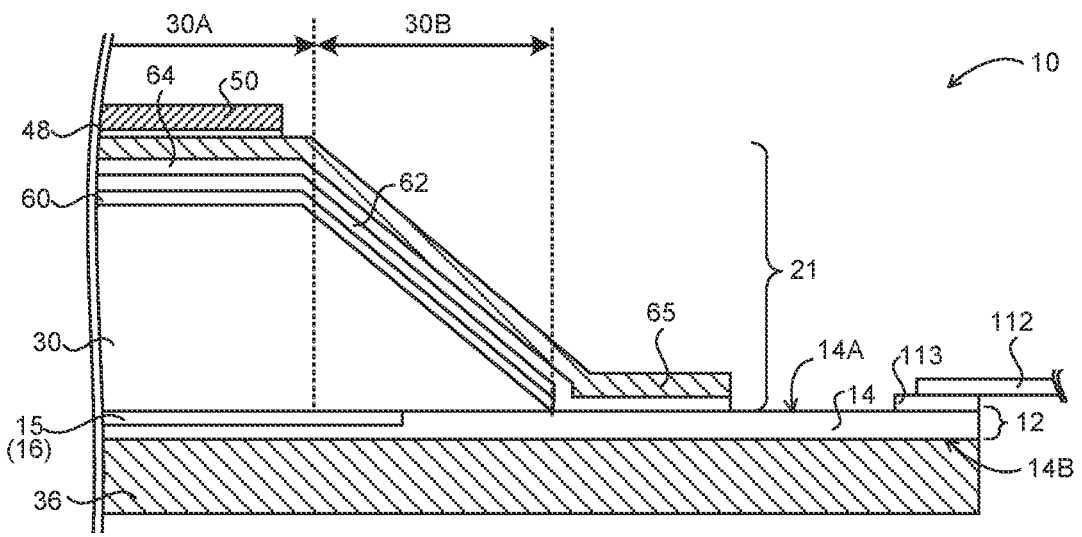
FIG. 14 is a cross-section illustrating an example of configuration of a radiation detector of an exemplary embodiment of technology disclosed herein.

As illustrated in FIG. 14, the reinforcement member 50 may be provided only at the region corresponding to the central portion 30A of the conversion layer 30. In such cases, the reinforcement member 50 is bonded to the protective layer 65 through the bonding layer 48 at the region corresponding to the central portion 30A of the conversion layer 30.

Figure 15:
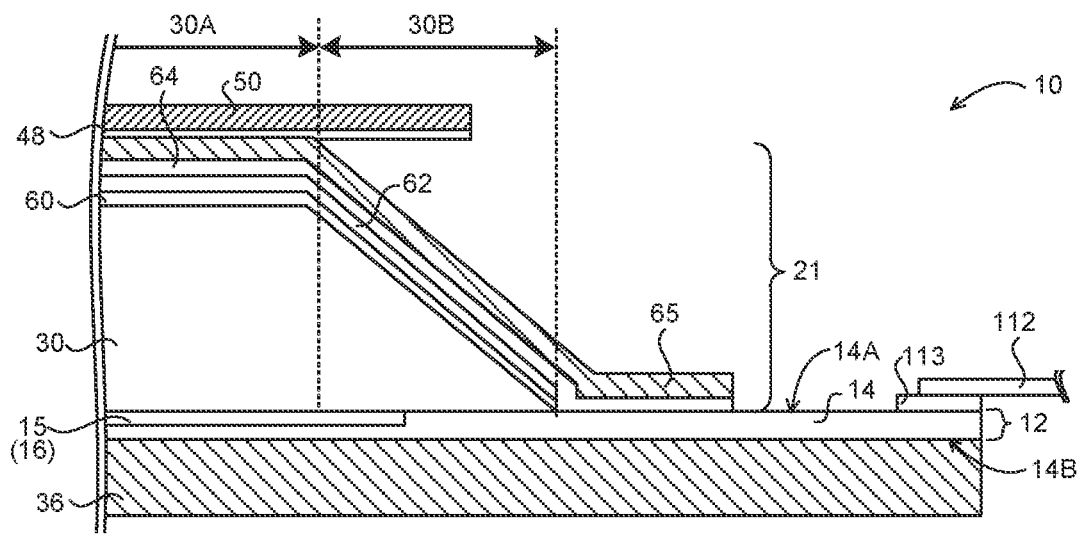
FIG. 15 is a cross-section illustrating an example of configuration of a radiation detector of an exemplary embodiment of technology disclosed herein.

As illustrated in FIG. 15, in cases in which the reinforcement member 50 extends over the regions corresponding to both the central portion 30A and the peripheral edge portion 30B of the conversion layer 30, the reinforcement member 50 may be configured without providing an angled portion to follow the slope of the outer peripheral portion of the conversion layer 30. In such cases, the reinforcement member 50 is bonded to the protective layer 65 through the bonding layer 48 at the region corresponding to the central portion 30A of the conversion layer 30. A space corresponding to the slope of the peripheral edge portion 30B of the conversion layer 30 is formed between the conversion layer 30 (the protective layer 65) and the reinforcement member 50 at the region corresponding to the peripheral edge portion 30B of the conversion layer 30.

Note that the flexible cable 112 is connected to terminals 113 provided in a connection region at the outer peripheral portion of the sensor substrate 12. The sensor substrate 12 is connected to a control board (the control board 110, see FIG. 47) through the flexible cable 112. There is a concern that the flexible cable 112 might detach from the sensor substrate 12 or positional misalignment might arise were bending of the sensor substrate 12 to occur. In such cases it is necessary to perform a task to reconnect the flexible cable 112 and the sensor substrate 12. This task to reconnect the flexible cable 112 and the sensor substrate 12 is called re-work. As illustrated in FIG. 13 to FIG. 15, by arranging the end portion of the reinforcement member 50 at the inside of the end portion of the conversion layer 30, re-work can be performed more easily than in cases in which the reinforcement member 50 extends to the vicinity of the connection region.

As illustrated in FIG. 16 to FIG. 19, the end portion of the reinforcement member 50 may be disposed outside the end portion of the conversion layer 30, and may be provided so as to be aligned with the end portions of the bonding layer 64 and the protective layer 65 that both extend onto the sensor substrate 12. Note that there is no need for the position of the end portion of the reinforcement member 50 to align exactly with the position of the end portions of the bonding layer 64 and the protective layer 65.

Figure 16:
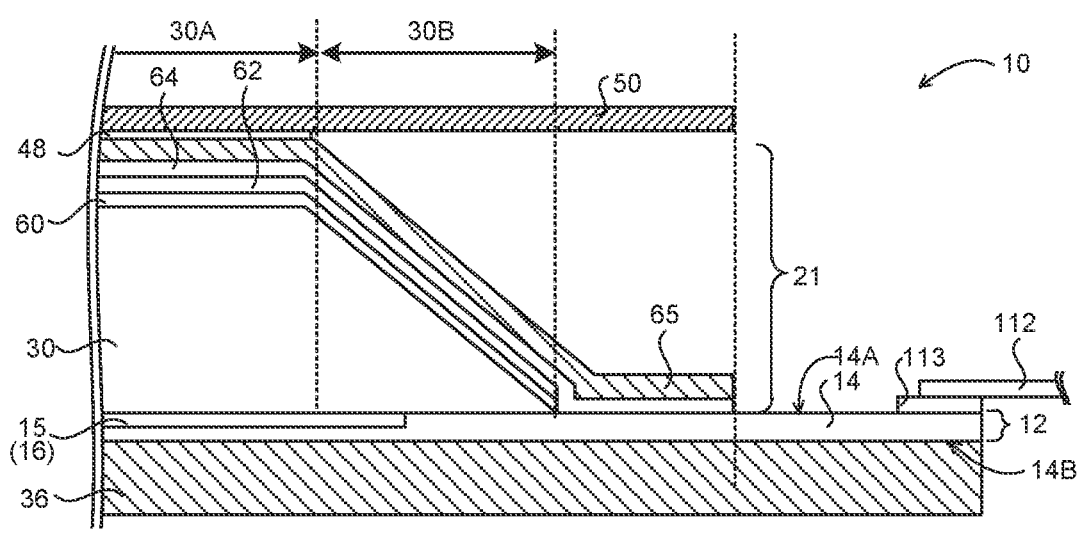
FIG. 16 is a cross-section illustrating an example of configuration of a radiation detector of an exemplary embodiment of technology disclosed herein.

In the example illustrated in FIG. 16, the reinforcement member 50 is bonded to the protective layer 65 through the bonding layer 48 at the region corresponding to the central portion 30A of the conversion layer 30, and a space corresponding to the slope at the peripheral edge portion 30B of the conversion layer 30 is formed between the conversion layer 30 (the protective layer 65) and the reinforcement member 50 at the region corresponding to the peripheral edge portion 30B of the conversion layer 30 and also in a region further to the outside thereof.

Figure 17:
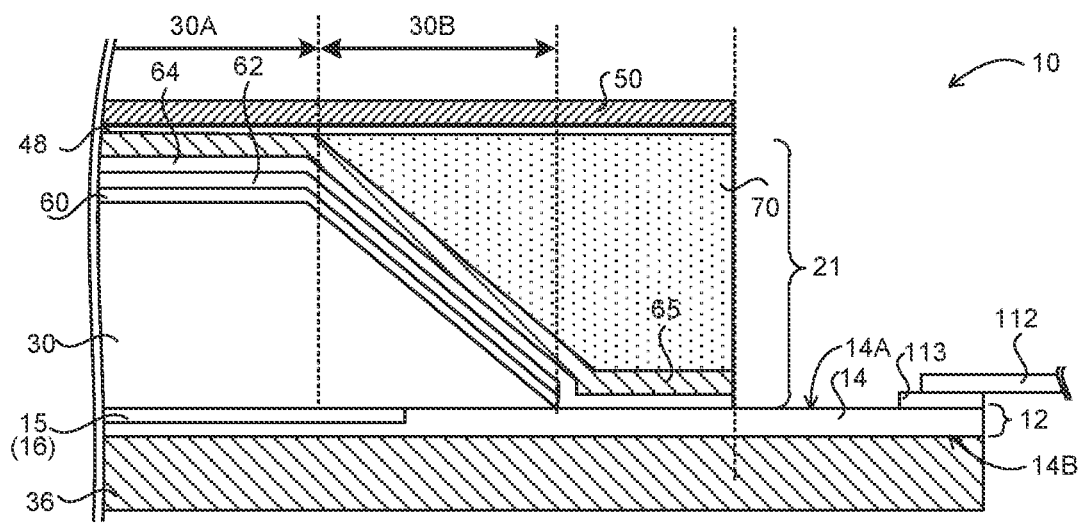
FIG. 17 is a cross-section illustrating an example of configuration of a radiation detector of an exemplary embodiment of technology disclosed herein.

In the example illustrated in FIG. 17, a filler 70 is provided in the space formed between the conversion layer 30 (the protective layer 65) and the reinforcement member 50 at the region corresponding to the peripheral edge portion 30B of the conversion layer 30 and also at the region further to the outside thereof. The material of the filler 70 is not particularly limited, and examples of materials that may be employed therefor include resins. Note that in the example illustrated in FIG. 17 the bonding layer 48 is provided across the entire region between the reinforcement member 50 and the filler 70 in order to fix the reinforcement member 50 to the filler 70.

The method of forming the filler 70 is not particularly limited. For example, after forming the bonding layer 48 and the reinforcement member 50 in sequence on the conversion layer 30 covered by the adhesion layer 60, the reflective layer 62, the bonding layer 64, and the protective layer 65, flowable filler 70 may be poured into the space formed between the conversion layer 30 (the protective layer 65) and the reinforcement member 50, and the filler 70 then cured. Alternatively, for example, after forming the conversion layer 30, the adhesion layer 60, the reflective layer 62, the bonding layer 64, and the protective layer 65 in sequence on the sensor substrate 12, the filler 70 may be formed, and the bonding layer 48 and the reinforcement member 50 may then be formed in sequence so as to cover the conversion layer 30 covered by the adhesion layer 60, the reflective layer 62, the bonding layer 64, and the protective layer 65, and also cover the filler 70.

By filling the filler 70 into the space formed between the conversion layer 30 (the protective layer 65) and the reinforcement member 50 in this manner, the reinforcement member 50 can be better suppressed from detaching from the conversion layer 30 (the protective layer 65) than in the embodiment illustrated in FIG. 16. Furthermore, due to adopting a structure in which the conversion layer 30 is fixed to the sensor substrate 12 by both the reinforcement member 50 and the filler 70, the conversion layer 30 can be suppressed from detaching from the sensor substrate 12.

Figure 18:
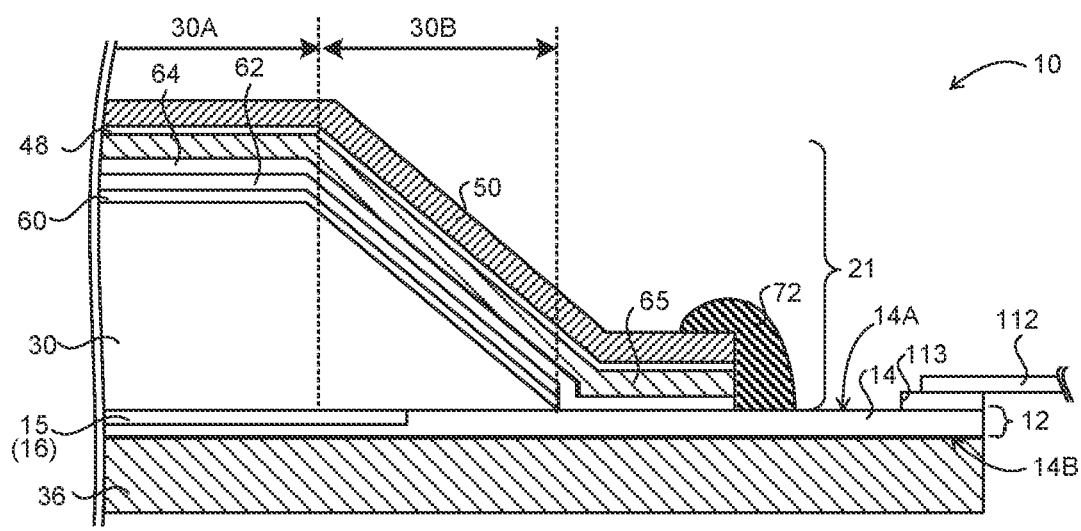
FIG. 18 is a cross-section illustrating an example of configuration of a radiation detector of an exemplary embodiment of technology disclosed herein.

In the example illustrated in FIG. 18, the outer peripheral portion of the reinforcement member 50 is angled so as to follow the slope of the peripheral edge portion 30B of the conversion layer 30, and so as also to cover the portions of the bonding layer 64 and the protective layer 65 that cover the sensor substrate 12. Moreover, the end portion of the reinforcement member 50 and the end portions of the bonding layer 64 and the protective layer 65 are aligned with each other. Note that there is no need for the position of the end portion of the reinforcement member 50 to align exactly with the position of the end portions of the bonding layer 64 and the protective layer 65.

The end portions of the reinforcement member 50, the bonding layer 48, the protective layer 65, and the bonding layer 64 are sealed with a sealing member 72. The sealing member 72 is preferably provided in a region spanning from the front surface of the sensor substrate 12 to the front surface of the reinforcement member 50, and in a region not covering the pixel region 15. Resins may be employed as the material of the sealing member 72, and thermoplastic resins are particularly preferably employed therefor. Specifically, glues such as acrylic glues, urethane based glues, and the like may be employed as the sealing member 72. The reinforcement member 50 has a higher rigidity than that of the protective layer 65, and there is a concern that recovery force due to the angle attempting to straighten out at the angled portion of the reinforcement member 50 might act to cause the protective layer 65 to detach therefrom. Sealing the end portions of the reinforcement member 50, the bonding layer 48, the protective layer 65, and the bonding layer 64 using the sealing member 72 enables such detachment of the protective layer 65 to be suppressed.

Figure 19:
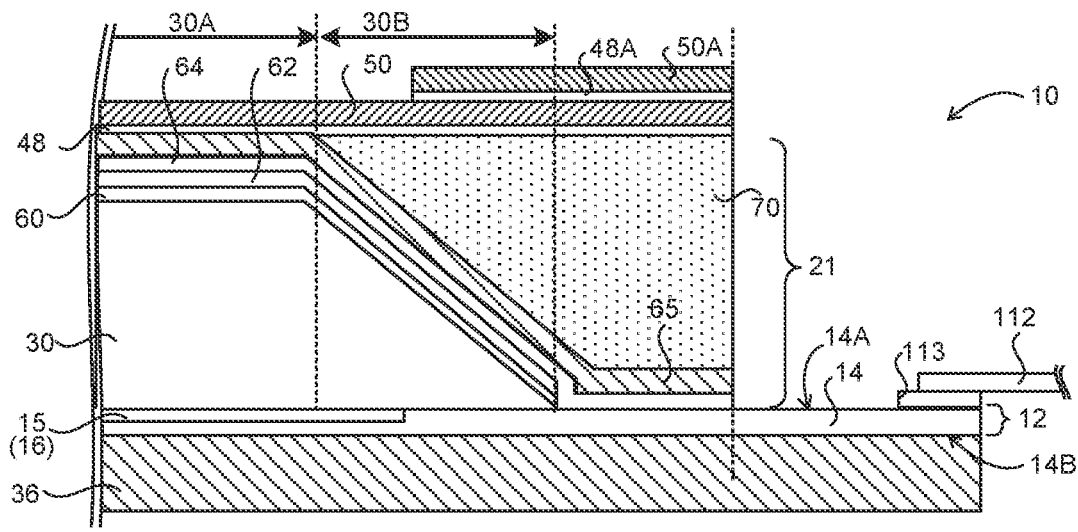
FIG. 19 is a cross-section illustrating an example of configuration of a radiation detector of an exemplary embodiment of technology disclosed herein.

Similarly to in the embodiment illustrated in FIG. 17, in the example illustrated in FIG. 19, the filler 70 is provided in a space formed between the conversion layer 30 (the protective layer 65) and the reinforcement member 50 at the region corresponding to the peripheral edge portion 30B of the conversion layer 30 and also at the region further to the outside thereof. Moreover, at the region corresponding to the end portion of the conversion layer 30, an additional and separate reinforcement member 50A is stacked on the front surface of the reinforcement member 50 with a bonding layer 48A interposed therebetween. More specifically, the reinforcement member 50A is provided in a region straddling the end portion (outer edge, edge) of the conversion layer 30. The reinforcement member 50A may be configured from the same materials as the reinforcement member 50. In the radiation detector 10, the amount of bending of the sensor substrate 12 is comparatively large at the end portion of the conversion layer 30. Forming a multi-layer structure using the reinforcement members 50 and 50A at the region corresponding to the end portion of the conversion layer 30 enables the effect of suppressing bending of the sensor substrate 12 at the end portion of the conversion layer 30 to be enhanced.

As illustrated in FIG. 16 to FIG. 19, in cases in which the end portion of the reinforcement member 50 is disposed further to the outside than the end portion of the conversion layer 30 and is provided so as to be aligned with the end portions of the bonding layer 64 and the protective layer 65, re-work can also be performed more easily than in cases in which the reinforcement member 50 extends as far as the vicinity of the connection region.

As illustrated in FIG. 20 to FIG. 23, a configuration may be adopted in which the end portion of the reinforcement member 50 is provided so as to be positioned further outside than the end portions of the bonding layer 64 and the protective layer 65 that extend onto the sensor substrate 12, and so as to be positioned at the inner side of the end portion of the sensor substrate 12.

Figure 20:
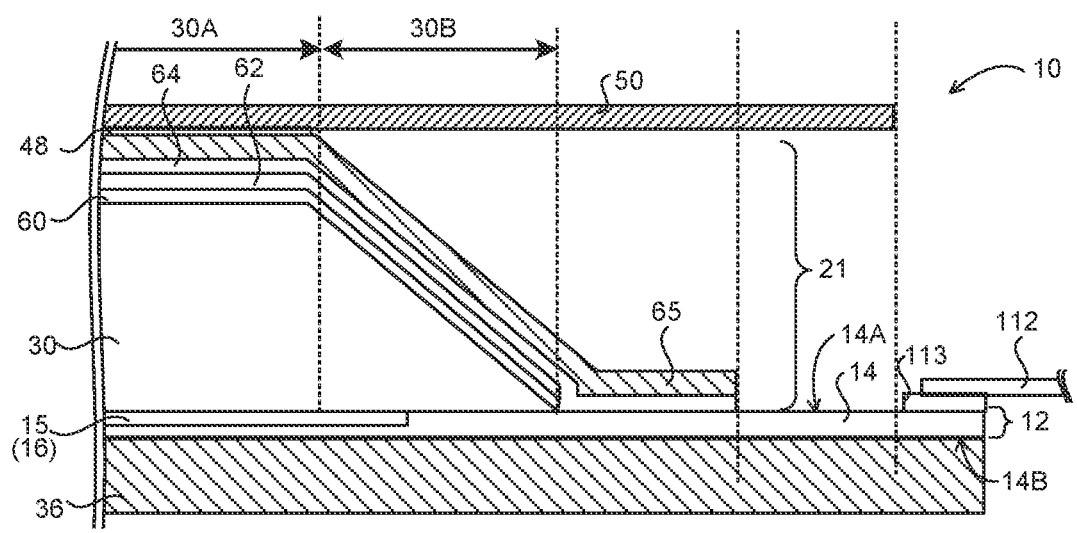
FIG. 20 is a cross-section illustrating an example of configuration of a radiation detector of an exemplary embodiment of technology disclosed herein.

In the example illustrated in FIG. 20, the reinforcement member 50 is bonded to the protective layer 65 through the bonding layer 48 at the region corresponding to the central portion 30A of the conversion layer 30. At the region corresponding to the peripheral edge portion 30B of the conversion layer 30 and also at the region further to the outside thereof, a space corresponding to the slope of the peripheral edge portion 30B of the conversion layer 30 is formed between the conversion layer 30 (the protective layer 65) and the reinforcement member 50, and between the sensor substrate 12 and the reinforcement member 50.

Figure 21:
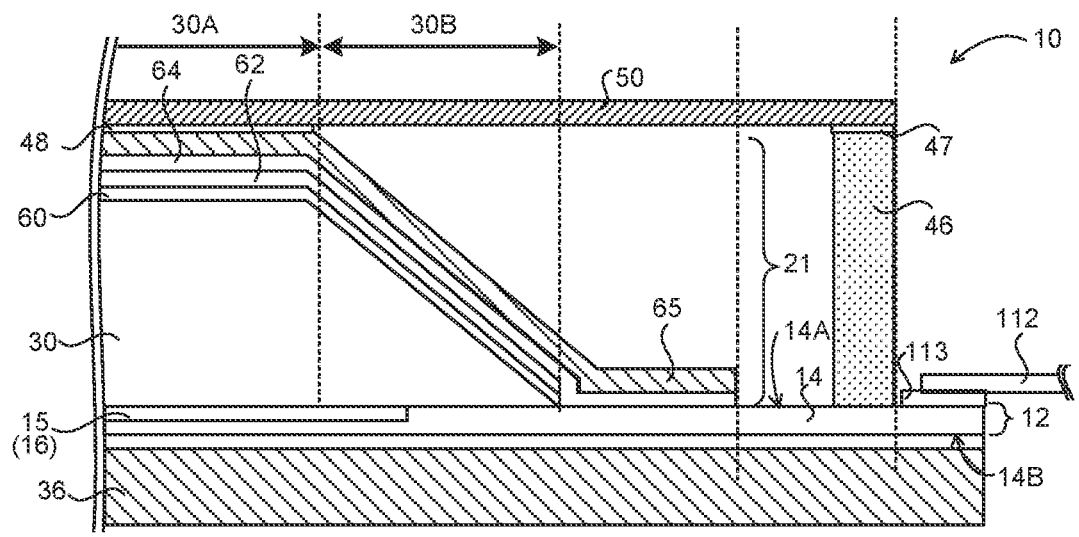
FIG. 21 is a cross-section illustrating an example of configuration of a radiation detector of an exemplary embodiment of technology disclosed herein.

In the example illustrated in FIG. 21, the end portion of the reinforcement member 50 is supported by a spacer 46. Namely, one end of the spacer 46 is connected to the first surface 14A of the base member 14 of the sensor substrate 12, and the other end of the spacer 46 is connected to the end portion of the reinforcement member 50 through a bonding layer 47. By using the spacer 46 to support the end portion of the reinforcement member 50 that extends so as to form a space between itself and the sensor substrate 12, detachment of the reinforcement member 50 can be suppressed. Moreover, the bending suppression effect from the reinforcement member 50 can be caused to act as far as the vicinity of the end portion of the sensor substrate 12. Note that instead of providing the spacer 46, or in addition to providing the spacer 46, a filler may be filled into the space formed between the conversion layer 30 (the protective layer 65) and the reinforcement member 50, and between the sensor substrate 12 and the reinforcement member 50, in a similar manner to the example illustrated in FIG. 17.

Figure 22:
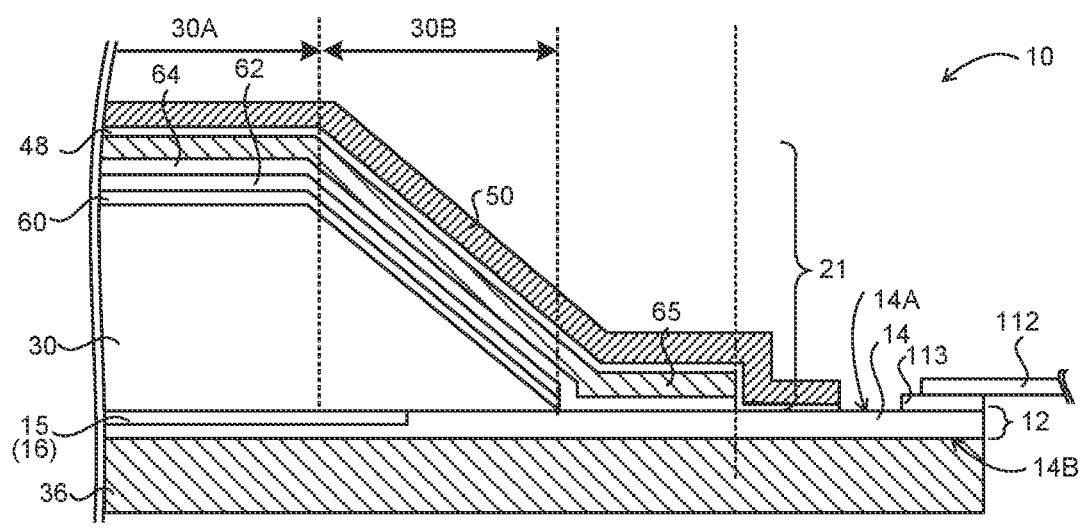
FIG. 22 is a cross-section illustrating an example of configuration of a radiation detector of an exemplary embodiment of technology disclosed herein.

In the example illustrated in FIG. 22, the outer peripheral portion of the reinforcement member 50 is angled so as to follow the slope at the peripheral edge portion 30B of the conversion layer 30, and the outer peripheral portion of the reinforcement member 50 covers the portion where the bonding layer 64 and the protective layer 65 cover the sensor substrate 12 and also covers the sensor substrate 12 at the outside thereof. Namely, the end portions of the bonding layer 64 and the protective layer 65 are sealed by the reinforcement member 50. The portion of the reinforcement member 50 that extends over the sensor substrate 12 is bonded to the sensor substrate 12 through the bonding layer 48. By covering the end portions of the bonding layer 64 and the protective layer 65 using the reinforcement member 50 in this manner, detachment of the protective layer 65 can be suppressed. Note that the sealing member 72 may be employed to seal the end portion of the reinforcement member 50, in a similar manner to the example illustrated in FIG. 18.

Figure 23:
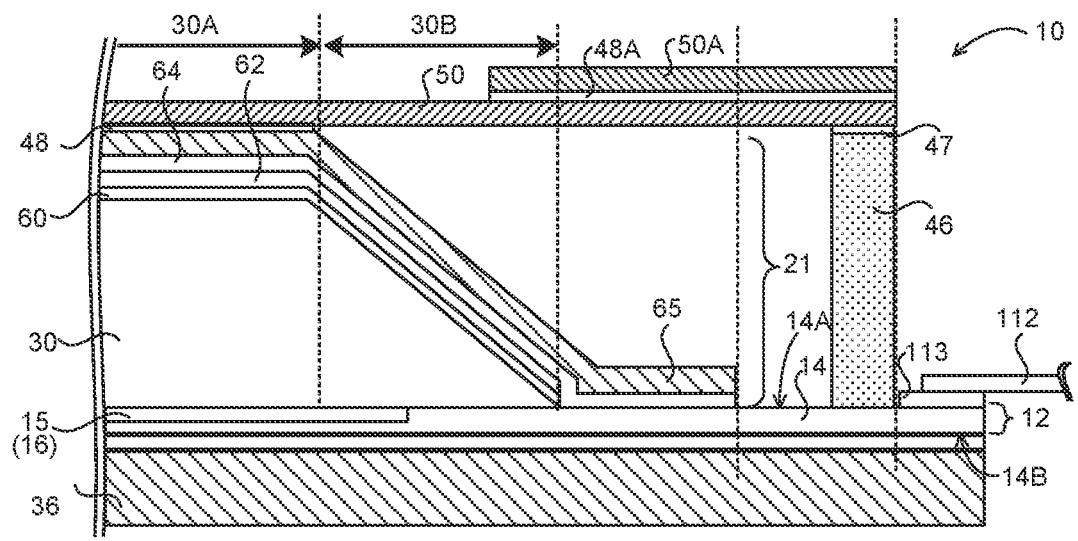
FIG. 23 is a cross-section illustrating an example of configuration of a radiation detector of an exemplary embodiment of technology disclosed herein.

The example illustrated in FIG. 23 is an embodiment in which the end portion of the reinforcement member 50 is supported by the spacer 46, and an additional and separate reinforcement member 50A is stacked on the front surface of the reinforcement member 50 at the region corresponding to the end portion of the conversion layer 30, with the bonding layer 48A interposed therebetween. More specifically, the reinforcement member 50A is provided in a region straddling the end portion (outer edge, edge) of the conversion layer 30. The reinforcement member 50A may be configured from the same materials as the reinforcement member 50. In the radiation detector 10, the amount of bending of the sensor substrate 12 is comparatively large at the end portion of the conversion layer 30. Forming a multi-layer structure using the reinforcement members 50 and 50A at the region corresponding to the end portion of the conversion layer 30 enables the effect of suppressing bending of the sensor substrate 12 at the end portion of the conversion layer 30 to be enhanced. Note that instead of providing the spacer 46, the filler 70 may be filled into the space formed between the conversion layer 30 (the protective layer 65) and the reinforcement member 50, and between the sensor substrate 12 and the reinforcement member 50, in a similar manner to the example illustrated in FIG. 17.

As illustrated in FIG. 24 to FIG. 28, the end portion of the reinforcement member 50 may be provided so as to be aligned with the end portion of the sensor substrate 12. Note that there is no need for the position of the end portion of the reinforcement member 50 to align exactly with the position of the end portion of the sensor substrate 12.

Figure 24:
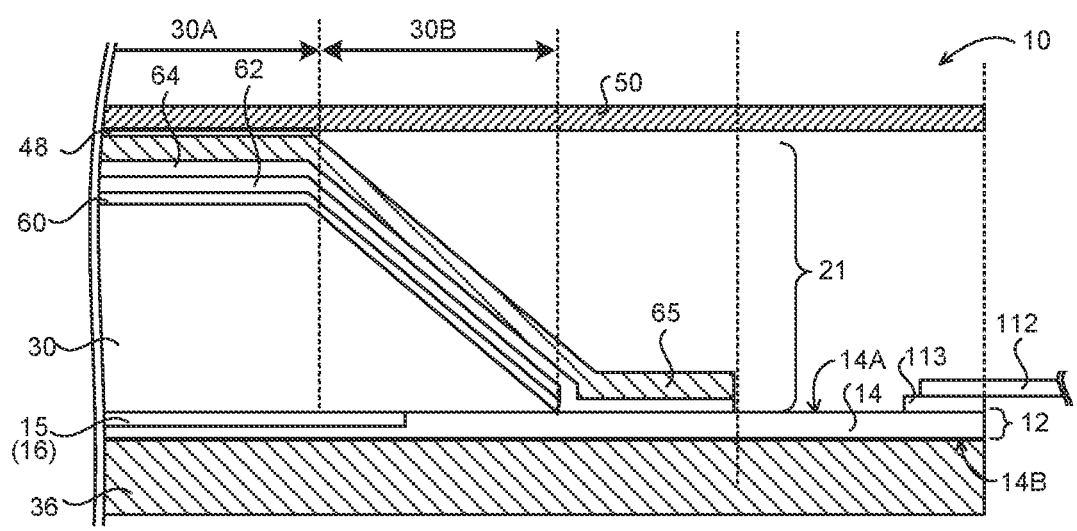
FIG. 24 is a cross-section illustrating an example of configuration of a radiation detector of an exemplary embodiment of technology disclosed herein.

In the example illustrated in FIG. 24, the reinforcement member 50 is bonded to the protective layer 65 through the bonding layer 48 at the region corresponding to the central portion 30A of the conversion layer 30. A space corresponding to the slope of the peripheral edge portion 30B of the conversion layer 30 is formed between the conversion layer 30 (the protective layer 65) and the reinforcement member 50, and between the sensor substrate 12 and the reinforcement member 50, at the region corresponding to the peripheral edge portion 30B of the conversion layer 30 and also at the region further to the outside thereof.

Figure 25:
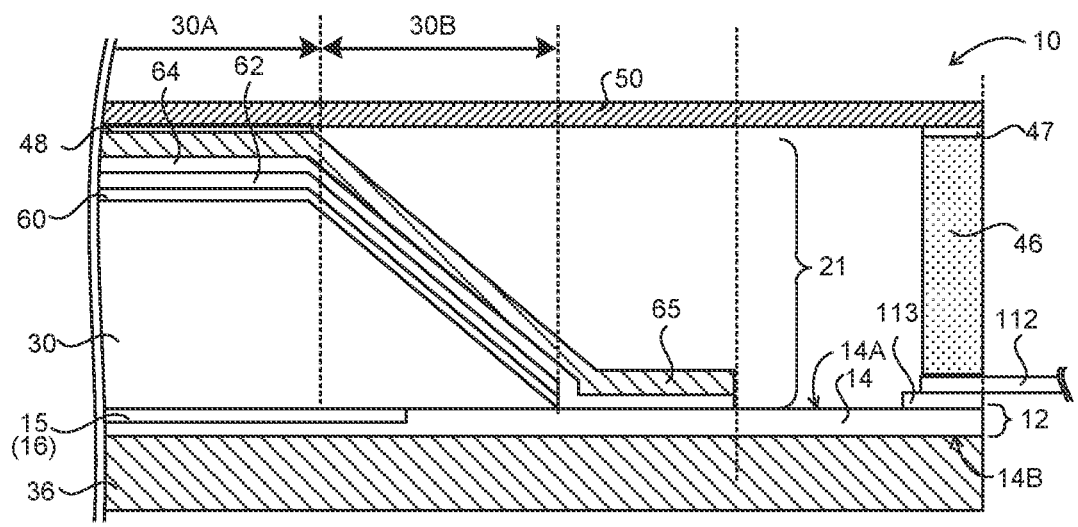
FIG. 25 is a cross-section illustrating an example of configuration of a radiation detector of an exemplary embodiment of technology disclosed herein.

In the example illustrated in FIG. 25, the end portion of the reinforcement member 50 is supported by the spacer 46. Namely, one end of the spacer 46 is connected to the flexible cable 112 provided at the end portion of the sensor substrate 12, and the other end of the spacer 46 is connected to the end portion of the reinforcement member 50 through the bonding layer 47. By using the spacer 46 to support the end portion of the reinforcement member 50 that extends so as to form a space between itself and the sensor substrate 12, detachment of the reinforcement member 50 can be suppressed. Moreover, the bending suppression effect from the reinforcement member 50 can be caused to act as far as the vicinity of the end portion of the sensor substrate 12.

Figure 26:
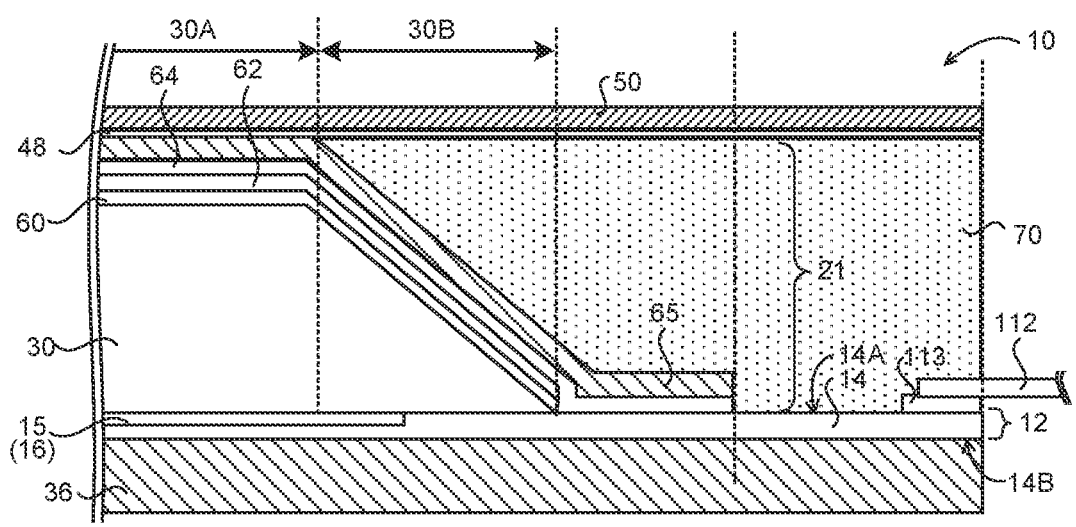
FIG. 26 is a cross-section illustrating an example of configuration of a radiation detector of an exemplary embodiment of technology disclosed herein.

In the example illustrated in FIG. 26, the space formed between the conversion layer 30 (the protective layer 65) and the reinforcement member 50, and between the sensor substrate 12 and the reinforcement member 50, is filled by the filler 70. In the present exemplary embodiment, the connection portions between the flexible cable 112 and the terminals 113 are covered by the filler 70. By thus filling the space formed between the conversion layer 30 (the protective layer 65) and the reinforcement member 50, and between the sensor substrate 12 and the reinforcement member 50, with the filler 70, the reinforcement member 50 can be better suppressed from detaching from the conversion layer 30 (the protective layer 65) than in the embodiment illustrated in FIG. 24. Furthermore, due to the conversion layer 30 having a structure fixed to the sensor substrate 12 by both the reinforcement member 50 and the filler 70, the conversion layer 30 can be suppressed from detaching from the sensor substrate 12. Moreover, since the connection portions between the flexible cable 112 and the terminals 113 are covered by the filler 70, detachment of the flexible cable 112 can also be suppressed.

Figure 27:
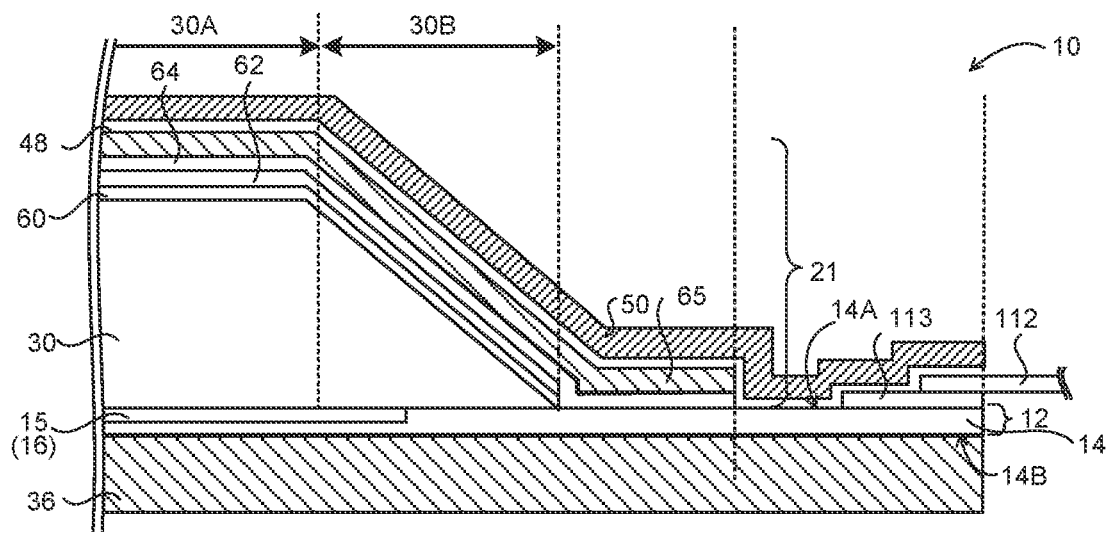
FIG. 27 is a cross-section illustrating an example of configuration of a radiation detector of an exemplary embodiment of technology disclosed herein.

In the example illustrated in FIG. 27, the outer peripheral portion of the reinforcement member 50 is angled so as to follow the slope of the peripheral edge portion 30B of the conversion layer 30. The outer peripheral portion of the reinforcement member 50 covers a portion where the bonding layer 64 and the protective layer 65 cover the sensor substrate 12, a portion of the substrate at the outside thereof, and the connection portions between the flexible cable 112 and the terminals 113. The portions of the reinforcement member 50 extending over the sensor substrate 12 and over the flexible cable 112 are respectively bonded to the sensor substrate 12 and the flexible cable 112 through the bonding layer 48. The connection portions between the flexible cable 112 and the terminals 113 are covered by the bent reinforcement member 50, enabling detachment of the flexible cable 112 to be suppressed. Moreover, since the other end of the flexible cable 112 is anticipated to be connected to a control board mounted with electronic components, there is a concern regarding comparatively large bending of the sensor substrate 12 occurring at the connection portions between the flexible cable 112 and the terminals 113. Since the connection portions between the flexible cable 112 and the terminals 113 are covered by the reinforcement member 50, such bending of the sensor substrate 12 at these portions can be suppressed.

Figure 28:
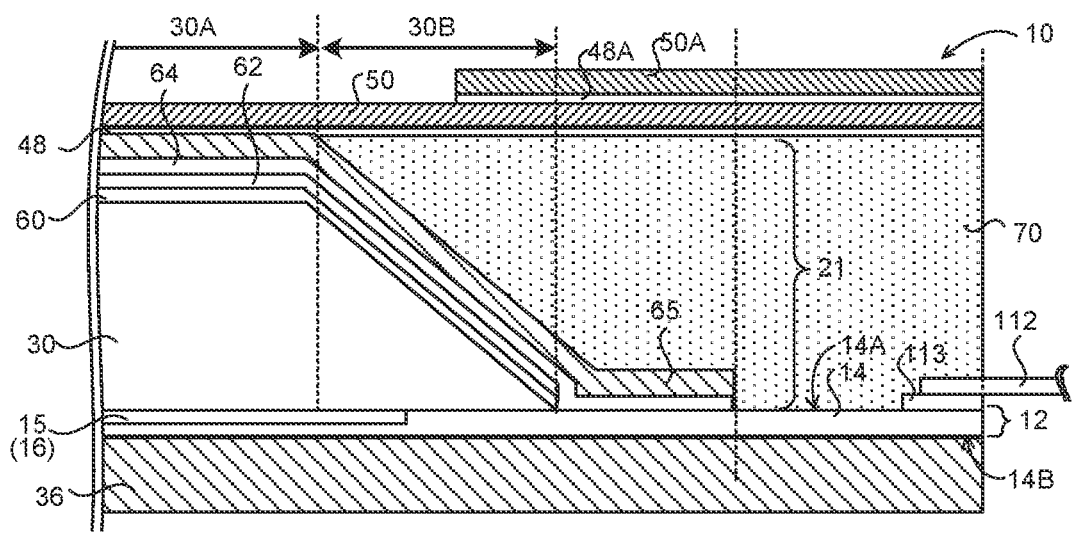
FIG. 28 is a cross-section illustrating an example of configuration of a radiation detector of an exemplary embodiment of technology disclosed herein.

In the example illustrated in FIG. 28, a space formed between the conversion layer 30 (the protective layer 65) and the reinforcement member 50, and between the sensor substrate 12 and the reinforcement member 50, is filled with the filler 70. Moreover, an additional and separate bending reinforcement member 50A is stacked on the front surface of the reinforcement member 50 at the region corresponding to the end portion of the conversion layer 30, with the bonding layer 48A interposed therebetween. More specifically, the reinforcement member 50A is provided in a region straddling the end portion (outer edge, edge) of the conversion layer 30. The reinforcement member 50A may be configured from the same materials as the reinforcement member 50. In the radiation detector 10, the amount of bending of the sensor substrate 12 is comparatively large at the end portion of the conversion layer 30. Forming a multi-layer structure using the reinforcement members 50 and 50A at the region corresponding to the end portion of the conversion layer 30 enables the effect of suppressing bending of the sensor substrate 12 to be enhanced at the end portion of the conversion layer 30.

As illustrated in FIG. 29 to FIG. 33, the end portion of the reinforcement member 50 may be provided so as to be positioned outside the end portion of the sensor substrate 12.

Figure 29:
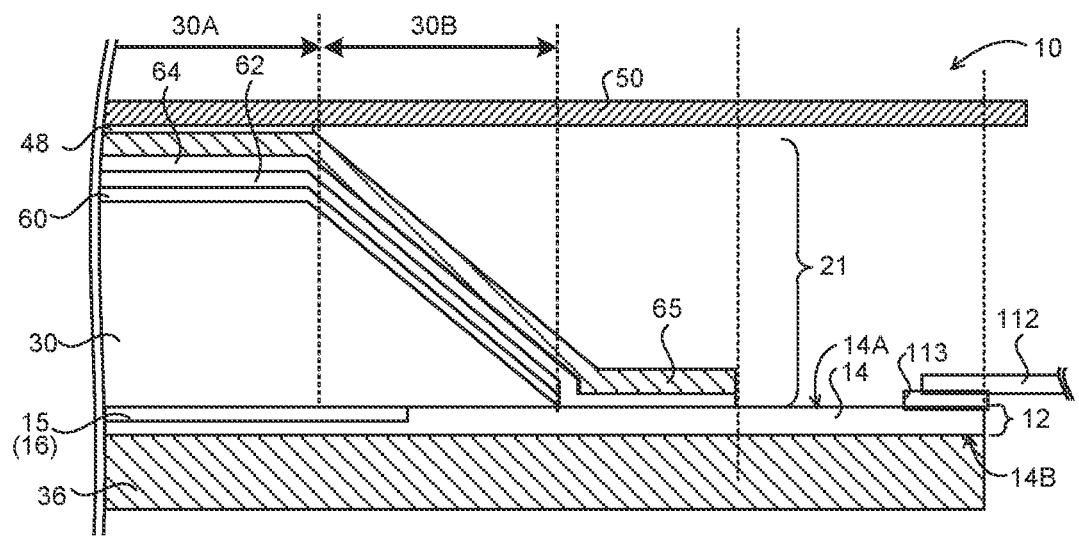
FIG. 29 is a cross-section illustrating an example of configuration of a radiation detector of an exemplary embodiment of technology disclosed herein.

In the example illustrated in FIG. 29, the reinforcement member 50 is bonded to the protective layer 65 through the bonding layer 48 at the region corresponding to the central portion 30A of the conversion layer 30. A space corresponding to the slope of the peripheral edge portion 30B of the conversion layer 30 is formed between the conversion layer 30 (the protective layer 65) and the reinforcement member 50, and between the sensor substrate 12 and the reinforcement member 50, at the region corresponding to the peripheral edge portion 30B of the conversion layer 30 and also at the region further to the outside thereof.

Figure 30:
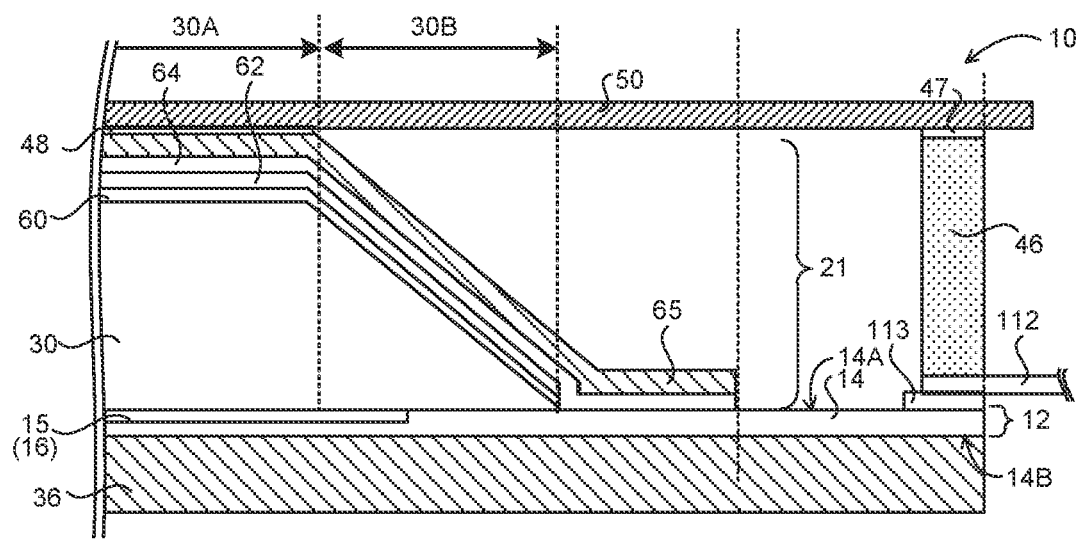
FIG. 30 is a cross-section illustrating an example of configuration of a radiation detector of an exemplary embodiment of technology disclosed herein.

In the example illustrated in FIG. 30, the end portion of the reinforcement member 50 is supported by the spacer 46. Namely, one end of the spacer 46 is connected to the flexible cable 112 provided at the end portion of the sensor substrate 12, and the other end of the spacer 46 is connected to the end portion of the reinforcement member 50 through the bonding layer 47. By using the spacer 46 to support the end portion of the reinforcement member 50 that extends so as to form the space between itself and the sensor substrate 12, detachment of the reinforcement member 50 can be suppressed. Moreover, the bending suppression effect from the reinforcement member 50 can be caused to act as far as the vicinity of the end portion of the sensor substrate 12.

Figure 31:
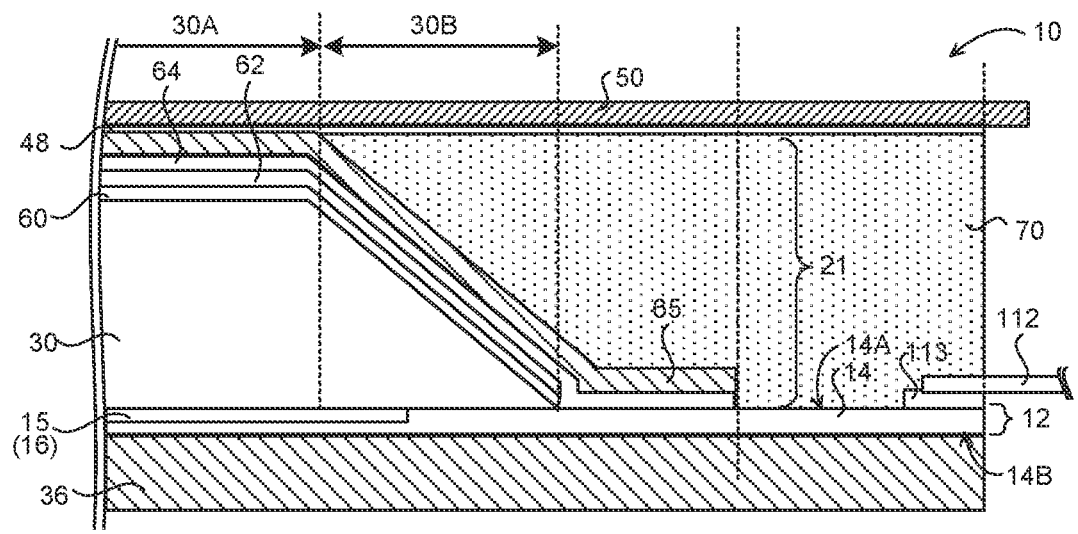
FIG. 31 is a cross-section illustrating an example of configuration of a radiation detector of an exemplary embodiment of technology disclosed herein.

In the example illustrated in FIG. 31, the filler 70 is filled into the space formed between the conversion layer 30 (the protective layer 65) and the reinforcement member 50, and between the sensor substrate 12 and the reinforcement member 50. In the present exemplary embodiment, the connection portions between the flexible cable 112 and the terminals 113 are covered by the filler 70. By filling the filler 70 into the space formed between the conversion layer 30 (the protective layer 65) and the reinforcement member 50 and between the sensor substrate 12 and the reinforcement member 50 in this manner, the reinforcement member 50 can be better suppressed from detaching from the conversion layer 30 (the protective layer 65) than in the embodiment illustrated in FIG. 29. Furthermore, due to the conversion layer 30 having a structure fixed to the sensor substrate 12 by both the reinforcement member 50 and the filler 70, the conversion layer 30 can be suppressed from detaching from the sensor substrate 12. Moreover, since the connection portions between the flexible cable 112 and the terminals 113 are covered by the filler 70, detachment of the flexible cable 112 can be suppressed.

Figure 32:
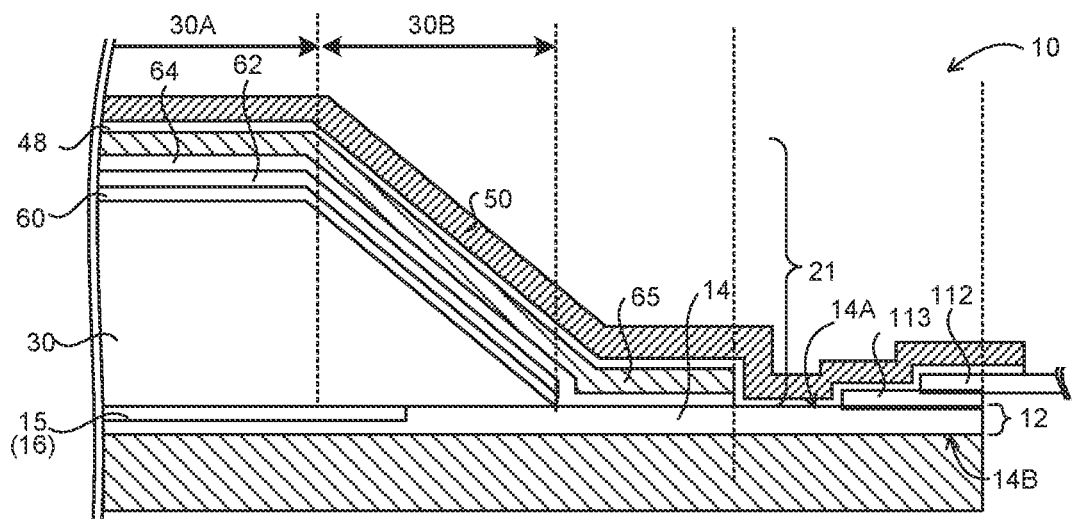
FIG. 32 is a cross-section illustrating an example of configuration of a radiation detector of an exemplary embodiment of technology disclosed herein.

In the example illustrated in FIG. 32, the outer peripheral portion of the reinforcement member 50 is angled so as to follow the slope of the peripheral edge portion 30B of the conversion layer 30. The outer peripheral portion of the reinforcement member 50 also covers the portion where the bonding layer 64 and the protective layer 65 cover the sensor substrate 12, the portion on the substrate at the outside thereof, and the connection portions between the flexible cable 112 and the terminals 113. The portions of the reinforcement member 50 extending over the sensor substrate 12 and over the flexible cable 112 are respectively bonded to the sensor substrate 12 and the flexible cable 112 through the bonding layer 48. By covering the connection portions between the flexible cable 112 and the terminals 113 with the reinforcement member 50, detachment of the flexible cable 112 can be suppressed. Moreover, since the other end of the flexible cable 112 is anticipated to be connected to a control board mounted with electronic components, there is a concern regarding comparatively large bending of the sensor substrate 12 at the connection portions between the flexible cable 112 and the terminals 113. Since the connection portions between the flexible cable 112 and the terminals 113 are covered by the reinforcement member 50, such bending of the sensor substrate 12 at these portions can be suppressed.

Figure 33:
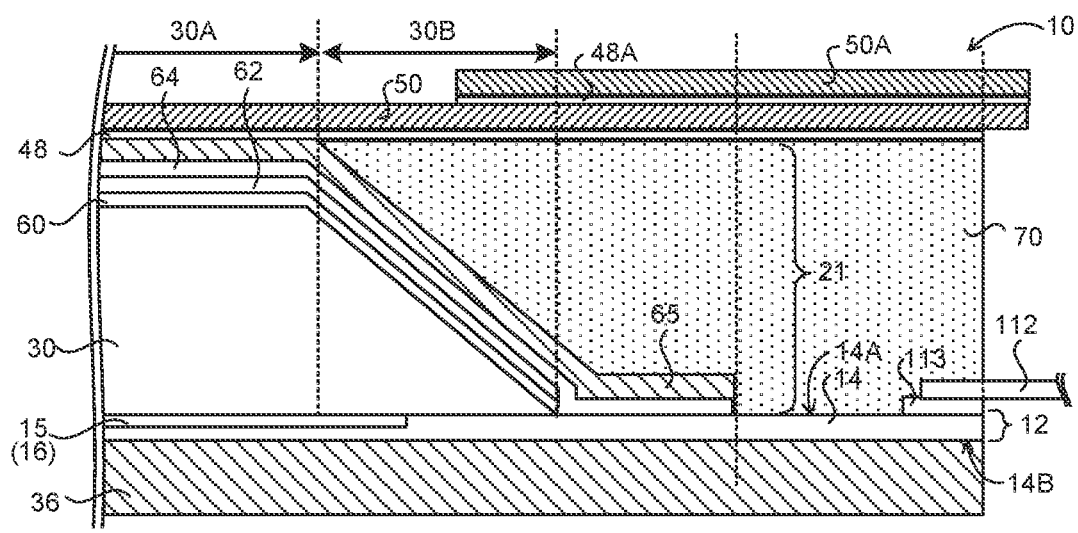
FIG. 33 is a cross-section illustrating an example of configuration of a radiation detector of an exemplary embodiment of technology disclosed herein.
Figure 34:
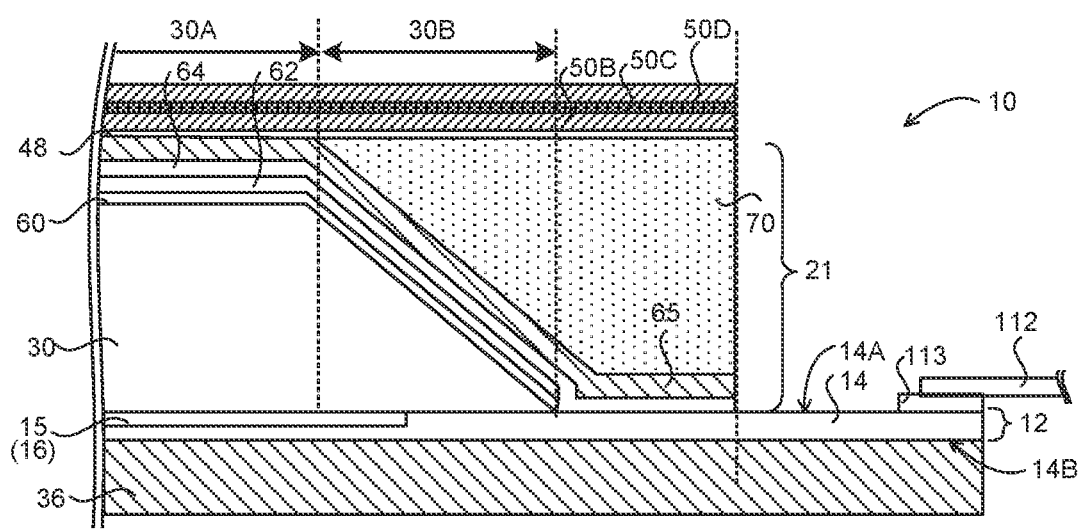
FIG. 34 is a cross-section illustrating an example of configuration of a radiation detector of an exemplary embodiment of technology disclosed herein.

In the example illustrated in FIG. 33, the filler 70 is filled into the space formed between the conversion layer 30 (the protective layer 65) and the reinforcement member 50 and between the sensor substrate 12 and the reinforcement member 50. Moreover, the additional and separate reinforcement member 50A is stacked on the front surface of the reinforcement member 50 at the region corresponding to the end portion of the conversion layer 30, with the bonding layer 48A interposed therebetween. More specifically, the reinforcement member 50A is provided in a region straddling the end portion (outer edge, edge) of the conversion layer 30. The reinforcement member 50A may be configured from the same materials as the reinforcement member 50. In the radiation detector 10, the amount of bending of the sensor substrate 12 is comparatively large at the end portion of the conversion layer 30. Forming a multi-layer structure using the reinforcement members 50 and 50A at the region corresponding to the end portion of the conversion layer 30 enables the effect of suppressing bending of the sensor substrate 12 to be enhanced at the end portion of the conversion layer 30.

As described above, in processes to manufacture the radiation detector 10, the flexible sensor substrate 12 is stuck to the support body 200, for example a glass substrate, with the detachment layer 202 interposed therebetween. After stacking the conversion layer 30 onto the sensor substrate 12, the support body 200 is detached from the sensor substrate 12. Bending occurs in the flexible sensor substrate 12 when this is performed, and so there is a concern that the pixels 16 formed on the sensor substrate 12 might be damaged thereby. By stacking the reinforcement member 50 on the conversion layer 30 as in the embodiments illustrated in the examples of FIG. 13 to FIG. 33 prior to detaching the support body 200 from the sensor substrate 12, the bending of the sensor substrate 12 that occurs when the support body is being detached from the sensor substrate 12 can be suppressed, enabling the risk of damage of the pixels 16 to be reduced.

Moreover, the reinforcement member 50 is not limited to a single layer (one layer), and may be configured with multiple layers. For example, in the radiation detector 10 in the example illustrated in FIG. 34, the reinforcement member 50 is a multi-layered film configured of three layers in which a first reinforcement member 50B, a second reinforcement member 50C, and a third reinforcement member 50D are stacked in sequence from the side closest to the conversion layer 30.

In cases in which the reinforcement member 50 has multiple layers, each of the layers included in the reinforcement member 50 preferably has a different function. For example, in the example illustrated in FIG. 34, the first reinforcement member 50B and the third reinforcement member 50D may be configured as layers having a non-conductive anti-static function, while the second reinforcement member 50C is configured as a conductive layer such that the reinforcement member 50 has an electromagnetic shielding function. In such cases, the first reinforcement member 50B and the third reinforcement member 50D may employ an anti-static film such as a film employing the anti-static coating COLCOAT (trade name, manufactured by COLCOAT Co., Ltd.). The second reinforcement member 50C may employ a conductive sheet or a conductive mesh sheet made of Cu or the like.

Figure 52:
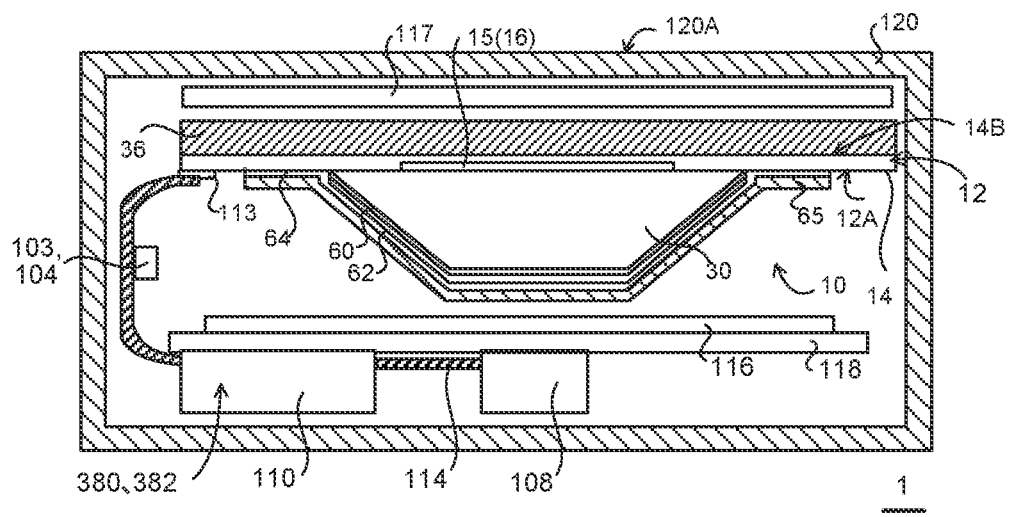
FIG. 52 is a cross-section illustrating an example of configuration of a radiographic imaging device of an exemplary embodiment of technology disclosed herein.

For example, in cases in which the reading approach of the radiation detector 10 is an ISS approach, the control board 110, the power source 108, and the like may be provided on the conversion layer 30 side (see FIG. 52). Providing the reinforcement member 50 with an anti-static function in this manner enables electromagnetic noise from the control board 110 and the power source 108 to be shielded.

Figure 35:
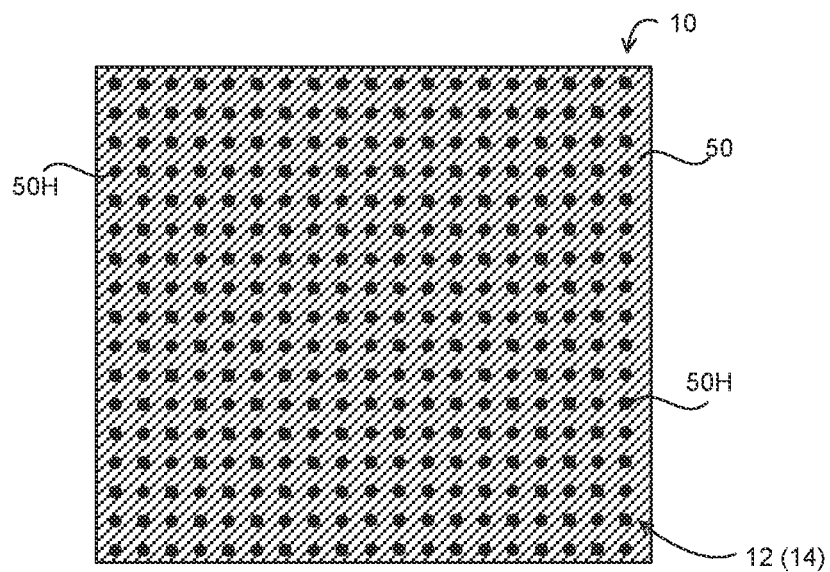
FIG. 35 is a plan view illustrating an example of a structure of a reinforcement member of an exemplary embodiment of technology disclosed herein.

FIG. 35 is a plan view illustrating an example of a structure of the reinforcement member 50. A main face of the reinforcement member 50 may include plural through holes 50H. The size and pitch of the through holes 50H is prescribed so as to obtain the desired rigidity of the reinforcement member 50.

Including the plural through holes 50H in the reinforcement member 50 enables air introduced at the joining face of the reinforcement member 50 to the conversion layer 30 to escape through the through holes 50H. This enables air bubbles to be suppressed from being generated at the joining face of the reinforcement member 50 to the conversion layer 30.

There is a concern that air bubbles might be generated at the joining face if no mechanism is provided to allow air introduced at the joining face of the reinforcement member 50 to the conversion layer 30 to escape. For example, were air bubbles generated at the joining face to expand due to heat during operation of the radiographic imaging device 1, there would be a drop in the cohesion between the reinforcement member 50 and the conversion layer 30. This would lead to a concern that the bending suppression effect from the reinforcement member 50 might not be sufficiently exhibited. By using the reinforcement member 50 including the plural through holes 50H as illustrated in FIG. 35, the generation of air bubbles at the joining face of the reinforcement member 50 to the conversion layer 30 can be suppressed as described above, enabling the cohesion between the reinforcement member 50 and the conversion layer 30 to be maintained. This enables the bending suppression effect of the reinforcement member 50 to be maintained.

Figure 36:
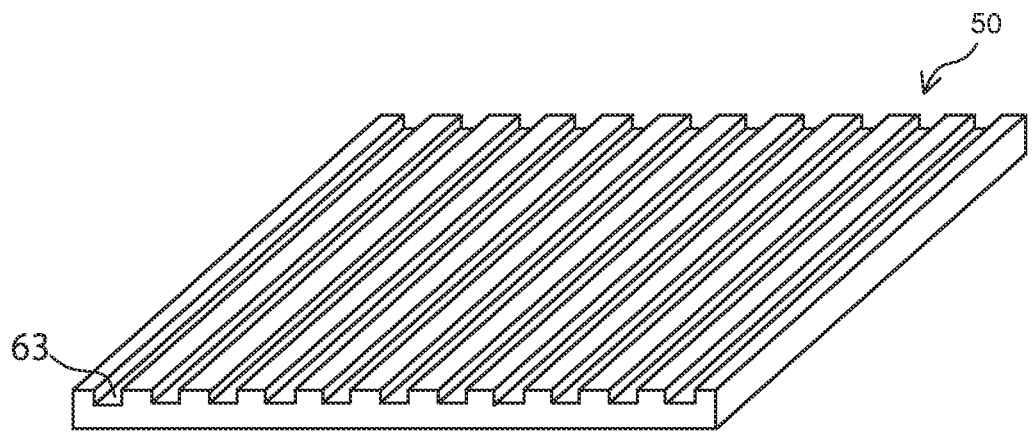
FIG. 36 is a perspective view illustrating an example of a structure of a reinforcement member of an exemplary embodiment of technology disclosed herein.
Figure 37:
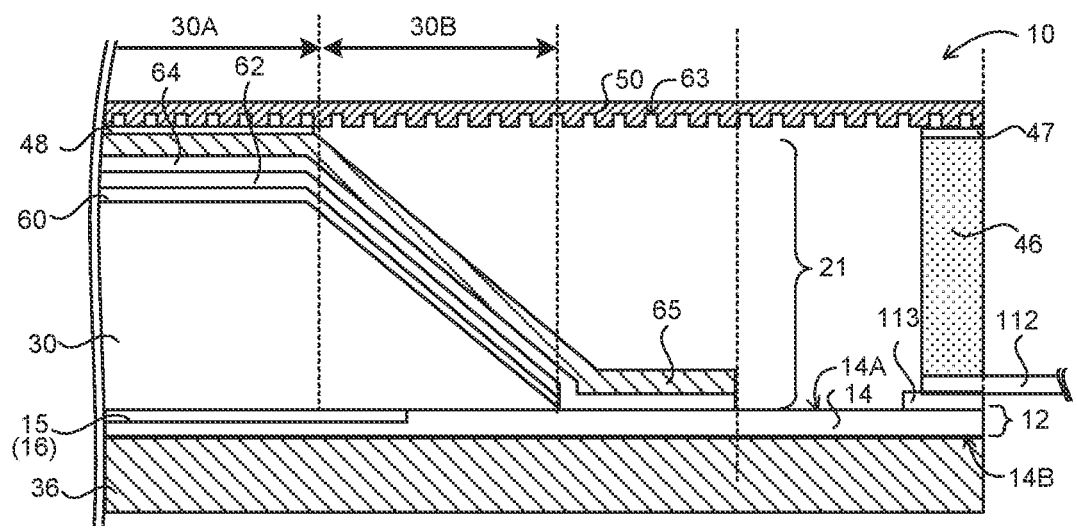
FIG. 37 is a cross-section illustrating an example of configuration of a radiation detector according to an exemplary embodiment of technology disclosed herein.

FIG. 36 is a perspective view illustrating another example of the structure of the reinforcement member 50. In the example illustrated in FIG. 36, the reinforcement member 50 includes an indented-and-protruding structure on the joining face to the conversion layer 30. The indented-and-protruding structure may be configured including plural grooves 63 arranged parallel to each other, as illustrated in FIG. 36. The face of the reinforcement member 50 that includes the indented-and-protruding structure configured from the plural grooves 63 is, for example as illustrated in FIG. 37, joined to the conversion layer 30 that has been covered by the reflective layer 62. Due to the reinforcement member 50 including the indented-and-protruding structure on the joining face to the conversion layer 30 in this manner, any air introduced to the joining portion of the reinforcement member 50 and the conversion layer 30 is able to escape through the grooves 63. Similarly to in the embodiment illustrated in FIG. 35, this accordingly enables the generation of air bubbles at the joining face of the reinforcement member 50 to the conversion layer 30 to be suppressed. This enables the cohesion between the reinforcement member 50 and the conversion layer 30 to be maintained, and enables the bending suppression effect of the reinforcement member 50 to be maintained.

Figure 38:
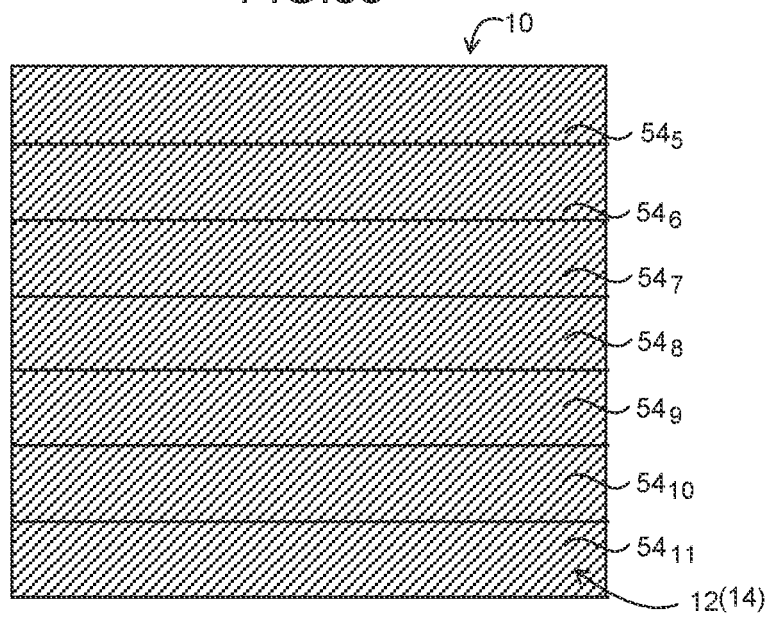
FIG. 38 is a plan view illustrating an example of a structure of a reinforcement member of an exemplary embodiment of technology disclosed herein.
Figure 39:
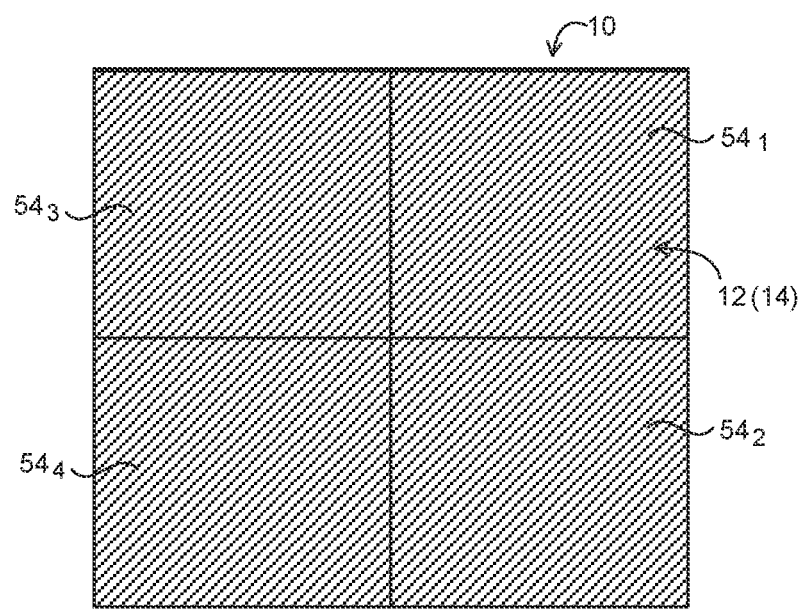
FIG. 39 is a plan view illustrating an example of a structure of a reinforcement member of an exemplary embodiment of technology disclosed herein.

FIG. 38 and FIG. 39 are plan views illustrating other examples of structures of the reinforcement member 50. As illustrated in FIG. 38 and FIG. 39, the reinforcement member 50 may be segmented into plural pieces 54. The reinforcement member 50 may, as illustrated in FIG. 38, be segmented into the plural pieces 54 (FIGS. 54$_5$ to 54$_{11}$) arrayed along one direction. Alternatively, the reinforcement member 50 may, as illustrated in FIG. 39, be segmented into the plural pieces 54 (pieces 54$_1$ to 54$_4$) arrayed in both a longitudinal direction and a lateral direction.

The greater the surface area of the reinforcement member 50, the more readily air bubbles are generated at the joining face of the reinforcement member 50 to the conversion layer 30. As illustrated in FIG. 38 and FIG. 39, segmenting the reinforcement member 50 into the plural pieces 54 enables the generation of air bubbles at the joining face of the reinforcement member 50 to the conversion layer 30 to be suppressed. This enables the cohesion between the reinforcement member 50 and the conversion layer 30 to be maintained, and thereby enables the bending suppression effect of the reinforcement member 50 to be maintained.

A reinforcement member 52 may be provided on the opposite side of the neutral stress plane adjustment member 36 to the side contacting the sensor substrate 12 (the second surface 14B). FIG. 40 to FIG. 44 are cross-sections respectively illustrating examples of embodiments of installation of the reinforcement member 52.

In the examples illustrated in FIG. 40 to FIG. 44, the reinforcement member 52 is stacked on the surface of the neutral stress plane adjustment member 36 on the opposite side to the surface on the sensor substrate 12 side, with a bonding layer 51 interposed therebetween. The reinforcement member 52 may be configured from the same materials as the reinforcement member 50. In cases in which the radiation detector 10 employs an ISS approach, the reinforcement member 52 is preferably provided only at an outer peripheral portion of the sensor substrate 12 so as to keep the surface area of locations where the reinforcement member 52 and the pixel region 15 overlap each other as small as possible. Namely, the reinforcement member 52 may have a ring shape with an opening 61 at a location corresponding to the pixel region 15, as illustrated in FIG. 40 to FIG. 44. Forming a multi-layer structure with the neutral stress plane adjustment member 36 and the reinforcement member 52 at the outer peripheral portion of the sensor substrate 12 in this manner enables the rigidity of the outer peripheral portion of the sensor substrate 12 that is comparatively susceptible to bending to be reinforced.

Figure 40:
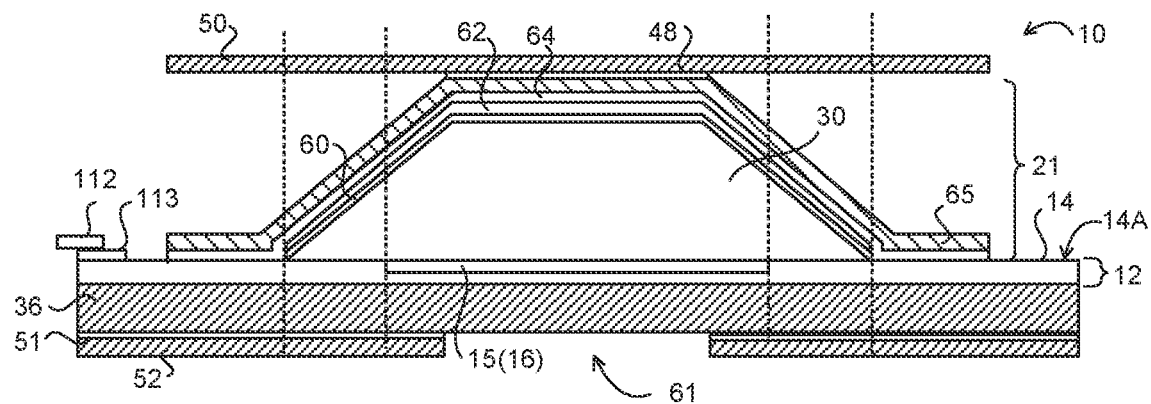
FIG. 40 is a cross-section illustrating an example of configuration of a radiation detector of an exemplary embodiment of technology disclosed herein.
Figure 41:
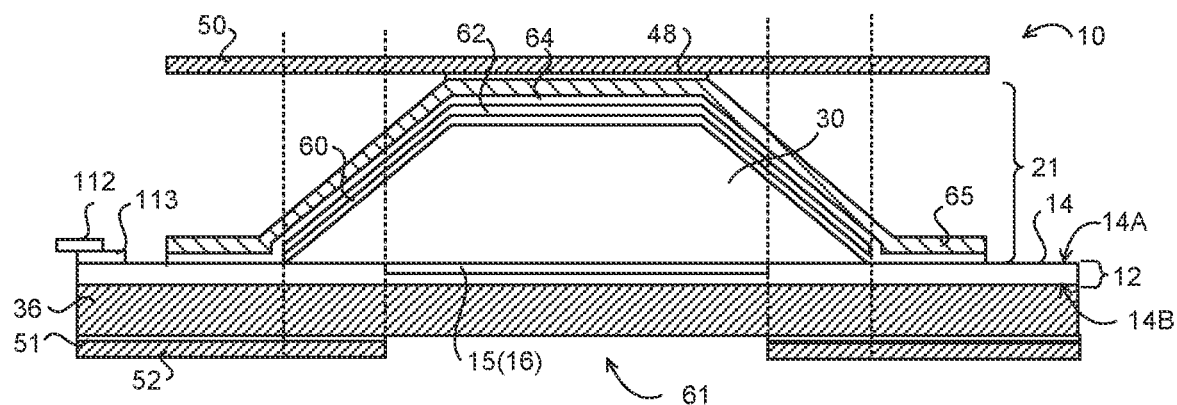
FIG. 41 is a cross-section illustrating an example of configuration of a radiation detector of an exemplary embodiment of technology disclosed herein.
Figure 42:
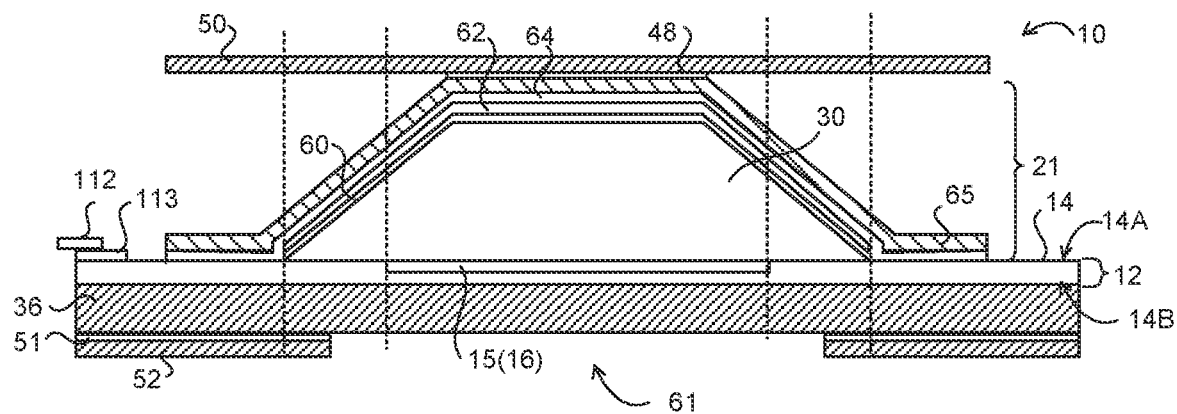
FIG. 42 is a cross-section illustrating an example of configuration of a radiation detector of an exemplary embodiment of technology disclosed herein.

In the examples illustrated in FIG. 40 to FIG. 42, the reinforcement member 52 is provided at a region straddling the end portion (outer edge, edge) of the conversion layer 30. In the radiation detector 10, the amount of bending of the sensor substrate 12 is comparatively large at the end portion of the conversion layer 30. Forming a multi-layer structure using the neutral stress plane adjustment member 36 and the reinforcement member 52 at the region corresponding to the end portion of the conversion layer 30 enables the effect of suppressing bending of the sensor substrate 12 to be enhanced at the end portion of the conversion layer 30.

In cases in which an ISS approach is employed in the radiation detector 10, there is a concern that were a portion of the reinforcement member 52 to overlap with the pixel region 15 as illustrated in FIG. 40, this might have an impact on the images, depending on the substance employed in the reinforcement member 52. Thus, in cases in which a portion of the reinforcement member 52 overlaps with the pixel region 15, a plastic is preferably employed for the material of the reinforcement member 52.

As illustrated in FIG. 41 and FIG. 42, an embodiment is most preferably adopted in which the reinforcement member 52 straddles the end portion (outer edge, edge) of the conversion layer 30 but does not overlap with the pixel region 15 (namely, an embodiment in which an edge of the opening 61 in the reinforcement member 52 is disposed at the outside of the pixel region 15). In the example illustrated in FIG. 41, the position of the edge of the opening 61 in the reinforcement member 52 is substantially aligned with the position of the end portion of the pixel region 15. In the example illustrated in FIG. 42, the edge of the opening 61 in the reinforcement member 52 is disposed between the end portion of the pixel region 15 and the end portion of the conversion layer 30.

Figure 43:
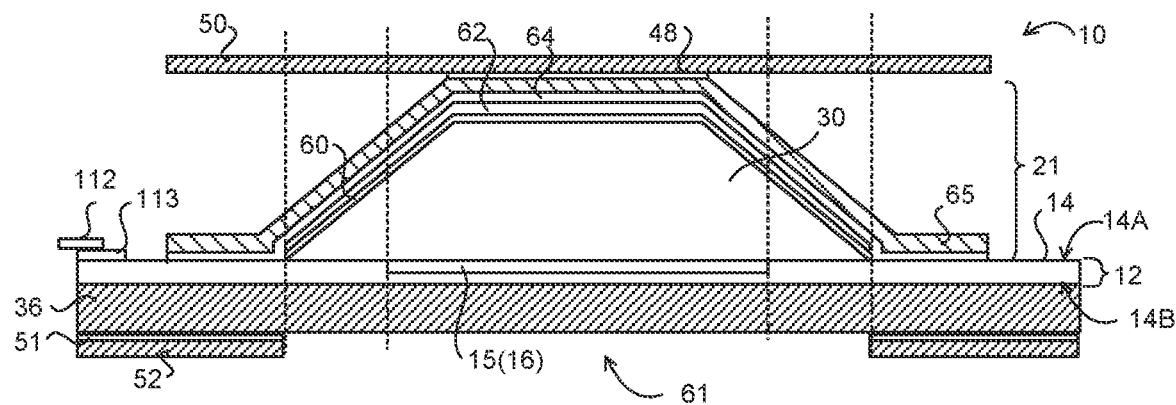
FIG. 43 is a cross-section illustrating an example of configuration of a radiation detector of an exemplary embodiment of technology disclosed herein.
Figure 44:
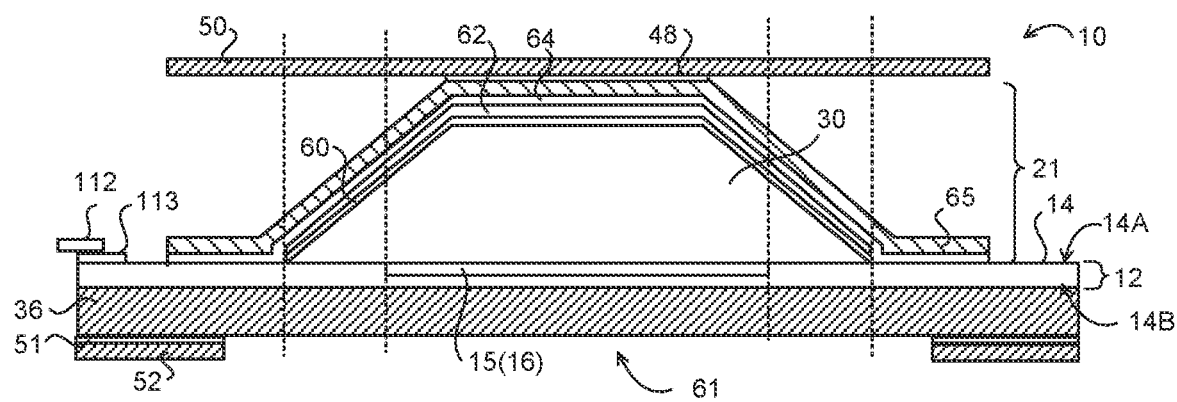
FIG. 44 is a cross-section illustrating an example of configuration of a radiation detector of an exemplary embodiment of technology disclosed herein.

Moreover, the position of the edge of the opening 61 in the reinforcement member 52 may be disposed so as to be substantially aligned with the position of the end portion of the conversion layer 30 as illustrated in FIG. 43, or may be disposed so as to be further outside than the end portion of the conversion layer 30 as illustrated in FIG. 44. In such cases, there is no structure present where the reinforcement member 52 straddles the end portion (outer edge, edge) of the conversion layer 30, and so there might be a concern regarding a lessening of the effect of suppressing bending of the sensor substrate 12 at the end portion of the conversion layer 30. However, due to forming a stacked structure using the neutral stress plane adjustment member 36 and the reinforcement member 52 at the outer peripheral portion of the sensor substrate 12 where the connection portions between the flexible cable 112 and the terminals 113 are present, the effect of suppressing bending of the sensor substrate 12 at the connection portions between the flexible cable 112 and the terminals 113 is maintained.

In the radiation detectors 10 of the exemplary embodiments described above, explanation has been given regarding embodiments in which the size of the sensor substrate 12 (base member 14) and the size of the neutral stress plane adjustment member 36 are the same as each other. However, the size of the sensor substrate 12 and the size of the neutral stress plane adjustment member 36 may be different to each other.

For example, in cases in which the radiation detector 10 is applied to the radiographic imaging device 1, the radiation detector 10 may be employed fixed to the case 120 (see FIG. 7, etc.) or the like that houses the radiation detector 10. In such cases, as in the example illustrated in FIG. 45A, the neutral stress plane adjustment member 36 may be made larger than the sensor substrate 12 and provided with a flap or the like in order to fix the radiation detector 10 using the locations of the flap or the like. For example, an embodiment may be configured in which holes are provided in a flap portion of the neutral stress plane adjustment member 36, and screws are passed through the holes to fix the neutral stress plane adjustment member 36 to the case 120 (see FIG. 7, etc.)

Figure 45A:
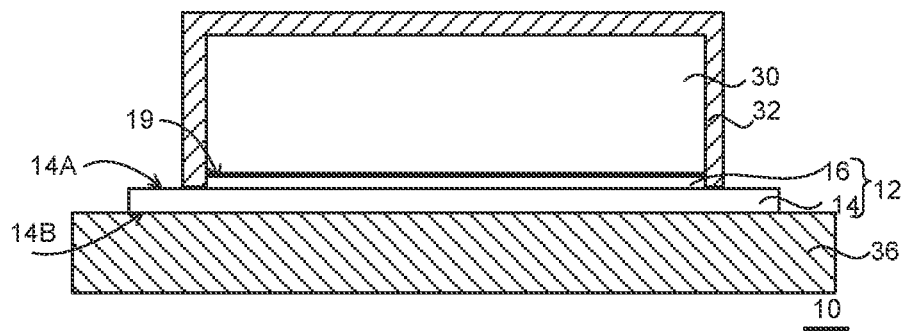
FIG. 45A is a cross-section illustrating an example of configuration of a radiation detector of an exemplary embodiment of technology disclosed herein.
Figure 45B:
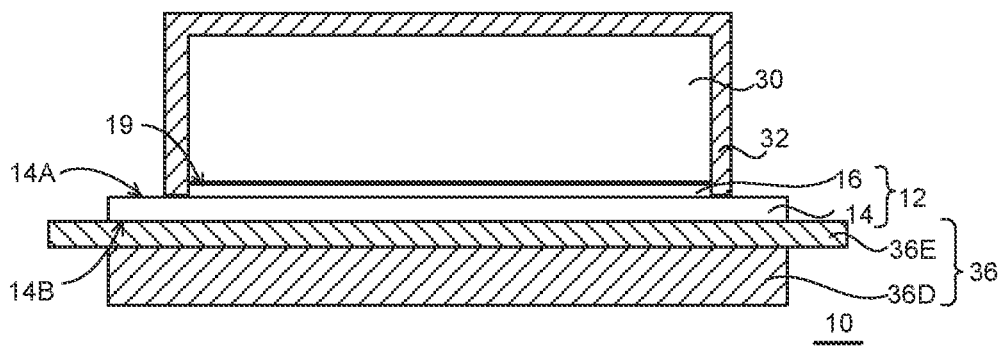
FIG. 45B is a cross-section illustrating an example of configuration of a radiation detector of an exemplary embodiment of technology disclosed herein.

Note that embodiments in which the neutral stress plane adjustment member 36 is larger than the sensor substrate 12 are not limited to the embodiment illustrated in FIG. 45A. An embodiment may be configured in which the neutral stress plane adjustment member 36 is configured with plural stacked layers, with some of these layers being larger than the sensor substrate 12. For example, as illustrated in FIG. 45B, the neutral stress plane adjustment member 36 may be configured with a dual-layer structure including a first layer 36D of similar size to the sensor substrate 12 (the base member 14) and a second layer 36E that is larger than the sensor substrate 12. The first layer 36D is stuck to the second layer 36E using double-sided tape, an adhesion layer, or the like (not illustrated in the drawings). For example, the first layer 36D is preferably formed of similar materials to those of the neutral stress plane adjustment member 36 described above so as to possess similar properties to the neutral stress plane adjustment member 36. The second layer 36E is stuck to the second surface 14B of the base member 14 using double-sided tape, an adhesion layer, or the like (not illustrated in the drawings). For example, ALPET (registered trademark) may be applied as the second layer 36E. In cases in which the neutral stress plane adjustment member 36 is configured with plural layers, conversely to the embodiment illustrated in FIG. 45B, an embodiment may be configured in which the first layer 36D is stuck to the second surface 14B of the base member 14, as illustrated in FIG. 45C.

As described above, in cases in which the radiation detector 10 is fixed to the case 120 (see FIG. 7, etc.) or the like using a flap or the like provided to the neutral stress plane adjustment member 36, such fixing may be performed in a state in which the flap portion is bent. The thinner the thickness thereof, the more easily the flap portion of the neutral stress plane adjustment member 36 will bend, enabling the flap portion alone to be bent without affecting the main body of the radiation detector 10. Accordingly, in cases in which the flap portion or the like is to be bent, an embodiment in which the neutral stress plane adjustment member 36 is configured of plural stacked layers with some of these layers being configured larger than the sensor substrate 12 as illustrated in the examples of FIG. 45B and FIG. 45C is preferable.

Figure 45C:
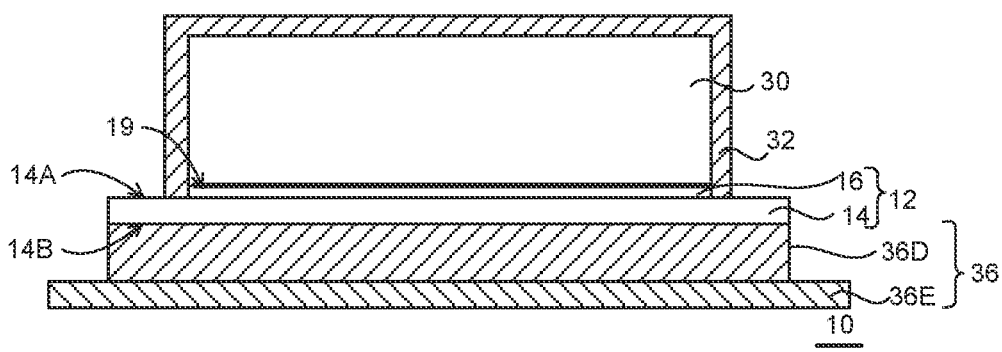
FIG. 45C is a cross-section illustrating an example of configuration of a radiation detector of an exemplary embodiment of technology disclosed herein.
Figure 46:
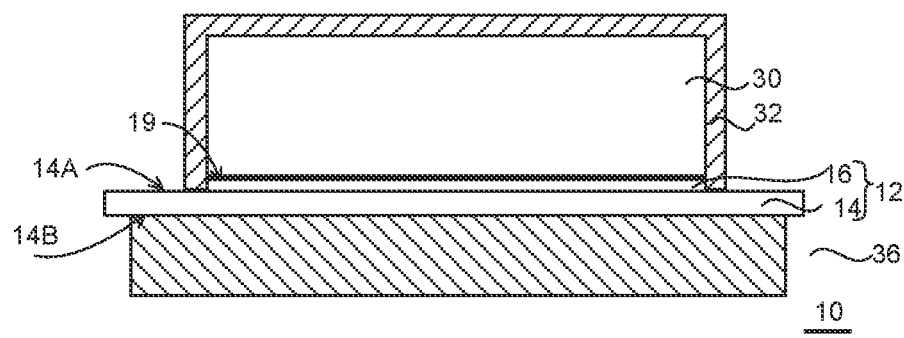
FIG. 46 is a cross-section illustrating an example of configuration of a radiation detector of an exemplary embodiment of technology disclosed herein.

As in the example illustrated in FIG. 46, conversely to the radiation detectors 10 in FIG. 45A to FIG. 45C, the neutral stress plane adjustment member 36 may be smaller than the sensor substrate 12. Positioning an end portion of the sensor substrate 12 at the outside of an end portion of the neutral stress plane adjustment member 36 facilitates checking of the position of the end portion of the sensor substrate 12 during assembly, for example when housing the radiation detector 10 inside the case 120 (see FIG. 7, etc.), thus enabling positioning precision to be improved. Note that there is no limitation to the embodiment illustrated in FIG. 46, since as long as at least a portion of the end portion of the sensor substrate 12 (the base member 14) is positioned at the outside of the neutral stress plane adjustment member 36, similar advantageous effects can be obtained and is therefore preferable.

Explanation follows regarding examples of the radiographic imaging device 1 in which the radiation detector 10 is housed inside the case 120, with reference to FIG. 47 to FIG. 53. FIG. 47 to FIG. 53 are diagrams illustrating other configuration examples of the radiographic imaging device 1.

Figure 47:
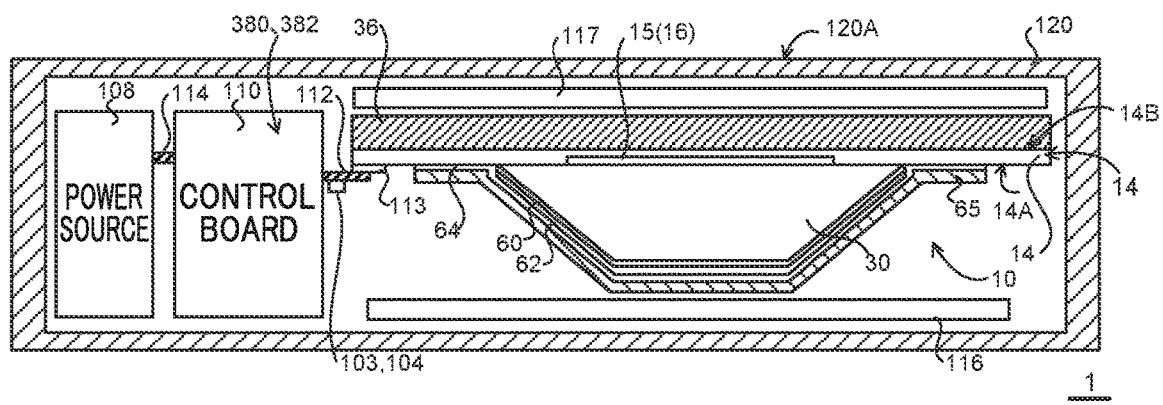
FIG. 47 is a cross-section illustrating an example of configuration of a radiographic imaging device of an exemplary embodiment of technology disclosed herein.
Figure 48:
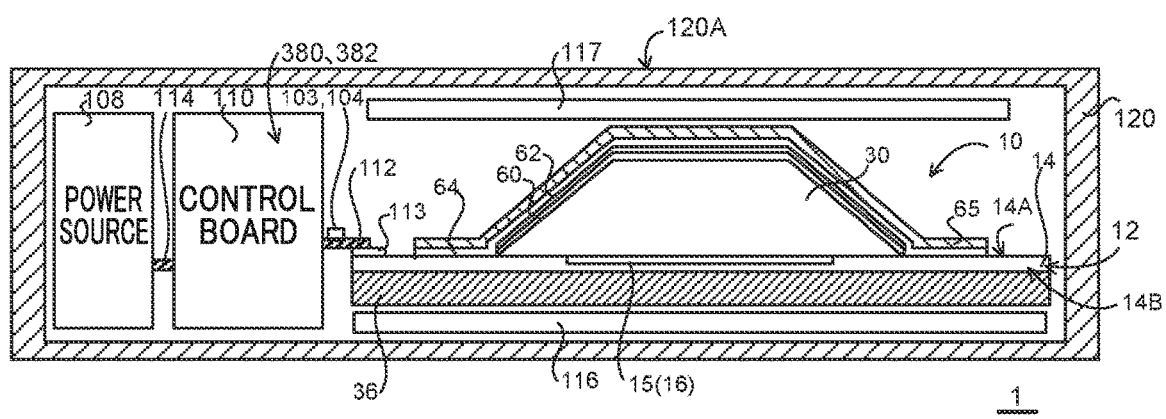
FIG. 48 is a cross-section illustrating an example of configuration of a radiographic imaging device of an exemplary embodiment of technology disclosed herein.
Figure 49:
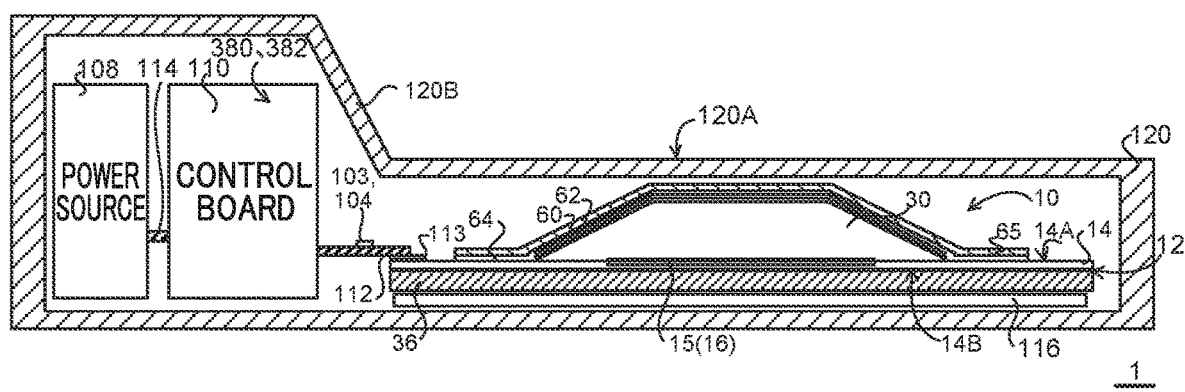
FIG. 49 is a cross-section illustrating an example of configuration of a radiographic imaging device of an exemplary embodiment of technology disclosed herein.
Figure 50:
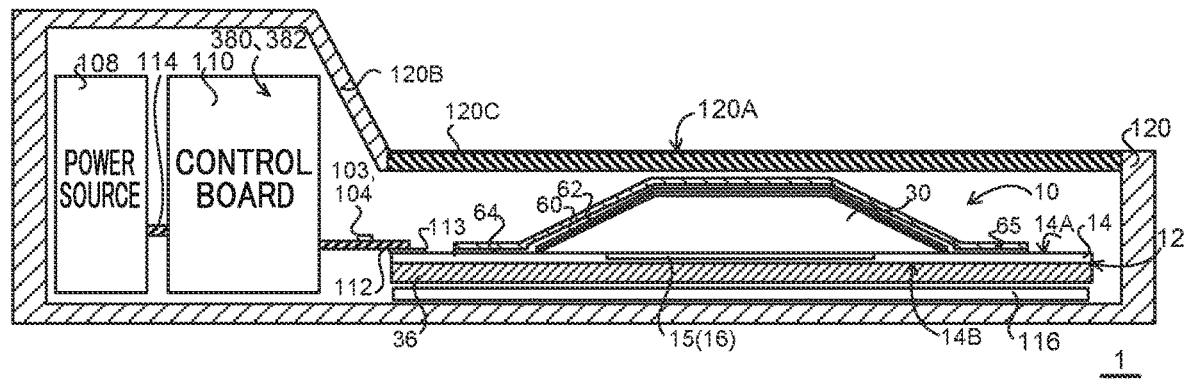
FIG. 50 is a cross-section illustrating an example of configuration of a radiographic imaging device of an exemplary embodiment of technology disclosed herein.

The example illustrated in FIG. 47 is a radiographic imaging device 1 employing an ISS approach, similarly to the radiographic imaging device 1 illustrated in FIG. 7. The example illustrated in FIG. 48 is a radiographic imaging device 1 employing a PSS approach. In the examples illustrated in FIG. 47 and FIG. 48, the radiation detector 10, the control board 110, and the power source 108 are arranged alongside one another in the lateral direction of the respective drawings.

In the examples illustrated in FIG. 47 and FIG. 48, a protective layer 117 is further provided between the radiation detector 10 and an inner wall of the imaging face 120A of the case 120. In other words, the protective layer 117 is further provided on the imaging face 120A side, this being the side to which the radiation R is incident. The protective layer 117 may, for example, be configured by a moisture-proof film such as an ALPET (registered trademark) sheet in which an aluminum layer such as an aluminum foil is bonded to an insulating sheet (film), or an insulating sheet such as a Parylene (registered trademark) film or polyethylene terephthalate. The protective layer 117 has a moisture-proof function and an anti-static function with respect to the pixel region 15. Accordingly, the protective layer 117 preferably covers at least the entire face of the pixel region 15 on the side to which the radiation R is incident, and preferably covers the entire face of the sensor substrate 12 on the side to which the radiation R is incident.

Note that FIG. 47 and FIG. 48 illustrate embodiments in which both the power source 108 and the control board 110 are provided on one side of the radiation detector 10, specifically on the side of one edge of the rectangular pixel region 15. However, the positions at which the power source 108 and the control board 110 are provided are not limited to those of the embodiments illustrated in FIG. 47 and FIG. 48. For example, the power source 108 and the control board 110 may be provided distributed between two opposing edges of the pixel region 15, or may be provided distributed between two adjacent edges of the pixel region 15.

As in the examples illustrated in FIG. 47 and FIG. 48, in cases in which the radiation detector 10, the control board 110, and the power source 108 are arranged in a direction intersecting the direction in which the sensor substrate 12 and the conversion layer 30 are stacked (the stacking direction P), the thickness of the case 120 may be varied between the locations of the case 120 where the power source 108 and the control board 110 are respectively provided, and the location of the case 120 where the radiation detector 10 is provided.

The power source 108 and the control board 110 are often each thicker than the radiation detector 10, as in the example illustrated in FIG. 48. In such cases, as in the example illustrated in FIG. 49, the thickness of the location of the case 120 where the radiation detector 10 is provided may be less than the thickness of the locations of the case 120 where the power source 108 and the control board 110 are provided. In cases in which the thickness is varied between the locations of the case 120 where the power source 108 and the control board 110 are respectively provided and the location of the case 120 where the radiation detector 10 is provided in this manner, since there might be a concern of causing discomfort to the imaging subject who touches a boundary 120B where a step is created at a boundary between these locations, the boundary 120B is preferably provided with a slope.

So doing enables an ultra-thin portable electronic cassette to be configured according to the thickness of the radiation detector 10.

As another example, in such cases, the case 120 may be configured of different materials at the locations of the case 120 where the power source 108 and the control board 110 are provided and the location of the case 120 where the radiation detector 10 is provided. Moreover, for example, the locations of the case 120 where the power source 108 and the control board 110 are provided and the location of the case 120 where the radiation detector 10 is provided may be configured separately to each other.

Moreover, as described above, the case 120 preferably has a low absorption ratio of the radiation R, in particular X-rays, and high rigidity, and is preferably configured from a material that has a sufficiently high elastic modulus. However, as in the example illustrated in FIG. 50, a location 120C of the case 120 corresponding to the imaging face 120A may be configured with a low absorption ratio to the radiation R and high rigidity, and be configured from a material that has a sufficiently high elastic modulus, while other locations of the case 120 are configured from a different material than the location 120C, for example a material having a lower elastic modulus than the location 120C.

Figure 51:
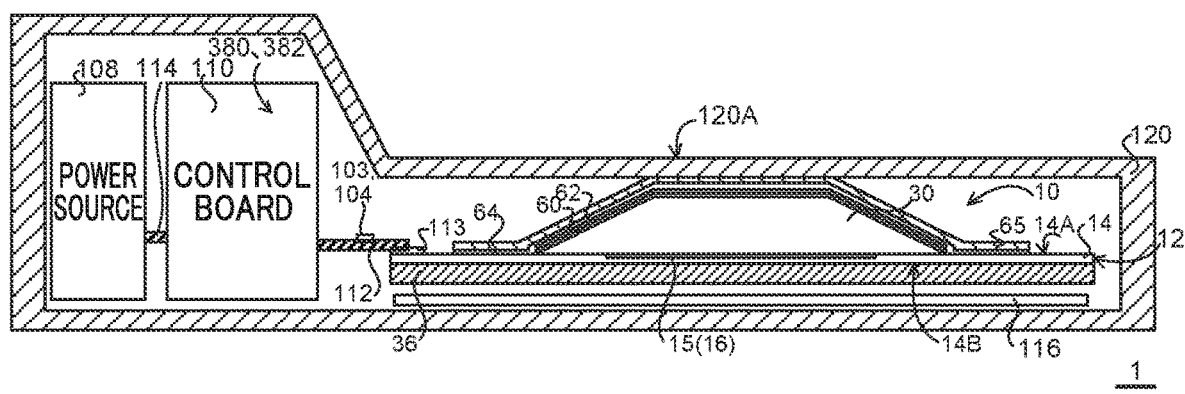
FIG. 51 is a cross-section illustrating an example of configuration of a radiographic imaging device of an exemplary embodiment of technology disclosed herein.

Alternatively, the radiation detector 10 and an inner wall face of the case 120 may contact each other as in the example illustrated in FIG. 51. In such cases, the radiation detector 10 and the inner wall face of the case 120 may be bonded through a bonding layer, or may simply be in contact with each other without providing a bonding layer. Such contact between the radiation detector 10 and the inner wall face of the case 120 further secures the rigidity of the radiation detector 10.

Figure 53:
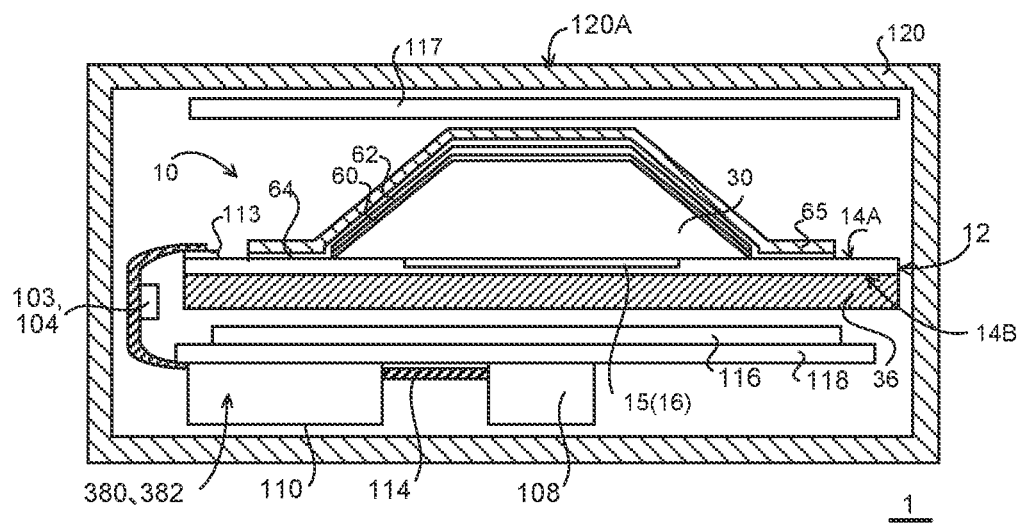
FIG. 53 is a cross-section illustrating an example of configuration of a radiographic imaging device of an exemplary embodiment of technology disclosed herein.

FIG. 52 illustrates an example of a radiographic imaging device 1 employing an ISS approach, similarly to the radiographic imaging device 1 illustrated in FIG. 8. FIG. 53 illustrates an example of a radiographic imaging device 1 employing a PSS approach. In the examples illustrated in FIG. 52 and FIG. 53, the sensor substrate 12 is provided on one side, and the control board 110 and the power source 108 are provided on the other side of the sheet 116 and the base 118. This configuration enables the size of the radiographic imaging device 1 in plan view to be reduced in comparison to cases in which the radiation detector 10, the control board 110, and the power source 108 are arranged in the lateral direction in the drawings (see FIG. 47 to FIG. 51).

Figure 54:
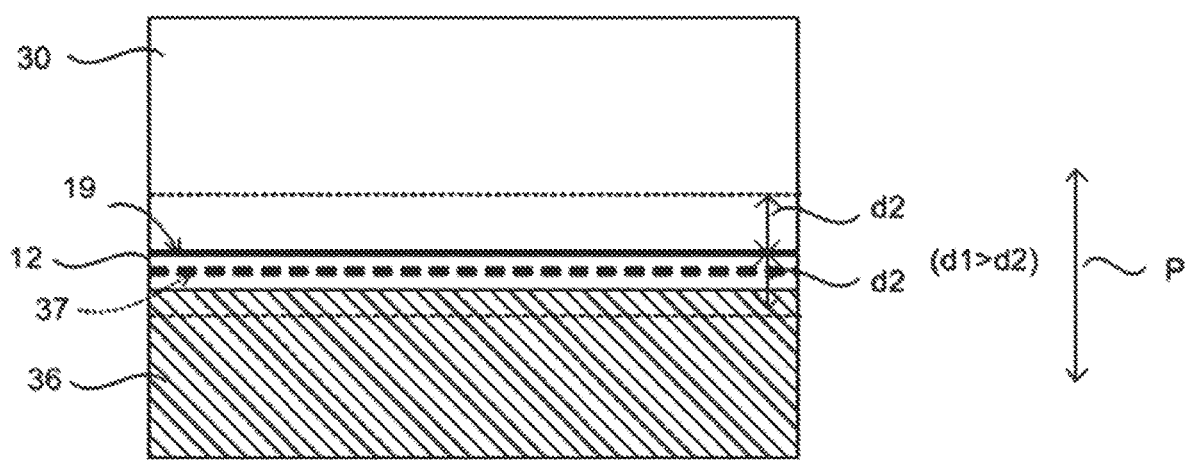
FIG. 54 is a schematic diagram to explain a position of a neutral stress plane.

In the exemplary embodiments described above, explanation has been given regarding embodiments in which the position of the neutral stress plane 37 is preferably at the position of the interface 19. However, the preferable position of the neutral stress plane 37 is not limited to the position of the interface 19. In cases in which the cohesion between the conversion layer 30 and the sensor substrate 12 is comparatively high, the TFTs 20, the sensor sections 22, and the like of the sensor substrate 12 may sustain damage before the conversion layer 30 detaches from the sensor substrate 12. In such cases in which the cohesion between the conversion layer 30 and the sensor substrate 12 is comparatively high, as illustrated in FIG. 54 the neutral stress plane adjustment member 36 is preferably used to set the position of the neutral stress plane 37 at a position within the sensor substrate 12 side within the predetermined range described above.

All cited documents, patent applications, and technical standards mentioned in the present specification are incorporated by reference in the present specification to the same extent as if each individual cited document, patent application, or technical standard was specifically and individually indicated to be incorporated by reference.

A radiation detector of a second aspect of the present disclosure is the radiation detector of the first aspect, wherein the predetermined range is a range that is shorter than a distance between the interface and the neutral stress plane in cases in which the neutral stress plane adjustment member is not provided.

A radiation detector of a third aspect of the present disclosure is the radiation detector of the first aspect or the second aspect, wherein the neutral stress plane adjustment member is provided at a region covering at least a region where the sensor substrate and the conversion layer oppose each other.

A radiation detector of a fourth aspect of the present disclosure is the radiation detector of any one of the first aspect to the third aspect, wherein the neutral stress plane adjustment member has a bending elastic modulus of from 150 MPa to 2500 MPa.

A radiation detector of a fifth aspect of the present disclosure is the radiation detector of any one of the first aspect to the fourth aspect, wherein a material of the neutral stress plane adjustment member includes at least one material out of polycarbonate, polyethylene terephthalate, or low density polyethylene.

A radiation detector of a sixth aspect of the present disclosure is the radiation detector of any one of the first aspect to the fifth aspect, wherein a ratio of a coefficient of thermal expansion of the neutral stress plane adjustment member with respect to a coefficient of thermal expansion of the conversion layer is from 0.5 to 4.

A radiation detector of a seventh aspect of the present disclosure is the radiation detector of any one of the first aspect to the sixth aspect, wherein the neutral stress plane adjustment member has a coefficient of thermal expansion of from 30 ppm/K to 200 ppm/K.

A radiation detector of an eighth aspect of the present disclosure is the radiation detector of any one of the first aspect to the seventh aspect, further including a cohesion layer provided at the interface and contacting the sensor substrate and the conversion layer.

A radiation detector of a ninth aspect of the present disclosure is the radiation detector of any one of the first aspect to the seventh aspect, further including a buffer layer provided between the sensor substrate and the conversion layer, and configured to buffer a difference between a coefficient of thermal expansion of the conversion layer and a coefficient of thermal expansion of the sensor substrate.

A radiation detector of a tenth aspect of the present disclosure is the radiation detector of any one of the first aspect to the ninth aspect, wherein the neutral stress plane adjustment member includes plural films stacked along the stacking direction, the plural films having different functions to each other.

A radiation detector of an eleventh aspect of the present disclosure is the radiation detector of the tenth aspect, wherein the plural films include a neutral stress plane adjustment film and an anti-static film.

A radiation detector of a twelfth aspect of the present disclosure is the radiation detector of the eleventh aspect, wherein the anti-static film is provided further toward the second surface side than the neutral stress plane adjustment film.

A radiation detector of a thirteenth aspect of the present disclosure is the radiation detector of the tenth aspect, wherein the plural films include a neutral stress plane adjustment film and a moisture-proof film.

A radiation detector of a fourteenth aspect of the present disclosure is the radiation detector of the thirteenth aspect, wherein the moisture-proof film is provided further toward the second surface side than the neutral stress plane adjustment film.

A radiation detector of a fifteenth aspect of the present disclosure is the radiation detector of any one of the first aspect to the fourteenth aspect, wherein the base member is made of resin and includes a fine particle layer containing inorganic fine particles having a mean particle size of from 0.05 μm to 2.5 μm.

A radiation detector of a sixteenth aspect of the present disclosure is the radiation detector of the fifteenth aspect, wherein the base member includes the fine particle layer on the second surface side.

A radiation detector of a seventeenth aspect of the present disclosure is the radiation detector of the fifteenth aspect or the seventeenth aspect, wherein the fine particles include an element having an atomic number that is greater than an atomic number of elements configuring the base member and that is an atomic number not exceeding 30.

A radiation detector of an eighteenth aspect of the present disclosure is the radiation detector of any one of the first aspect to the seventeenth aspect, wherein the base member has a coefficient of thermal expansion not greater than 20 ppm/K in a temperature range from 300° C. to 400° C.

A radiation detector of a nineteenth aspect of the present disclosure is the radiation detector of any one of the first aspect to the eighteenth aspect, wherein the base member satisfies at least one condition out of having a heat shrinkage ratio in a machine direction at 400° C. and at a thickness of 25 μm of not greater than 0.5%, or having a modulus of elasticity at 500° C. of not less than 1 GPa.

A radiation detector of a twentieth aspect of the present disclosure is the radiation detector of any one of the first aspect to the nineteenth aspect, wherein the neutral stress plane adjustment member has a higher rigidity than the base member.

A radiation detector of a twenty-first aspect of the present disclosure is the radiation detector of any one of the first aspect to the twentieth aspect, wherein the conversion layer includes CsI.

A radiographic imaging device of a twenty-second aspect of the present disclosure includes the radiation detector of any one of the first aspect to the twenty-first aspect, wherein a controller configured to output a control signal in order to read the electrical charges accumulated in the plural pixels, a driver configured to output a drive signal in order to read the electrical charges from the plural pixels in response to the control signal, and a signal processor configured to generate and output image data in response to an input electrical signal when input with the electrical signal according to the electrical charges read from the plural pixels.

A radiographic imaging device of a twenty-third aspect of the present disclosure is the radiographic imaging device of the twenty-second aspect, wherein the controller and the radiation detector are provided arranged in a direction intersecting a stacking direction of the base member, the layer formed with the plural pixels, and the conversion layer in the radiation detector.

A radiographic imaging device of a twenty-fourth aspect of the present disclosure is the radiographic imaging device of the twenty-second aspect, further including a power source configured to supply electric power to at least one out of the controller, the driver, or the signal processor, wherein the power source, the controller, and the radiation detector are provided arranged in a direction intersecting a stacking direction of the sensor substrate, the conversion layer, and the neutral stress plane adjustment member in the radiation detector.

A radiographic imaging device of a twenty-fifth aspect of the present disclosure is the radiographic imaging device of the twenty-second aspect, further including a case that includes an irradiated face for irradiation with radiation, and that is configured to house the radiation detector in a state in which it is the sensor substrate from out of the sensor substrate and the conversion layer of the radiation detector that opposes the irradiated face.

In the first aspect, the radiation detector and electric circuitry are arranged in a direction intersecting the stacking direction in which the conversion layer and the sensor substrate are stacked. This enables the sensor substrate and the conversion layer to be suppressed from detaching from one another when the radiation detector is on its own, in comparison to a radiographic imaging device in which a bending adjustment member is provided across the entirety of the radiation detector and the electric circuitry.

The second aspect enables the sensor substrate and the conversion layer to be suppressed from detaching from one another in comparison to cases in which the predetermined range is a range that is longer than the distance between the interface and the neutral stress plane in cases in which the neutral stress plane adjustment member is not provided.

The third aspect enables the sensor substrate and the conversion layer to be suppressed from detaching from one another in comparison to cases in which the neutral stress plane adjustment member is not provided at the region covering the region where the sensor substrate and the conversion layer oppose each other.

The fourth aspect enables the thickness of the neutral stress plane adjustment member in order to obtain the desired rigidity to be suppressed, in comparison to cases in which the bending elastic modulus is less than 150 MPa or greater than 2500 MPa.

The fifth aspect enables the sensor substrate and the conversion layer to be suppressed from detaching from one another in comparison to cases that do not include at least one material out of polycarbonate, polyethylene terephthalate, or low density polyethylene.

The sixth aspect enables the sensor substrate and the conversion layer to be suppressed from detaching from one another in comparison to cases in which the coefficient of thermal expansion ratio is less than 0.5 or greater than 4.

The seventh aspect enables the sensor substrate and the conversion layer to be suppressed from detaching from one another in comparison to cases in which this coefficient of thermal expansion is less than 30 ppm/K or greater than 200 ppm/K.

The eighth aspect enables the conversion layer to detach from the sensor substrate less readily than in cases in which the cohesion layer is not provided.

The ninth aspect enables the sensor substrate and the conversion layer to be suppressed from detaching from one another in comparison to cases in which the buffer layer is not provided.

The tenth aspect enables advantageous effects to be obtained in addition to the advantageous effect of suppressing the sensor substrate and the conversion layer from detaching from one another, in comparison to cases in which the neutral stress plane adjustment member is configured of a single film.

The eleventh aspect enables static build-up in the sensor substrate to be prevented in comparison to cases in which the anti-static film is not provided.

The twelfth aspect enables static build-up in the sensor substrate to be prevented in comparison to cases in which the anti-static film is provided further toward the first surface side than the neutral stress plane adjustment film.

The thirteenth aspect enables moisture proofing performance of the base member and the conversion layer to be enhanced in comparison to cases in which the moisture-proof film is not provided.

The fourteenth aspect enables moisture proofing performance of the base member and the conversion layer to be enhanced in comparison to cases in which the moisture-proof film is provided further toward the first surface side than the neutral stress plane adjustment film.

The fifteenth aspect enables back-scattered radiation generated inside the base member to be suppressed in comparison to cases in which the base member does not include the fine particle layer containing inorganic fine particles having a mean particle size of from 0.05 µm to 2.5 µm.

The sixteenth aspect enables the pixels to be formed with good precision in comparison to cases in which the base member includes the fine particle layer on the first surface side.

The seventeenth aspect enables back-scattered radiation to be effectively suppressed and enables absorption of radiation in the fine particle layer to be suppressed, in comparison to cases in which the fine particles do not include an element having an atomic number that is greater than the atomic number of the elements configuring the base member and that is an atomic number not exceeding 30.

The eighteenth aspect enables the base member to be suited to manufacture of the pixels in comparison to cases in which the base member has a coefficient of thermal expansion greater than 20 ppm/K in a temperature range from 300° C. to 400° C.

The nineteenth aspect enables the base member to be suited to manufacture of the pixels in comparison to cases in which the base member has a heat shrinkage ratio in a machine direction at 400° C. and at a thickness of 25 µm of greater than 0.5%, or has a modulus of elasticity at 500° C. of less than 1 GPa.

The twentieth aspect enables bending of the base member to be suppressed in comparison to cases in which the rigidity of the neutral stress plane adjustment member is no higher than the rigidity of the base member.

The twenty-first aspect enables the efficiency of radiation to visible light conversion to be enhanced in comparison to cases in which the conversion layer does not include CsI.

The twenty-second aspect enables the sensor substrate and the conversion layer to be suppressed from detaching from one another even when employed bent, in comparison to cases in which a different radiation detector to the radiation detector of any one of the first aspect to the twenty-first aspect is included.

The twenty-third aspect enables the sensor substrate and the conversion layer to be suppressed from detaching from one another even in cases in which the controller and the radiation detector are provided arranged in a direction intersecting the stacking direction of the base member, the layer formed with the plural pixels, and the conversion layer in the radiation detector, in comparison to cases in which a different radiation detector to the radiation detector of any one of the first aspect to the twenty-first aspect is included.

The twenty-fourth aspect enables the sensor substrate and the conversion layer to be suppressed from detaching from one another even in cases in which the power source, the controller, and the radiation detector are provided arranged in a direction intersecting the stacking direction of the sensor substrate, the conversion layer, and the neutral stress plane adjustment member in the radiation detector, in comparison to cases in which a different radiation detector to the radiation detector of any one of the first aspect to the twenty-first aspect is included.

The twenty-fifth aspect enables the image quality of radiographic images to be enhanced in comparison to cases in which the case houses the radiation detector in a state in which the irradiated face and the conversion layer oppose each other.

The invention claimed is:

1. A radiation detector comprising:
   a sensor substrate that includes a flexible base, and a layer provided on a first surface of the base and formed with a plurality of pixels configured to accumulate electrical charge generated in response to light converted from radiation;
   a conversion layer that is provided on the opposite side of the layer formed with the plurality of pixels to the side where the base is provided and that is configured to convert radiation into the light; and
   a neutral stress plane adjustment layer that is provided on a second surface side of the base on the opposite side of the base to the first surface and that is configured such that a position of a neutral stress plane is within a predetermined range in a stacking direction in which the sensor substrate and the conversion layer are stacked from an interface at a face of the conversion layer opposing the sensor substrate wherein a distance (d2) between the interface and the neutral stress plane in cases in which the radiation detector includes the neutral stress plane adjustment layer is shorter than a distance (d1) between the interface and the neutral stress plane in cases in which the radiation detector does not include the neutral stress plane adjustment layer.

2. The radiation detector of claim 1, wherein the predetermined range is a range that is shorter than the distance (d1) between the interface and the neutral stress plane in cases in which the neutral stress plane adjustment layer is not provided.

3. The radiation detector of claim 1, wherein the neutral stress plane adjustment layer is provided at a region covering at least a region where the sensor substrate and the conversion layer oppose each other.

4. The radiation detector of claim 1, wherein the neutral stress plane adjustment layer has a bending elastic modulus of from 150 MPa to 2500 MPa.

5. The radiation detector of claim 1, wherein a material of the neutral stress plane adjustment layer includes at least one material out of polycarbonate, polyethylene terephthalate, or low density polyethylene.

6. The radiation detector of claim 1, wherein a ratio of a coefficient of thermal expansion of the neutral stress plane adjustment layer with respect to a coefficient of thermal expansion of the conversion layer is from 0.5 to 4.

7. The radiation detector of claim 1, wherein the neutral stress plane adjustment layer has a coefficient of thermal expansion of from 30 ppm/K to 200 ppm/K.

8. The radiation detector of claim 1, further comprising a cohesion layer provided at the interface and contacting the sensor substrate and the conversion layer.

9. The radiation detector of claim 1, further comprising a buffer layer provided between the sensor substrate and the conversion layer, and configured to buffer a difference between a coefficient of thermal expansion of the conversion layer and a coefficient of thermal expansion of the sensor substrate.

10. The radiation detector of claim 1, wherein the neutral stress plane adjustment layer includes a plurality of films stacked along the stacking direction, the plurality of films having different functions to each other.

11. The radiation detector of claim 10, wherein the plurality of films include a neutral stress plane adjustment film and an anti-static film.

12. The radiation detector of claim 11, wherein the anti-static film is provided further toward the second surface side than the neutral stress plane adjustment film.

13. The radiation detector of claim 10, wherein the plurality of films include a neutral stress plane adjustment film and a moisture-proof film.

14. The radiation detector of claim 13, wherein the moisture-proof film is provided further toward the second surface side than the neutral stress plane adjustment film.

15. The radiation detector of claim 1, wherein the base has a coefficient of thermal expansion not greater than 20 ppm/K in a temperature range from 300° C. to 400° C.

16. The radiation detector of claim 1, wherein the neutral stress plane adjustment layer has a higher rigidity than the base.

17. The radiation detector of claim 1, wherein the conversion layer includes CsI.

18. A radiographic imaging device comprising:

the radiation detector of claim 1;

a controller circuit configured to output a control signal in order to read the electrical charges accumulated in the plurality of pixels;

a driver circuit configured to output a drive signal in order to read the electrical charges from the plurality of pixels in response to the control signal; and a signal processing circuit configured to generate and output image data in response to an input electrical signal when input with the electrical signal according to the electrical charges read from the plurality of pixels.

19. The radiographic imaging device of claim 18, wherein the controller circuit and the radiation detector are provided arranged in a direction intersecting a stacking direction of the base, the layer formed with the plurality of pixels, and the conversion layer in the radiation detector.

20. The radiographic imaging device of claim 18, further comprising a case that includes an irradiated face for irradiation with radiation, and that is configured to house the radiation detector in a state in which it is the sensor substrate from out of the sensor substrate and the conversion layer of the radiation detector that opposes the irradiated face.

* * * * *